(12) United States Patent
Feng et al.

(10) Patent No.: US 12,702,963 B2
(45) Date of Patent: Aug. 11, 2026

(54) METHODS AND COMPOSITIONS RELATED TO LANTHANIDE-ENCODED MICROBEADS

(71) Applicants: CZ Biohub SF, LLC, San Francisco, CA (US); The Board of Trustees of the Leland Stanford Junior University, Stanford, CA (US); University of Copenhagen, Copenhagen (DK)

(72) Inventors: Yinnian Feng, Stanford, CA (US); Adam K. White, Stanford, CA (US); Jamin B. Hein, Stanford, CA (US); Polly M. Fordyce, Stanford, CA (US)

(73) Assignees: CZ Biohub SF, LLC, San Francisco, CA (US); The Board of Trustees of the Leland Stanford Junior University, Stanford, CA (US); University of Copenhagen, Copenhagen (DK)

( * ) Notice: Subject to any disclaimer, the term of this patent is extended or adjusted under 35 U.S.C. 154(b) by 663 days.

(21) Appl. No.: 18/000,884

(22) PCT Filed: Jun. 10, 2021

(86) PCT No.: PCT/US2021/036769

§ 371 (c)(1),
(2) Date: Dec. 6, 2022

(87) PCT Pub. No.: WO2021/252735

PCT Pub. Date: Dec. 16, 2021

(65) Prior Publication Data

US 2023/0211307 A1 Jul. 6, 2023

Related U.S. Application Data

(60) Provisional application No. 63/037,804, filed on Jun. 11, 2020.

(51) Int. Cl.

| | |
|---|---|
| ***B01J 13/18*** | (2006.01) |
| ***B01L 3/00*** | (2006.01) |
| ***G01N 33/58*** | (2006.01) |

(52) U.S. Cl.

CPC ......... *B01J 13/18* (2013.01); *B01L 3/502784* (2013.01); *G01N 33/582* (2013.01); *B01L 2200/0673* (2013.01)

(58) Field of Classification Search

CPC ... A61K 48/005; A61K 48/0075; A61P 27/02; C07K 14/47; C12N 15/86;

(Continued)

(56) References Cited

U.S. PATENT DOCUMENTS

| | | | |
|---|---|---|---|
| 10,241,045 | B2 | 3/2019 | Baxter et al. |
| 2007/0248993 | A1 | 10/2007 | Seul et al. |

(Continued)

OTHER PUBLICATIONS

International Application No. PCT/US2021/036769, International Preliminary Report on Patentability mailed on Dec. 22, 2022, 9 pages.

(Continued)

*Primary Examiner* — Jennifer Wecker

(74) *Attorney, Agent, or Firm* — Kilpatrick Townsend & Stockton LLP

(57) ABSTRACT

The present disclosure provides methods, devices, systems and kits for producing polymeric microbeads, including lanthanide-encoded microbeads. Among others, the present disclosure provides methods, systems and kits for producing functionalized microbeads that include on their surfaces amphipathic moieties with free reactive groups that remain free and can be used for covalently coupling molecules or moieties of inters to the microbeads.

20 Claims, 28 Drawing Sheets

(58) Field of Classification Search
CPC ........... C12N 2750/14122; C12N 2750/14143; C12N 2750/14145; C12N 2800/22; B01L 2200/0673; B01L 3/502784; B01J 13/18; B82Y 30/00; G01N 33/582
See application file for complete search history.

(56) References Cited

U.S. PATENT DOCUMENTS

| | | | | |
|---|---|---|---|---|
| 2010/0081583 | A1 | 4/2010 | Shirazi | |
| 2015/0192518 | A1 | 7/2015 | Baxter et al. | |
| 2015/0377997 | A1* | 12/2015 | Zabow | A61K 49/1818 324/309 |
| 2017/0362307 | A1 | 12/2017 | Ingber et al. | |
| 2018/0196040 | A1* | 7/2018 | Holden | G01N 33/6872 |
| 2022/0228198 | A1* | 7/2022 | White | C12Q 1/689 |

OTHER PUBLICATIONS

International Application No. PCT/US2021/036769, International Search Report and the Written Opinion mailed on Nov. 1, 2021, 12 pages.
International Application No. PCT/US2021/036769, Invitation to Pay Additional Fees and, Where Applicable, Protest Fee mailed on Aug. 25, 2021, 2 pages.
Abate et al., Impact of Inlet Channel Geometry on Microfluidic Drop Formation, Physical Review E, vol. 80, No. 2, Aug. 2009, pp. 1-5.
Ahmed et al., Operation of Droplet-Microfluidic Devices with a Lab Centrifuge, Micromachines, vol. 7, No. 161, Sep. 6, 2016, pp. 1-8.
An et al., Controlled Synthesis and Luminescent Properties of Assembled Spherical PxV1-xO4:Ln3+ (Ln=Eu, Sm, Dy or Tm) Phosphors with High Quantum Efficiency, Royal Society of Chemistry, vol. 5, Jun. 2015, pp. 52533-52542.
Anna et al., Formation of Dispersions Using "Flow Focusing" in Microchannels, Applied Physics Letters, vol. 82, No. 3, Jan. 20, 2003, pp. 364-366.
Anna et al., Microscale Tipstreaming in a Microfluidic Flow Focusing Device, Physics of Fluids, vol. 18, No. 12, Dec. 8, 2006, pp. 1-13.
Appleyard et al., Multiplexed Protein Quantification with Barcoded Hydrogel Microparticles, Analytical Chemistry, vol. 83, No. 1, Jan. 1, 2011, pp. 193-199.
Birtwell et al., Microparticle Encoding Technologies for High-throughput Multiplexed Suspension Assays, Integrative Biology, vol. 1, Jun. 2009, pp. 345-362.
Braeckmans et al., Encoding Microcarriers: Present and Future Technologies, Nature Reviews Drug Discovery, vol. 1, No. 6, Jun. 2002, pp. 447-456.
Broder et al., Diffractive Micro Bar Codes for Encoding of Biomolecules in Multiplexed Assays, Analytical chemistry, vol. 80, No. 6, Mar. 15, 2008, pp. 1902-1909.
Cederquist et al., Encoded Anisotropic Particles for Multiplexed Bioanalysis, Wiley Interdisciplinary Reviews: Nanomedicine and Nanobiotechnology, vol. 2, Nov.-Dec. 2010, pp. 578-600.
Chapin et al., Rapid microRNA Profiling on Encoded Gel Microparticles, Angewandte Chemie International, vol. 50, No. 10, Mar. 1, 2011, pp. 2289-2293.
Chen et al., Centrifugal Micro-Channel Array Droplet Generation for Highly Parallel Digital PCR, Lab on a Chip, vol. 17, Jan. 21, 2017, pp. 235-240.
Choi et al., Luminescent Properties of PEG-added Nanocrystalline YVO4:Eu3+ Phosphor Prepared by a Hydrothermal Method, Journal of Luminescence, vol. 130, No. 4, Apr. 2010, pp. 549-553.
Christopher et al., Microfluidic Methods for Generating Continuous Droplet Streams, Journal of Physics D: Applied Physics, vol. 40, No. 19, Sep. 21, 2007, pp. R319-R336.
Conchouso et al., Three-Dimensional Parallelization of Microfluidic Droplet Generators for a Litre Per Hour Volume Production of Single Emulsions, Lab on a Chip, vol. 14, Jun. 2014, pp. 3011-3020.
Cramer et al., Drop Formation in a Co-Flowing Ambient Fluid, Chemical Engineering Science, vol. 59, No. 15, Aug. 2004, pp. 3045-3058.
Cubaud et al., Capillary Threads and Viscous Droplets in Square Microchannels, Physics of Fluids, vol. 20, No. 5, May 1, 2008, pp. 1-11.
Dagher et al., Ensemble Multicolour FRET Model Enables Barcoding at Extreme FRET Levels, Nature Nanotechnology, vol. 13, No. 10, Oct. 2018, 10 pages.
Dangla et al., Droplet Microfluidics Driven by Gradients of Confinement, Proceedings of the National Academy of Sciences, vol. 110, No. 3, Jan. 15, 2013, pp. 853-858.
Dreyfus et al., Ordered and Disordered Patterns in Two-Phase Flows in Microchannels, Physical Review Letters, vol. 90, No. 14, Apr. 11, 2003, pp. 1-4.
Femmer et al., High-Throughput Generation of Emulsions and Microgels in Parallelized Microfluidic Drop-Makers Prepared by Rapid Prototyping, ACS Applied Materials & Interfaces, vol. 7, No. 23, Jun. 17, 2015, pp. A-D.
Finkel et al., Peer Reviewed: Barcoding the Microworld, Analytical Chemistry, vol. 76, Oct. 1, 2004, pp. 352A-359A.
Fulton et al., Advanced Multiplexed Analysis with the FlowMetrixTM System, Clinical Chemistry, vol. 43, No. 9, Sep. 1997, pp. 1749-1756.
Ganan-Calvo et al., Perfectly Monodisperse Microbubbling by Capillary Flow Focusing, Physical Review Letters, vol. 87, Dec. 31, 2001, pp. 1-4.
Garstecki et al., Formation of Droplets and Bubbles in a Microfluidic T-Junction Scaling and Mechanism of Break-up, Lab on a Chip, vol. 6, No. 3, Mar. 2006, pp. 437-446.
Gerver et al., Programmable Microfluidic Synthesis of Spectrally Encoded Microspheres, Lab Chip, vol. 12, No. 22, Nov. 2012, pp. 4716-4723.
Harink et al., An Open-Source Software Analysis Package for Microspheres with Ratiometric Barcode Lanthanide Encoding (MRBLEs), The Public Library of Science One, vol. 14, No. 3, Mar. 22, 2019, pp. 1-20.
Heller, Dna Microarray Technology: Devices, Systems, and Applications, Annual Review of Biomedical Engineering, vol. 4, No. 1, Aug. 2002, pp. 129-153.
Hermanson, Bioconjugate Techniques, Academic Press, Third Edition, Jul. 2013, 32 pages.
Hong et al., Flow Rate Effect on Droplet Control in a Co-Flowing Microfluidic Device, Microfluidics and Nanofluidics, vol. 3, Nov. 30, 2006, pp. 341-346.
Houser, Bio-Rad's Bio-Plex® Suspension Array System, xMAP Technology Overview, Archives of Physiology and Biochemistry, vol. 118, No. 4, Oct. 2012, pp. 192-196.
Huft et al., Three-dimensional Large-scale Microfluidic Integration by Laser Ablation of Interlayer Connections, Supplementary Information, Lab on a Chip, vol. 10, No. 18, Sep. 21, 2010, 6 pages.
Huft et al., Three-dimensional Large-scale Microfluidic Integration by Laser Ablation of Interlayer Connections, Lab on a Chip, vol. 10, No. 18, Sep. 21, 2010, pp. 2358-2365.
Kim et al., Shape-encoded Silica Microparticles for Multiplexed Bioassays, Chemical Communications, vol. 51, No. 60, Jun. 2015, pp. 12130-12133.
Kingsmore, Multiplexed Protein Measurement: Technologies and Applications of Protein and Antibody Arrays, Nature Reviews Drug Discovery, vol. 5, No. 4, Apr. 2006, pp. 310-320.
Lawrie et al., Synthesis of Optically Complex Core-shell Colloidal Suspensions: Pathways to Multiplexed Biological Screening, Advanced Functional Materials, vol. 13, No. 11, Nov. 2003, pp. 887-896.
Le Goff et al., Hydrogel Microparticles for Biosensing, European Polymer Journal, vol. 72, Nov. 2015, pp. 386-412.
Lee et al., Colour-barcoded Magnetic Microparticles for Multiplexed Bioassays, Supplementary Information, Nature Materials, vol. 9, No. 9, Sep. 2010, pp. 1-11.
Lee et al., Colour-barcoded Magnetic Microparticles for Multiplexed Bioassays, Nature Materials, vol. 9, No. 9, Sep. 2010, pp. 745-749.

(56) References Cited

OTHER PUBLICATIONS

Lee et al., Spheroid-Based Three-Dimensional Liver-on-a-Chip to Investigate Hepatocyte-Hepatic Stellate Cell Interactions and Flow Effects, Lab on a Chip, vol. 13, Sep. 21, 2013, pp. 3529-3537.
Li et al., Multiple Modular Microfluidic (M3) Reactors for the Synthesis of Polymer Particles, Lab on a Chip, vol. 9, Sep. 21, 2009, pp. 2715-2721.
Li et al., Optimized Reaction Conditions for Amide Bond Formation in DNA-Encoded Combinatorial Libraries, ACS Combinatorial Science, vol. 18, No. 8, Aug. 8, 2016, pp. 438-443.
Liu et al., Preparation of Fluorescence-Encoded Microspheres Based on Hydrophobic Conjugated Polymer-Dye Combination and the Immunoassay, ACS Applied Bio Materials, vol. 2, No. 7, Jul. 2019, pp. 3009-3018.
Liu et al., Preparation of Fluorescence-Encoded Microspheres Based on Hydrophobic Conjugated Polymer-Dye Combination and the Immunoassay, Supporting Information, ACS Applied Bio Materials, vol. 2, No. 7, Jul. 2019, pp. S1-S8.
Mimitou et al., Multiplexed Detection of Proteins, Transcriptomes, Clonotypes and CRISPR Perturbations in Single Cells, Supplementary Information, Nature Methods, vol. 16, No. 5, May 2019, 23 pages.
Mimitou et al., Multiplexed Detection of Proteins, Transcriptomes, Clonotypes and CRISPR Perturbations in Single Cells, Nature Methods, vol. 16, No. 5, May 2019, pp. 409-412.
Moorthy et al., Microfluidic Based Platform for Characterization of Protein Interactions in Hydrogel Nanoenvironments, Analytical Chemistry, vol. 79, No. 14, Jul. 15, 2007, pp. 5322-5327.
Mulligan et al., Scale-Up and Control of Droplet Production in Coupled Microfluidic Flow-Focusing Geometries, Microfluidics and Nanofluidics, vol. 13, Jul. 2012, pp. 65-73.
Nallur et al., Protein and Nucleic Acid Detection by Rolling Circle Amplification on Gel-based Microarrays, Biomedical Microdevices, vol. 5, No. 2, Jun. 2003, pp. 115-123.
Nguyen et al., Peptide Library Synthesis on Spectrally Encoded Beads for Multiplexed Protein/Peptide Bioassays, Microfluidics, BioMEMS, and Medical Microsystems XV, International Society for Optics and Photonics, vol. 10061, Feb. 28, 2017, pp. 1-11.
Nguyen et al., Programmable Microfluidic Synthesis of Over One Thousand Uniquely Identifiable Spectral Codes, Advanced Optical Materials, vol. 5, No. 3, Feb. 2, 2017, pp. 1-12.
Nguyen et al., Quantitative Mapping of Protein-Peptide Affinity Landscapes Using Spectrally Encoded Beads, eLife, Jul. 8, 2019, pp. 1-28.
Nisisako et al., High-volume Production of Single and Compound Emulsions in a Microfluidic Parallelization Arrangement Coupled with Coaxial Annular World-to-chip Interfaces, Supplementary Information, Lab on a Chip, vol. 12, No. 18, Sep. 21, 2012, 4 pages.
Nisisako et al., High-volume Production of Single and Compound Emulsions in a Microfluidic Parallelization Arrangement Coupled with Coaxial Annular World-to-chip Interfaces, Lab on a Chip, vol. 12, No. 18, Sep. 21, 2012, pp. 3426-3435.
Peng et al., The Effect of Interfacial Tension on Droplet Formation in Flow-Focusing Microfluidic Device, Biomedical Microdevices, vol. 13, No. 3, Jun. 2011, pp. 559-564.
Purohit et al., Multiplex Glycan Bead Array for High Throughput and High Content Analyses of Glycan Binding Proteins, Nature Communications, vol. 9, No. 1, Jan. 17, 2018, pp. 1-12.
Riechers et al., Surfactant Adsorption Kinetics in Microfluidics, Proceedings of the National Academy of Sciences, vol. 113, No. 41, Oct. 11, 2016, p. 11465-11470.
Roh et al., Microfluidic Fabrication of Encoded Hydrogel Microparticles for Application in Multiplex Immunoassay, BioChip Journal, vol. 13, No. 1, Mar. 2019, pp. 64-81.
Romanowsky et al., High Throughput Production of Single Core Double Emulsions in a Parallelized Microfluidic Device, Lab on a Chip, vol. 12, No. 4, Feb. 2012, pp. 802-807.
Shin et al., Centrifuge-Based Step Emulsification Device for Simple and Fast Generation of Monodisperse Picoliter Droplets, Sensors and Actuators B: Chemical, vol. 301, Dec. 12, 2019, 2 pages.
Stoeckius et al., Simultaneous Epitope and Transcriptome Measurement in Single Cells, Nature Methods, vol. 14, No. 9, Sep. 2017, pp. 865-868.
Sugiura et al., Preparation of Monodispersed Solid Lipid Microspheres Using a Microchannel Emulsification Technique, Journal of Colloid Interface Science, vol. 227, No. 1, Jul. 1, 2000, pp. 95-103.
Tan et al., Drop Dispenser in a Cross-junction Microfluidic Device: Scaling and Mechanism of Break-up, Chemical Engineering Journal, vol. 136, No. 2-3, Mar. 2008, pp. 306-311.
Taylor, The Formation of Emulsions in Definable Fields of Flow, Proceedings of the Royal Society of London. Series A, Containing Papers of a Mathematical and Physical Character, vol. 146, No. 858, Oct. 1, 1934, pp. 501-523.
Thorsen et al., Dynamic Pattern Formation in a Vesicle-Generating Microfluidic Device, Physical Review Letters, vol. 86, No. 18, Apr. 30, 2001, pp. 4163-4166.
Tice et al., Effects of Viscosity on Droplet Formation and Mixing in Microfluidic Channels, Analytica Chimica Acta, vol. 507, No. 1, Apr. 1, 2004, pp. 73-77.
Ullah et al., Classification, Processing and Application of Hydrogels: A Review, Materials Science and Engineering: C, vol. 57, Dec. 1, 2015, pp. 414-433.
Umbanhowar et al., Monodisperse Emulsion Generation via Drop Break Off in a Coflowing Stream, Langmuir, vol. 16, No. 2, Jan. 2000, pp. 347-351.
Upadhyay et al., Influence of Crystallite Size on the Magnetic Properties of Fe3O4 Nanoparticles, Journal of Alloys and Compounds, vol. 678, Sep. 5, 2016, pp. 478-485.
Utada et al., Dripping to Jetting Transitions in Coflowing Liquid Streams, Physical Review Letters, vol. 99, No. 9, Aug. 2007, pp. 1-4.
Utharala et al., A Versatile, Low-Cost, Multiway Microfluidic Sorter for Droplets, Cells, and Embryos, Analytical Chemistry, vol. 90, No. 10, May 2018, pp. 5982-5988.
Visser et al., In-Air Microfluidics Enables Rapid Fabrication of Emulsions, Suspensions, and 3D Modular (Bio)materials, Science Advances, vol. 4, No. 1, Jan. 31, 2018, pp. 1-8.
Wang et al., Multicolor Tuning of (Ln, P)-Doped YVO4 Nanoparticles by Single-Wavelength Excitation, Angewandte Chemie International, vol. 47, Issue5, Jan. 18, 2008, pp. 906-909.
Ward et al., Microfluidic Flow Focusing: Drop Size and Scaling in Pressure Versus Flow-Rate-Driven Pumping, Electrophoresis, vol. 26, No. 19, Oct. 2005, pp. 3716-3724.
Waterboer et al., Suppression of Non-specific Binding in Serological Luminex Assays, Journal of Immunological Methods, vol. 309, No. 1-2, Feb. 20, 2006, pp. 200-204.
Wilson et al., Encoded Microcarriers for High-throughput Multiplexed Detection, Angewandte Chemie International Edition, vol. 45, Sep. 18, 2006, pp. 6104-6117.
Xia et al., Soft Lithography, Angewandte Chemie International Edition, vol. 37, No. 5, Mar. 16, 1998, pp. 550-575.
Xiong et al., Formation of Bubbles in a Simple Co-flowing Microchannel, Journal of Micromechanics and Microengineering, vol. 17, No. 5, Apr. 17, 2007, pp. 1002-1011.
Xu et al., Rapid Synthesis of Size-controllable YVO4 Nanoparticles by Microwave Irradiation, Solid State Communications, vol. 130, No. 7, May 2004, pp. 465-468.
Yadavali et al., Silicon and Glass Very Large Scale Microfluidic Droplet Integration for Terascale Generation of Polymer Microparticles, Nature Communications, vol. 9, No. 1, Mar. 26, 2018, pp. 1-9.
Yobas et al., High-Performance Flow-Focusing Geometry for Spontaneous Generation of Monodispersed Droplets, Lab on a Chip, vol. 6, No. 8, Aug. 2006, pp. 1073-1079.
Zhang et al., Fluorescence Upconversion Microbarcodes for Multiplexed Biological Detection: Nucleic Acid Encoding, Advanced Materials, vol. 23, No. 33, Sep. 2011, pp. 3775-3779.
Zhang et al., Rare-Earth Upconverting Nanobarcodes for Multiplexed Biological Detection, Small, vol. 7, No. 14, Jul. 18, 2011, pp. 1972-1976.

* cited by examiner

Figure 1F
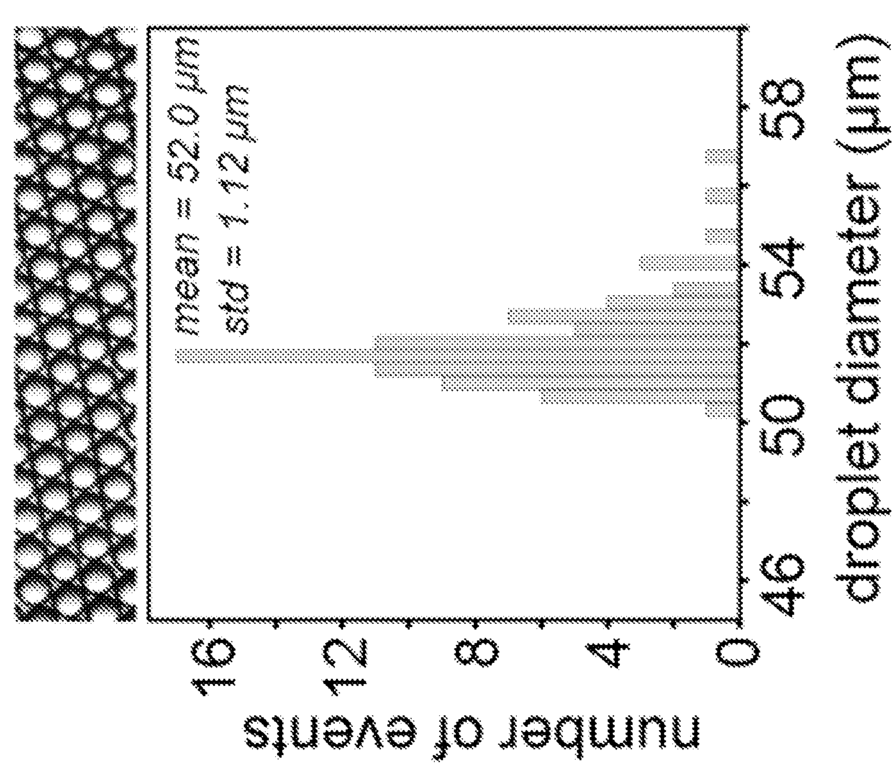
mean = 52.0 μm
std = 1.12 μm
number of events
0
4
8
12
16
46
50
54
58
droplet diameter (μm)

Figure 5A linear amplification (2xN)

vs.

exponential amplification ($2^N$)

Droplet splitter

METHODS AND COMPOSITIONS RELATED TO LANTHANIDE-ENCODED MICROBEADS

CROSS REFERENCE TO RELATED APPLICATIONS

This application is a national phase application of PCT Application No. PCT/US2021/036769, filed Jun. 10, 2021, which claims benefit of U.S. Provisional Patent Application No. 63/037,804, filed Jun. 11, 2020. The above applications are incorporated herein by reference in their entirety.

FEDERALLY SPONSORED RESEARCH AND DEVELOPMENT

This invention was made with Government support under contract GM123641 awarded by the National Institutes of Health. The Government has certain rights in the invention.

BACKGROUND OF THE INVENTION

Recently developed technical abilities to identify molecules across a cell's genome, transcriptome, and proteome dramatically increased the need for technologies capable of detecting interactions between biological macromolecules at scale for the comprehensive understanding of the interactome networks. Multiplexed bioassays, in which binding is assessed between a single "bait" molecule and many possible "prey" interactors, can reduce the number of assays required to explore a potential interactome space and speed the pace of discovery. Pioneering examples of these assays used spatial arrays to test thousands to millions of potential interactions in a single experiment (1, 2). However, spatial arrays suffer from relatively slow kinetics (as bait molecules are immobilized on a planar surface) and typically require relatively large sample amounts (1). Multiplexed microbead-based assays are an appealing alternative to spatial arrays, providing near fluid-phase interfacial kinetics, many replicates per experiment, opportunities for quality control, and the ability to flexibly couple different probes and targets across experiments (3-5). Spectrally encoded microbeads, in which microbeads are embedded with ratiometric combinations of fluorescent or luminescent materials, provide a particularly convenient format for multiplexed assays and are used for a wide variety of applications (6-16). One example of commercially available spectrally encoded microbead-based platform is Luminex® multi-analyte profiling (xMAP) technology. xMAP microbeads consist of magnetic polystyrene microspheres that encapsulate distinct proportions of red and infrared fluorophores, each of which comprises a unique spectral code. xMAP microbeads are compatible with flow cytometry (17) and are used for a variety of bioassays (18), but suffer from a variety of limitations. The use of fluorescent dyes for encoding limits the possible coding space to 500 and code sets typically contain <100 codes. Also, hydrophobic polystyrene microbeads cannot detect low affinity interactions due to widespread nonspecific binding mediated by hydrophobic interactions (19). Spectrally encoded hydrogel microbeads have also been used for a variety of biomedical and sensing applications (20, 21). Hydrogel microbeads are comprised of a cross-linked, hydrated polymeric network made up of one or more hydrophilic monomers, providing near fluid-phase kinetics at functionalized surfaces as well as high-efficiency molecular loading (22, 23), and microfluidic droplet generators have been used to produce and polymerize hydrogel microbeads at high-throughput (24). However, the use of fluorescent dyes to create spectral codes in most cases has limited the number of unique spectral codes to <100 (25, 26). Moreover, fluorescently encoded microspheres are often incompatible with harsh organic solvents, precluding their use in a variety of solid-phase synthesis applications.

BRIEF SUMMARY OF THE INVENTION

The terms "invention," "the invention," "this invention" and "the present invention," as used in this document, are intended to refer broadly to all of the subject matter of this patent application and the claims below. Statements containing these terms should be understood not to limit the subject matter described herein or to limit the meaning or scope of the patent claims below. Covered embodiments of the invention are defined by the claims, not this summary. This summary is a high-level overview of various aspects of the invention and introduces some of the concepts that are described and illustrated in the present document and the accompanying figures. This summary is not intended to identify key or essential features of the claimed subject matter, nor is it intended to be used in isolation to determine the scope of the claimed subject matter. The subject matter should be understood by reference to appropriate portions of the entire specification, any or all figures and each claim. Some of the exemplary embodiments of the present invention are discussed below.

Included among the embodiments of the present invention and described in the present disclosure are methods for producing polymeric microbeads. Some embodiments of the methods of producing polymeric microbeads are methods for producing polymeric microbeads comprising lanthanide nanoparticles. Such methods may comprise the steps of: i) providing a first fluid comprising a microbead matrix component and lanthanide nanoparticles, and a second fluid, wherein the first fluid and the second fluid are immiscible; ii) contacting the first fluid with the second fluid in a microfluidic device, thereby forming droplets of the first fluid; iii) removing the formed droplets from the microfluidic device; and, iv) solidifying the microbead matrix component of the formed droplets removed from the microfluidic device, thereby forming the polymeric microbeads comprising lanthanide nanoparticles. Some embodiments of the methods of producing polymeric microbeads are methods for producing functionalized polymeric microbeads. Such methods may comprise the steps of: i) providing a first fluid comprising a microbead matrix component, and a second fluid comprising an amphipathic compound capable of covalently bonding with the microbead matrix component, wherein the first fluid is hydrophilic, the second fluid is hydrophobic, and the first fluid and the second fluid are immiscible; ii) contacting the first fluid with the second fluid, thereby forming droplets of the first fluid in the second fluid; and, iii) solidifying the microbead matrix component of the formed droplets removed from the microfluidic device, thereby forming the functionalized polymeric microbeads with surfaces comprising covalently bound amphipathic moieties comprising free reactive groups.

Included among the embodiments of the present invention and described in the present disclosure are devices for producing polymeric microbeads. Such devices can be microfluidic devices. A microfluidic device for producing polymeric microbeads can comprise: a first inlet port for a first fluid comprising a microbead matrix component; a second inlet port for a second fluid; one or more first flow channels fluidically connected with the first inlet port; one or more second flow channels fluidically connected with the second inlet port and intersecting with the one or more first flow channels at one or more intersections configured to provide a stream of droplets of the first fluid in the second fluid in one more droplet channels downstream of the one or more intersections; one or more droplet outlets downstream of and fluidically connected to the one or more droplet channels; and, one or more droplet outlet channels upstream of and fluidically connected to the one or more droplet outlets, and downstream of and fluidically connected with the one or more droplet channels, wherein the one or more first flow channels, the one or more second flow channels, the one or more droplet channels and the one or more droplet outlet channels are positioned substantially in plane, and wherein the one or more droplet outlet channels are fluidically connected to the one or more droplet channels via one or more fluidic connections out of the plane. Also included among the embodiments of the present invention and described in the present disclosure are systems for producing polymeric microbeads, which include (comprise) the devices for producing polymeric microbeads according to the embodiments of the present invention. Such systems can comprise, for example, compositions for producing polymeric microbeads, such as a microbead matrix component and/or lanthanide nanoparticles. Such systems can further comprise amphipathic compounds capable of covalently bonding with the microbead matrix component and comprising a reactive group that remains free upon the covalent bonding with the microbead matrix component.

Included among the embodiments of the present invention and described in the present disclosure are polymeric microbeads. Some embodiments of the polymeric microbeads comprise: i) a body composed of a polymer with lanthanide nanoparticles dispersed therein; and, ii) a surface comprising the polymer and covalently bound amphipathic moieties, wherein each amphipathic moiety comprises a free reactive group. Some embodiments of the polymeric microbeads comprise: i) a body composed of a hydrophilic polymer; and, ii) a surface comprising the hydrophilic polymer and covalently bound amphipathic moieties, wherein each amphipathic moiety comprises a free reactive group. Also included among the embodiments of the present invention and described in the present disclosure are populations of polymeric microbeads comprising multiples of the polymeric microbeads described in the present disclosure. Also included among the embodiments of the present invention and described in the present disclosure are methods for producing derivatized microbeads comprising coupling a molecule or a moiety to a free reactive group on a microbead surface. Also included among the embodiments of the present invention and described in the present disclosure are kits for producing polymeric microbeads, comprising a microbead matrix component, an amphipathic compound capable of covalently bonding with the polymerizable component, and, optionally, lanthanide nanoparticles.

BRIEF DESCRIPTION OF THE DRAWINGS

FIG. 1F shows a representative microphotographic image of produced droplets (top) and a histogram showing measured diameters for produced droplets (diameter=52.0+/−1.12 μm, coefficient of variation (CV)=2%, 79 droplets).

FIG. 5A is a schematic illustrating comparing linear and exponential droplet amplification.

DETAILED DESCRIPTION

Figure 1A:
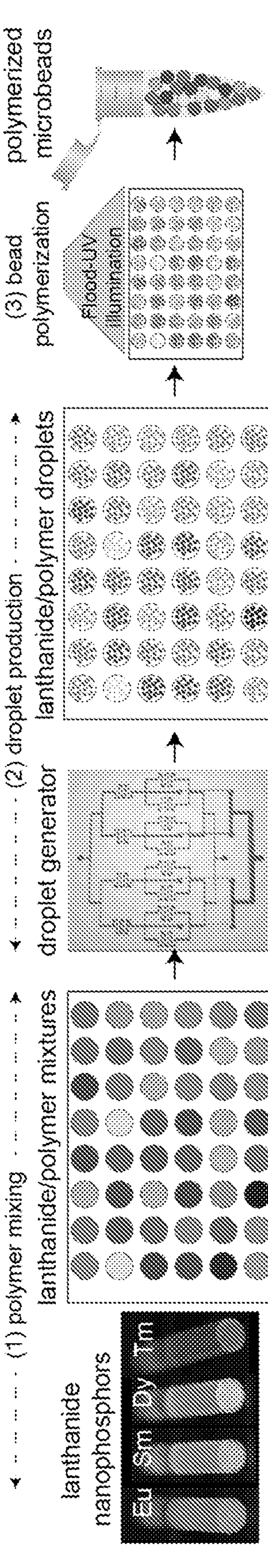
FIG. 1A is a schematic illustration of an exemplary high-throughput microbead production pipeline: (1) 'polymer mixing': ratiometric combinations of lanthanide nanoparticles (each combination possessing a unique spectral code) are mixed with aqueous polymer in individual wells of a multi-well plate; (2) droplet production: mixtures are introduced into a single-layer microfluidic droplet generation device; (3) microbead polymerization: droplets corresponding to each code are collected after synthesis and are exposed to UV light to drive polymerization into microbeads.

Microbeads spectrally encoded by ratiometric incorporation of lanthanide nanoparticles (Lns), which can be referred to as "spectrally encoded" or "lanthanide-encoded" microbeads, are described, for example, in (27) and U.S. Pat. No. 10,241,045. Lns have narrow and well-separated emission spectra, making it theoretically possible to generate code sets with $10^5$-$10^6$ unique members (28). The ability to produce and discriminate among over 1,100 codes in lanthanide-encoded microbeads is described in (27). Lanthanide-encoded microbeads were previously functionalized, subsequent to preparation, for on-bead solid-phase peptide synthesis (29,30). Described in the present disclosure is are new processes (methods), devices, systems and kits for efficient high-throughput generation of lanthanide-encoded microbeads. Some embodiments of the processes, devices, systems and kits described in the present disclosure are used for producing polymeric microbeads, including but not limited to lanthanide-encoded microbeads, bearing various functional groups for downstream chemical coupling or on-bead synthesis. Such functionalized polymeric microbeads, including but not limited to lanthanide-encoded functionalized polymeric microbeads, and related compositions and kits are included among the embodiments of the present invention. In some embodiments, the processes, devices, systems and kits described in the present disclosure are used for generating magnetic polymeric microbeads, including lanthanide-encoded polymeric microbeads. Magnetic polymeric microbeads and related compositions and kits are also included among the embodiments of the present invention.

Some embodiments of the processes for microbead production described in the present disclosure include "off-chip" (that is, not in the device used for microbead production) mixing of Lns-polymer mixtures, followed by droplet generation in a microfluidics device, followed by "off-chip" batch solidification (which can be polymerization) of droplets into microbeads. Some embodiments of the processes for microbead production described in the present disclosure include crosslinking of polymers bearing functional groups used for conjugation of molecules, including biological molecules, to microbead surfaces during microbead production. As discussed in more detail further in the present disclosure, the inventors generated monodisperse microbeads (with coefficient of variation (CV) of microbead diameter of 7% or less) containing 48 distinct well-resolved spectral codes (<0.01% probability of code-misassignment) in high-throughput fashion (with approximately 3,000,000 microbeads per spectral code produced in 20 minutes or less, including microbead washing steps). The inventors conceived a microfluidics device with droplet splitting for exponential amplification of microbead production. The inventors efficiently conjugated amine-functionalized oligonucleotides and entire proteins to microbeads bearing surface carboxyl groups, with even microbead surface coverage and estimated loading densities of $10^7$-$10^8$ molecules per microbead. In one example, biotin molecules were conjugated to amine-functionalized microbead surfaces, demonstrating the feasibility of direct peptide synthesis on the microbeads. The inventors magnetized polymeric microbeads, including lanthanide-encoded microbeads, by incorporating magnetic nanoparticles into the microbeads during their production.

The inventors conceived, and the present disclosure describes, various embodiments of methods, devices, systems and kits for producing polymeric microbeads, including lanthanide-encoded microbeads and polymeric microbeads with surfaces functionalized for subsequent conjugation of molecules, including biological molecules. Polymeric microbeads with functionalized surfaces ("surface-functionalized"), including surface-functionalized lanthanide-encoded microbeads, were also conceived by the inventors and are included among the embodiments of the present invention, along with the methods for producing derivatized polymeric microbeads with molecules (including biological molecules) or moieties covalently linked to reactive groups of surface-functionalized microbeads. Processes, devices, methods and kits for microbead production, as well as the microbeads conceived by the inventors are useful for a variety of applications, such as, but not limited to, multiplex biological assays, for example, the assays for nucleic acid and protein detection or detection of protein-protein interactions, materials science research, such as ingredient optimization of biomedical polymers, and environmental science and engineering, such as development of microbead adsorbents for containing pollutants.

The processes for microbead production described in the present disclosure can advantageously produce large batches of polymeric microbeads, including lanthanide-encoded polymeric microbeads at low cost. This capability is important for development of multiplexed microbead-based assays. For example, the capability to produce large microbead batches afforded by the processes described in the present disclosure makes it possible to accelerate initial assay development and optimization and/or minimize batch-to-batch microbead variations that leads to experimental noise. Previously, increased number of droplet generators within a device was used to boost production rates in a variety of different glass or PDMS droplet generation devices (including co-flow (36), T-junctions (37,38), flow-focusers (39-44), and discontinuous step generators (37, 38)). However, the need to route fluidic channels containing dispersed and continuous phases to and from many different droplet generating nozzles without channels intersecting one another presents significant fabrication challenges. In the past, such challenges were addressed by fabricating complex three-dimensional (3D) wafer designs (step emulsion) or assembling devices from multiple PDMS layers with laser-cut or punched "vias" connecting channels between layers. Connective tubing was previously used to connect different functional modules or devices in series (45, 46), but not within the same device. Microfluidic devices conceived by the inventors and described in the present disclosure use out-of-plane fluidic connection, which can be produced from tubing, to connect different channels within the same device. Embodiments of the microfluidic devices described in the present disclosure significantly reduces the fabrication complexity required to for flexible 3D routing, while still minimizing fluidic dead volumes. Exemplary devices and processes described in the present disclosure were capable of producing up to approximately 150,000 microbeads per minute with linear amplification, and up to approximately 600,000 microbeads per minute with exponential amplification using droplet splitting, representing a "pellet volume" (meaning the volume of the produced microbeads) of approximately 1 ml/hour or 3 ml/hour, respectively.

The ability to couple various molecules of interest to polymeric microbeads, including but not limited to spectrally-encoded microbeads, is important for various applications. For example, streptavidin or antibody-conjugated microbeads can be used to recruit and display biotinylated or epitope-tagged proteins. When molecules of interest are conjugated to microbeads with non-covalent interactions, even a small degree of dissociation leads to analyte loss and rebinding, driving cross-contamination among the microbeads, for example, during storage. The ability to covalently link molecules or moieties of interest to microbeads ("derivatization") sidesteps the above issues, but can be difficult to implement with many commonly used microbead matrices. Described in the present disclosure are the processes that incorporate functional groups into microbeads during microbead production. These processes generate droplets of a dispersed phase in a stream of continuous phase containing amphipathic compounds that (a) are capable of covalently bonding with the microbead matrix during solidification, and (b) bear reactive groups that remain free after microbead formation and can be used for subsequent covalent conjugation of molecules of interest to the surface of the microbeads. Some non-limiting examples of such reactive groups are carboxyl groups, amino groups, azide groups (which can be used for "click" chemistry), hydroxyl groups (which can be used for cyanogen bromide-activated coupling of proteins), and hydrazide groups (which can be used for oxidized carbohydrate proteins) and chloromethyl groups (which can be used for coupling of $NH_2$ groups in protein or other biological molecules) (47). The approach to producing functionalized microbeads described in the present disclosure can be useful for coupling different types of molecules of interest (such as both polypeptides and oligonucleotides) to the same population of microbeads by adding multiple amphipathic compounds to the hydrophobic phase during droplet generation. For example, the microbeads can be functionalized with multiple molecules used in CITE-seq (48) or ECCITE-seq (49).

Polymeric microbeads with magnetic properties described in the present disclosure ("magnetic microbeads") are useful, for example, for removing a portion of microbeads after their derivatization in order to assess derivatization quality. As an example, peptides may be synthesized directly on a mixture of magnetic and non-magnetic microbeads, making it possible to remove magnetic microbeads after peptide synthesis for peptide cleavage and investigation via mass spectrometry. Surprisingly, off-chip mixing and solidification, as well as incorporation of magnetic nanoparticles into lanthanide-encoded microbeads minimally increased the variance associated with each lanthanide-encoded magnetic microbead cluster, thus making it possible to produce magnetic lanthanide-encoded microbeads without detrimentally affecting their spectral encoding capacity.

The processes for polymeric microbead production described in the present disclosure can be integrated with robotic and high-throughput droplet generation technologies for a variety of applications. The processes described in the present disclosure can use commercially available and relatively inexpensive starting materials, facilitating low-cost development of various assays utilizing polymeric microbeads. In some of the embodiments of the processes described in the present disclosure, the components of the dispersed phase are mixed before introduction of the dispersed phase into a microfluidic device for droplet generation, which makes it possible to automate such processes for production of large sets of lanthanide-encoded microbeads using commercial liquid handling robots capable of mixing viscous solutions (for example, LabCyte Echo or Bravo liquid handling systems). The dispersed phase mixed "off chip" can be introduced into devices optimized for ultra-high-throughput droplet production such as centrifugal (50-52), in-air jetting droplet generators (53), or glass-silicon chips shown to exceed droplet production rates >5.5 billion droplets/minute (39), thus making it feasible to produce spectrally enclosed microbeads on industrial scale.

Terms and Concepts

A number of terms and concepts are discussed below. They are intended to facilitate the understanding of various embodiments of the invention in conjunction with the rest of the present document and the accompanying figures. These terms and concepts may be further clarified and understood based on the accepted conventions in the fields of the present invention, as well as the description provided throughout the present document and/or the accompanying figures. Some other terms can be explicitly or implicitly defined in other sections of this document and in the accompanying figures, and may be used and understood based on the accepted conventions in the fields of the present invention, the description provided throughout the present document and/or the accompanying figures. The terms not explicitly defined can also be defined and understood based on the accepted conventions in the fields of the present invention and interpreted in the context of the present document and/or the accompanying figures.

Unless otherwise dictated by context, singular terms shall include pluralities, and plural terms shall include the singular. Generally, nomenclatures used in connection with, and techniques of, cell and tissue culture, molecular biology, immunology, microbiology, genetics and protein and nucleic acid chemistry are those well-known and commonly used. Known methods and techniques are generally performed according to conventional methods well-known and as described in various general and more specific references, unless otherwise indicated. The nomenclatures used in connection with the laboratory procedures and techniques described in the present disclosure are those well-known and commonly used.

As used herein, the terms "a", "an", and "the" can refer to one or more unless specifically noted otherwise.

The use of the term "or" is used to mean "and/or," unless explicitly indicated to refer to alternatives only, or the alternatives are mutually exclusive, although the disclosure supports a definition that refers to only alternatives and "and/or." As used herein "another" can mean at least a second or more.

The terms "about" and "approximately" as used herein shall generally mean an acceptable degree of error for the quantity measured given the nature or precision of the measurements. Exemplary degrees of error are within 20% (%); preferably, within 10%; and more preferably, within 5% of a given value or range of values. Any reference to "about X" or "approximately X" specifically indicates at least the values X, 0.95X, 0.96X, 0.97X, 0.98X, 0.99X, 1.01X, 1.02X, 1.03X, 1.04X, and 1.05X. Thus, expressions "about X" or "approximately X" are intended to teach and provide written support for a claim limitation of, for example, "0.98X." Alternatively, in biological systems, the terms "about" and "approximately" may mean values that are within an order of magnitude, preferably within 5-fold, and more preferably within 2-fold of a given value. Numerical quantities given herein are approximate unless stated otherwise, meaning that the term "about" or "approximately" can be inferred when not expressly stated. When "about" is applied to the beginning of a numerical range, it applies to both ends of the range.

The term "microbead" and the related terms refer to a particle having one or more dimensions (such as length, width, diameter, or circumference) of about 1000 μm or less, for example, about 500 μm or less, about 100 μm or less, about 50 μm or less, about 10 μm or less, or about 5 μm or less. A microbead may have a generally spherical shape or a non-spherical shape. A microbead may have one or more dimensions (for example, a diameter when a microbead has a generally spherical shape) of from about 1000 μm to about 1 μm, from about 500 μm to about 1 μm, from about 100 μm to about 1 μm, from about 50 μm to about 1 μm, from about 10 μm to about 1 μm, or from about 5 μm to about 1 μm.

The terms "plurality" or "population," when used in connection with microbeads (for example, as in "a plurality of microbeads" or "a population of microbeads"), refer to groups of microbeads (that is, more than one microbead) including various numbers of microbeads. For example, a plurality or a population of microbeads may include 2 or more, 10 or more, 100 or more, 500 or more, $10^3$ or more, $10^4$ or more, $10^5$ or more, $10^6$ or more, or $10^7$, or more microbeads. Each microbead in a plurality or a population of microbeads may have approximately the same one or more dimensions. For example, individual microbeads may have a diameter such that the diameter variation, as measured by coefficient of variance (CV), among all the members of the plurality or a population of microbeads is no greater than about 10%, no greater than about 7%, no greater than about 5%, or no greater than about 1%.

The term "nanoparticle" refers to a particle having at least one dimension (such as length, width, diameter, or circumference) ranging from 1 to 1,000 nm, for example, about 500 nm or less, about 100 nm or less, about 50 nm or less, about 10 nm or less, about 5 nm or less, or about 1 nm or less. For example, a nanoparticle may have one or more dimensions (such as a diameter) of from less than 1000 nm to about 500 nm, from about 500 nm to about 100 nm, from about 100 nm to about 10 nm, from about 50 nm to about 10 nm, from about 10 nm to about 5 nm, or from about 5 nm to about 1 nm. Nanoparticles may have a generally spherical shape or a non-spherical shape.

The term "solution" encompasses colloidal solutions, including emulsions and suspensions. The term "dissolve" and the related terms and expressions encompass forming or producing of colloidal solutions.

The term "lanthanide" refers to elements 57-71 of the periodic table, namely lanthanum (La), cerium (Ce), praseodymium (Pr), neodymium (Nd), promethium (Pm), samarium (Sm), europium (Eu), gadolinium (Gd), terbium (Tb), dysprosium (Dy), holmium (Ho), erbium (Er), thulium (Tm), ytterbium (Yb), and lutetium (Lu). The term "lanthanide" can also refer to combinations of lanthanide elements, compounds containing lanthanide elements or their combinations, or ions containing lanthanide elements or their combinations.

The term "lanthanide nanoparticle" refers to a nanoparticle that includes a lanthanide and a host lattice. Lanthanide nanoparticles are sometimes referred to as "lanthanide nanophosphors."

The term "host lattice" refers to a material that can accommodate the incorporation of lanthanide atoms or ions. When the host lattice is "lanthanide-doped," it means that the host lattice material contains one or more lanthanides. For example, lanthanide dopants may be incorporated into a host lattice to provide lanthanide-doped yttrium orthovanadate ($YVO_4$), lanthanide-doped oxides (for example, doped $ZrO_2$, doped $TiO_2$, doped $BaTiO_3$), lanthanide-doped halides (for example, doped $LaF_3$), lanthanide-doped phosphates (for example, dope $LaPO_4$, doped $LuPO_4$, or doped $YbPO_4$), and lanthanide-doped strontium borates (for example, $SrB_4O_7$, $SrB_6O_{10}$, and $Sr_4B_{14}O_{25}$), among others.

"Lanthanide encoded" or "spectrally encoded" microbeads described in the present disclosure contain lanthanide nanoparticles (Lns) and possess a detectable spectral signature, which is a combination of luminescent signals in the range of 350-850 nm emitted from lanthanide nanoparticles contained in a single microbead upon excitation with an appropriate wavelength of light, for example, UV light (such as 292 nm for excitation of downconverting lanthanides) or IR light (such as 980 nm for excitation of upconverting lanthanides). The luminescence intensity at a characteristic wavelength or wavelengths (for example, 620 nm, 630 nm, or 650 nm) for a particular lanthanide (for example, Eu) indicates the presence and quantity of the particular lanthanide in the source (for example, a microbead) from which the spectral signature originates. A "lanthanide encoded" or "spectrally encoded" microbead may include one or more different types of lanthanide nanoparticles, for example, 2 or more, 3 or more, 4 or more, 5 or more, 6 or more, 7 or more, 8 or more, 9 or more, or 10 or more, wherein each lanthanide nanoparticle has a different luminescence emission spectrum upon excitation. Signals from the combined luminescence spectra make up the spectral signature of a particular microbead, and are mapped to a unique spectral signature code (or "spectral code") during code deconvolution. Lanthanide nanoparticle spectra are typically characterized by narrow emission bands (also referred to as "signals") in the visible region, making one species of material easily distinguishable from another. A lanthanide spectral signature of a microbead can therefore be designed based on the particular identity and relative amounts of lanthanides in the microbead. Lanthanide spectral signatures of microbeads described in the present disclosure can include one or more of an Eu signal, a Dy signal, an Sm signal, a Ce signal, a Tb signal, a La signal, a Pr signal, an Nd signal, a Gd signal, an Ho signal, an Er signal, a Tm signal, a Yb signal, a Pm signal, and a Lu signal.

The term "amino acid" encompasses naturally occurring amino acids as well as non-naturally occurring amino acids, including amino acid analogs and derivatives. Amino acids include naturally occurring proteogenic L-amino acids; D-amino acids; chemically modified amino acids such as amino acid analogs and derivatives; naturally occurring nonproteinogenic amino acids such as norleucine, p-alanine, or ornithine; and chemically synthesized compounds having amino acid characteristics.

The terms "peptide," "polypeptide" or "protein" are used to refer polymer of amino acids linked by native amide bonds and/or non-native amide bonds. Peptides, polypeptides or proteins may include moieties other than amino acids (for example, lipids or sugars). Peptides, polypeptides or proteins may be produced synthetically or by recombinant technology.

The terms "oligonucleotide," "polynucleotide" or "nucleic acid" encompass DNA or RNA molecules, including the molecules produced synthetically or by recombinant technology. Oligonucleotides, polynucleotides or nucleic acids may be single-stranded or double-stranded.

Production of Lanthanide-Encoded Microbeads

Described in the present disclosure and included among the embodiments of the present invention are processes (methods) for producing lanthanide-encoded polymeric microbeads. Processes for producing lanthanide-encoded microbeads described in the present disclosure can also be referred to as methods for microbead production, methods for preparing microbeads, methods for generating microbeads, or by other related phrases. Embodiments of the processes for producing lanthanide-encoded microbeads generate polymeric microbeads comprising lanthanide nanoparticles, which are described in more detail elsewhere in the present disclosure. Polymeric lanthanide-encoded microbeads generated by the processes described in the present disclosure may be described as having a body composed of a polymeric material (which may also be referred to as a "polymer," "polymeric matrix" or "matrix" and include one or more polymeric compounds) with lanthanide nanoparticles dispersed in the polymeric material. It is to be understood that the body and/or the surface polymeric microbeads may also include other components. Processes (methods) for producing polymeric microbeads comprising lanthanide nanoparticles include a step of forming droplets of a fluid comprising a microbead matrix component (which can contain multiple matrix components) and lanthanide nanoparticles (which can be referred to as "a first fluid," "drop-forming fluid" or "dispersed phase") in a second fluid (which can be referred to as "continuous phase"), which is immiscible with the first fluid, and a later step of solidifying the microbead matrix component of the formed droplets, thereby forming the polymeric microbeads comprising lanthanide nanoparticles.

Embodiments of the processes for producing lanthanide-encoded microbeads may use, as starting materials, a mixture containing (comprising) microbead matrix component (which may include multiple components) and lanthanide nanoparticles. Such a mixture may be provided as a fluid. In the context of the present disclosure, the term "providing" is to be construed broadly. The term is not intended to refer exclusively to any particular way of "providing." For example, a fluid comprising a microbead matrix component and lanthanide nanoparticles can be "provided" by preparing it, such as by mixing the fluid's components. The preparation steps of the fluid, which can be the "first fluid" (droplet-forming fluid or dispersed phase) may or may not be included in a method of generating microbeads according to the embodiments of the present invention. A fluid comprising a microbead matrix component and lanthanide nanoparticles can be "provided" a technician, a commercial entity, or a machine prior to the start a method of producing microbeads according to the embodiments of the present invention.

Embodiments of the processes for producing lanthanide-encoded microbeads may utilize, in at least some of the steps, microfluidic devices, which are described in more detail elsewhere in the present disclosure. Some steps of the processes for producing lanthanide-encoded microbeads may be performed within a microfluidic device used for microbead production (that is, performed "on chip"). Some steps of the processes for producing lanthanide-encoded microbeads may be performed outside of a microfluidic device used for microbead production ("off chip"). For example, in some embodiments of the processes for producing lanthanide-encoded polymeric microbeads, the fluid comprising a microbead matrix component and lanthanide nanoparticles ("first fluid") is prepared "off chip" by mixing the microbead matrix component, lanthanide nanoparticles and other components of the fluid (if appropriate) outside of the microfluidics device. The components of the first fluid may be brought together and mixed using a variety of mixing techniques and devices, manual or automated. In one example, the first fluid may be mixed by manually adding components of the first fluid to a vessel, such as a cup or a well of a multi-well plate, and manually pipetting or stirring the first fluid components until a substantially homogenous mixture or solution forms. In another example, the first fluid components may be mixed by an automated stirrer or mixer. In yet another example, the preparation of the first fluid may be fully automated, with the first fluid components delivered to a vessel and mixed by an automated system. One advantage of preparing the first fluid "off chip" that one or more of the first fluids can be prepared and stored ahead of the subsequent steps of the process for producing lanthanide-encoded microbeads.

Processes for producing lanthanide-encoded microbeads according to the embodiments of the present invention may involve contacting the first fluid with another fluid, which can be referred to as a "second fluid" or "continuous phase." The first and the second fluids are immiscible. The first fluid and the second fluid may be contacted in a microfluidics device, and, upon contacting of the first fluid in the second fluid, droplets of the first fluid in the second fluid are formed within the microfluidic device. Droplet formation within the microfluidics device can be accomplished by various droplet generation methods, active or passive. Generally, droplets of the first fluid are formed in a microfluidic device upon deformation of the interface between the first fluid and the second fluid. The interface deformation leading to drop formation can be accomplished by using predetermined geometries of flows of the first fluid and the second fluid within the microfluidic device, such as cross-flowing streams and/or flow focusing, in combination of the flow rates and the properties (such as surface tension and viscosity) of the first fluid (dispersed phase) and the second fluid (continuous phase). In some embodiments of the processes described in the present disclosure, a stream of the first fluid is introduced into of the second fluid at one or more intersections of channels within the microfluidic device. For example, the first fluid may be flowing through a first channel, and be introduced into a stream of second fluid flowing through a second channel at a T-junction of the first channel and the second channel (so-called droplet generation with T-junction), with the droplets of the first fluid being formed in a stream of the second fluid in the channel downstream of the T-junction (which can be referred to as "droplet channel"). In another example, the first fluid may be flowing through a first channel, and be introduced into streams of second fluid flowing from opposing sides of a cross-channel (second channel), with the two streams of the second fluid surrounding the stream of the first fluid and forcing droplet formation into an "output" or "droplet" channel. The above configuration is typically used in a so-called "droplet generation by flow focusing," and can employ one or more flow-focusing components, such as constrictions or flow-focusing nozzles. It is to be understood that the above examples of droplet formation mechanisms are exemplary only and non-limiting, and other ways to generate droplets may be employed. Various ways of microfluidic droplet formation are described, for example, in (59-78). Droplet size may be changed by changing the pressure and/or the flow speed of the first and the second fluids. Droplet size may also change by adjusting the geometry (size and shape), of the microfluidic device channels.

In some embodiments of the processes for producing lanthanide-encoded polymeric microbeads, the formed droplets are removed from the microfluidic device. Accordingly, the processes for producing lanthanide-encoded microbeads according to the embodiments of the present invention may involve a step of removing the formed droplets from the microfluidic device. Removal of the formed droplets from the microfluidic device can be accomplished by the flow of the second fluid with the formed droplets through one or more droplet outlet channels, with the droplets exiting the microfluidics device through one or more droplet outlets. In the embodiments involving removal of the formed droplets from the microfluidics device, microbead matrix component of the formed droplets is solidified outside of the device ("off chip"), thereby forming the polymeric microbeads comprising lanthanide nanoparticles. However, some embodiments of the processes for producing lanthanide-encoded microbeads may not include removal of the formed droplets from the microfluidics device, and solidification of the droplets may be accomplished within the microfluidics device ("on chip"), in which case the polymeric microbeads comprising lanthanide nanoparticles are formed within the microfluidics device and removed from the microfluidics device through appropriate outlet channels and/or outlets.

The step of solidifying the microbead matrix component of the formed droplets may involve various suitable solidification methods and conditions. For example, the microbead matrix component may be a liquid polymer, such as agarose, that solidifies upon exposure to a suitable temperature. In another example, the microbead matrix component may be polymerizable (that is, a polymerizable component), and the step of solidifying the polymerizable component of the formed droplets may involve various suitable polymerization methods and conditions. For instance, some embodiments of the processes for producing lanthanide-encoded microbeads can utilize photo-polymerization, which involves exposing the formed droplets to a light of appropriate wavelength, such as ultraviolet (UV) light. Exposure of the formed droplets to UV light can be performed within the microfluidics device ("on chip") or outside of the microfluidics device ("off chip"). Off-chip UV-polymerization advantageously allows simultaneous irradiation of multiple formed droplets (for example, droplets suspended in the continuous phase collected in a suitable vessel) as a batch, thereby increasing efficiency of the microbead generation process. Another suitable way of polymerization may be thermopolymerization, which involves exposing the formed droplets to suitable temperature. Various chemical polymerization methods may also be used, such as thiol-ene polymerization, redox-initiated polymerization, or controlled radical polymerization. Suitable microbead matrix component solidification processes performed "off chip" increase efficiency of the microbead generation process and allow for simplified designs of the microfluidic devices, which then need not include solidification capabilities.

A microbead matrix component of the first fluid (droplet-forming fluid or dispersed phase) is chosen so that it is compatible with a solidification method used. Other components, such as a cross-linker, a polymerization initiator, or a catalyst may be included in the first fluid and/or the second fluid to accomplish solidification, such as polymerization, by the selected method. For example, when UV-polymerization is used, which involves irradiating the formed droplets with UV radiation to polymerize a polymerizable microbead matrix component, the first fluid may include a photoinitiator. A suitable photoinitiator may include a compound that, when exposed to UV light, undergoes a photoreaction, producing reactive species that are capable of initiating polymerization. Exemplary photoinitiators include, but are not limited to, acetophenones, benzyl and benzoin compounds, benzophenone, cationic photoinitiators, and thioxanthones. In another example, chemical polymerization involving polymerization catalyst may be used to solidify the droplets. For instance, chemical polymerization of acrylamide or acrylamide derivatives (selected as a polymerizable component) may be used, in which case ammonium persulfate (APS) may be included in a first fluid (which is an aqueous dispersed phase in this case), and tetramethylethylenediamine (TEMED) may be included in the second fluid (a hydrophobic continuous phase). TEMED and ammonium persulfate are both polymerization catalysts, with TEM ED diffusing into the first fluid upon contact of the first fluid and the second fluid and accelerating the rate of release of free radicals from APS, which, in turn catalyze the polymerization. In yet one more example, an aqueous agarose with low gelling temperature (<17° C.) may be used as a dispersed phase, with incubation of the formed droplets at the required gelling temperature (which can be performed "off chip") to accomplish solidification of the droplets. In yet one more example, an aqueous solution of sodium alginate is used as a first fluid (a dispersed phase), with the formed droplets exposed to $CaCl_2$ solution (which can be performed "off chip"), at which point Ca' ions react with alginate, thereby forming calcium alginate polymer. In yet one more example, allyl methacrylate is included in the first fluid as a cross-linker when certain acrylate derivatives are used as a polymerizable microbead matrix component.

Polymeric lanthanide-encoded microbeads produced by the processes described in the present disclosure can contain a variety of polymers. Such polymers include, but are not limited to, polyacrylates, polyacrylamides, polymethacrylates, polymethacrylamides, polystyrenes, polythiol-enes, polyurethanes, epoxy resins, polysaccharides (such as agarose), as well as copolymers (for example, random copolymers or block copolymers) or combinations of two or more of the above. Suitable polymers also include polysiloxanes, polyethers (for example, polyethylene glycol (PEG)), polyvinylpyrrolidones, vinyl ethers, vinyl acetates, polyimides, polysulfones, polyamic acids, polyamides, polycarbonates, polyesters, polycacrylamides, and copolymers or combinations of two or more of the above. Accordingly, a microbead matrix component of the first fluid contains compounds, including, but not limited to, polymerizable monomers and/or polymers, that would form suitable solidified polymers or combinations of polymers upon solidification of the droplets formed from the first fluid during processes for producing lanthanide-encoded polymeric microbeads according to the embodiments of the present invention.

The first fluid (droplet-forming fluid or dispersed phase) may be hydrophilic, due to hydrophilic properties of the microbead matrix component and/or to a presence of a hydrophilic solvent, such as water, polar protic solvents, or water-polar protic solvent mixtures. Exemplary polar protic solvents include, but are not limited to, acetic acid, methanol, ethanol, n-propanol, or n-butanol. In some embodiments, the microbead matrix component may, by itself, be a hydrophilic liquid (for example, polyethylene glycol diacrylate 575 (PEGDA 575), acrylic acid, acrylonitrile, methyl acrylate, butyl acrylate, butyl methacrylate, ethyl acrylate, ethylene glycol methyl ether methacrylate, di(ethylene glycol) methyl ether methacrylate, 2-hydroxyethyl methacrylate, ethylene glycol, dimethacrylate, or methacrylic acid). In some other embodiments, the first fluid can be a hydrophilic solution of a microbead matrix component, such as an aqueous solution (an aqueous fluid comprising a microbead matrix component, for example, a polymerizable component). The first fluid (droplet-forming fluid or dispersed phase) comprises at least the microbead matrix component lanthanide and nanoparticles. The first fluid may also comprise or more other components discussed elsewhere in the present disclosure.

In some embodiments, a microbead matrix component may contain one or more suitable branched or linear polyethylene glycol (PEG) derivatives. Some non-limiting exemplary suitable PEG derivatives are PEGDA, PEG diacrylamide (PEGDAM), PEG monoacrylamide-monoamine (PEG-AM) and PEG-monoacrylamide-monoBoc. Such monomers can contain any suitable branched or linear PEG derivative. In some embodiments, the PEG derivative is a linear polymer having a weight average molecular weight ranging from about g/mol to about 10,000 g/mol (for example, about 200 g/mol, about 500 g/mol, about 700 g/mol, about 2000 g/mol, or about 5,000 g/mol). In some embodiments, a microbead matrix component may contain one or more suitable acrylamide derivatives, one or more methacrylamide derivatives, or their combinations. Some non-limiting exemplary acrylamide or methacrylamide derivatives are 2-Acrylamido-2-methyl-1-propanesulfonic acid, 2-Acrylamido-2-methyl-1-propanesulfonic acid sodium salt, 3-(Acrylamido)phenylboronic acid, (3-Acrylamidopropyl)trimethylammonium chloride, 3-O-Acryloyl-1,2:5,6-bis-O-isopropylidene-D-glucofuranose, N-Acryloyl-L-valine, alkylacrylamide, 2-Aminoethylmethacrylamide hydrochloride, N-(3-Aminopropyl)methacrylamide hydrochloride, N-tert-Butylacrylamide, diacetone acrylamide, N,N-Diethylacrylamide, N,N-Diethylmethacrylamide, N,N-Dimethylacrylamide, N-[3-(Dimethylamino)propyl]methacrylamide, N-Ethylacrylamide, N,N'-Hexamethylenebis(methacrylamide), N-Hydroxyethyl acrylamide, (4-Hydroxyphenyl)methacrylamide, 2-Hydroxypropyl methacrylamide, N-(lsobutoxymethyl)acrylamide, methacrylamide, N-(3-Methoxypropyl)acrylamide, N-Phenylacrylamide, N-(Triphenylmethyl)methacrylamide, or N-[Tris(hydroxymethyl)methyl]acrylamide. In some embodiments, a microbead matrix component may contain one or more suitable polysaccharides, such as agarose or alginate.

When the first fluid is hydrophilic, such as aqueous, a hydrophobic fluid immiscible with the first fluid is used as a second fluid (continuous phase) for producing lanthanide-encoded polymeric microbeads according to the embodiments of the present invention. Some non-limiting examples of suitable components of the hydrophobic fluids are oils, such as a mineral oil or a fluorinated oil, liquid hydrocarbons, liquid fatty acids, siloxanes or fluorocarbons. In some embodiments, a hydrophobic second fluid can be a mineral oil comprising a surfactant (for example, Abil EM90 and/or Span 80), dioctyl phthalate comprising a surfactant (for example, Tween 20), oleic acid comprising a surfactant (for example, Tween 20), perfluorinated Fluorinert FC-40 comprising a surfactant (for example, Zonyl® FSO), or octamethyltrisiloxane comprising a surfactant (for example, Triton X-100). A surfactant can be present at a concentration of from about 0.01% to about 5%, v/v or w/w.

The first fluid (droplet-forming fluid or dispersed phase) may be hydrophobic, due to hydrophobic properties of the microbead matrix component, which can, by itself, be a hydrophobic liquid (for example, styrene, acenaphthylene, 4-Bromostyrene, 4-tert-butylstyrene, 4-chlorostyrene, 2,6-dichlorostyrene, 4-methylstyrene, vinylbenzyl chloride, 4-vinylbiphenyl, vinylcyclohexane, 4-vinylphenol, 4-vinyltoluene, polyethylene glycol diacrylate (PEGDA) 200, PEGDA 250, methyl acrylate, methyl methacrylate, ethyl acrylate, 2-ethylhexyl acrylate, acrylonitrile, or vinyl acetate), and/or to a presence of a hydrophobic solvent (for example, an oil, a hydrocarbon, carbon tetrachloride, benzene, toluene, diethyl ether, hexane, or methylene chloride). In some embodiments, the first fluid is hydrophobic fluid comprising a microbead matrix component, lanthanide nanoparticles, and, optionally, one or more other components discussed elsewhere in the present disclosure. Some examples of suitable hydrophobic microbead matrix components are styrene, acenaphthylene, 4-Bromostyrene, 4-tert-butylstyrene, 4-chlorostyrene, 2,6-dichlorostyrene, 4-methylstyrene, vinylbenzyl chloride, 4-vinylbiphenyl, vinylcyclohexane, 4-vinylphenol, 4-Vinyltoluene, PEGDA 200) PEGDA 250, methyl acrylate, methyl methacrylate, ethyl acrylate, 2-ethylhexyl acrylate, acrylonitrile, or vinyl acetate. When the first fluid is hydrophobic, a hydrophilic fluid immiscible with the first fluid is used as a second fluid (continuous phase) for producing lanthanide-encoded polymeric microbeads according to the embodiments of the present invention. For example, a hydrophilic fluid can be an aqueous fluid or a non-aqueous hydrophilic fluid, such as acetic acid, methanol, ethanol, n-propanol, or n-butanol. The hydrophilic fluid used as second fluid (continuous phase) may comprise a surfactant to improve droplet stability, such as Tween-20, Tween-80, Span 80, polyethylene glycol (PEG), Pluronic™ F-68, or Pluronic™ F-127.

As discussed above, the first fluid (droplet-forming fluid or dispersed phase), which can be a hydrophilic (such as aqueous) fluid or a hydrophobic fluid, includes a microbead matrix component, lanthanide nanoparticles, and, optionally, one or more other components. Such optional component included in the first fluid may be compounds aiding in or necessary for solidification, such as polymerization (for example, a cross-linker, a polymerization initiator, such as a photoinitiator, a polymerization catalyst), as discussed elsewhere in the present disclosure. The first fluid may include ferric nanoparticles, which will be then incorporated into the lanthanide-encoded microbeads produced by the embodiments of the processes described in the present disclosure. Polymeric microbeads including ferric nanoparticles are "magnetic," meaning exhibiting movement in magnetic field. As such, the polymeric microbeads including ferric nanoparticles can be magnetically separated, which can be advantageous for various applications described elsewhere in the present disclosure.

Lanthanide nanoparticles included in the lanthanide-encoded polymeric microbeads may be prepared using methods such as those described in (56-58) and (27). As a non-limiting example, one volume of aqueous lanthanide dopant solution (for example, $Sm(NO_3)_3$, $Dy(NO_3)_3$, $Eu(NO_3)_3$; 0.1 M), can be combined with 10-20 volumes of an yttrium salt solution (for example, $Y(NO_3)_3$, 0.1 M) and added portion-wise to an 10-100 additional volumes of osmogent solution (for example, 2000 kDa PEG, 10% w/w), optionally containing a bismuth salt such as $Bi(NO_3)_3$. A solution of matrix material (for example, 10-100 volumes of $Na_3VO_4$, 0.1 M) is added portion-wise prior to microwave heating (for example, at 180° C.) for 5-120 min. Following heating, the resulting white material can be washed and resuspended (for example, in water with optional poly-acrylic acid (1000-2000 kDa; 1-10% v/v)), with our without sonication and/or filtering (for example, through 0.45-μm PTFE filters) filters to obtain the final nanoparticles, 25-250 nm in size (for example, 30-160 nm), as milky white solutions with concentrations ranging from about 5 mg/ml to about 500 mg/ml.

Lanthanide nanoparticles included in the polymeric lanthanide-encoded microbeads may be up-converting or down-converting lanthanide nanoparticles. Suitable up-converting lanthanide nanoparticles may include, for example, $NaGdF_4$:Tm; $NaGdF_4$:Ln; $NaGdF_4$Yb; $NaGdF_4$Er; $NaGdF_4$Yb, Er; $NaYF_4$:Er; $NaYF_4$:Yb; $NaYF_4$:Er,Yb; $NaYF_4$:Tm,Yb; $LaF_3$:Yb,Tm; $LaF_3$:Yb,Er; and $LaF_3$:Yb,Ho nanoparticles. Suitable down-converting lanthanide nanoparticles may include, for example, $YVO_4$:Ln (Ln=Eu,Dy, Sm or Tm nanoparticles). It should be noted that the above referenced lanthanides may be incorporated into the nanoparticles as their respective ions. Materials may be added during preparation of the lanthanide nanoparticles to increase their UV absorption, for downconverters, or IR absorption, for upconverters. For example, in some embodiments bismuth is incorporated into the lanthanide nanoparticles to increase their UV absorption.

Lanthanide nanoparticles included in the polymeric lanthanide-encoded microbeads may be modified (for example, covered or coated) in a suitable material to facilitate formation of a stable colloid solution of the lanthanide nanoparticles in a first fluid (drop forming fluid or dispersed phase). Suitable materials may include materials preventing aggregation of the lanthanide nanoparticles in the first fluid and/or facilitate maintenance of a nanoparticle form of the lanthanide nanoparticles. For example, suitable materials that may be used to cover or coat the lanthanide nanoparticles used a hydrophilic first fluid (drop forming fluid or dispersed phase) may include polyethyleneimine (PEI), polyacrylic acid (PAA), sodium citrate, or citric acid. PAA may be used as a coating material enhance the photostability of the lanthanide nanoparticles, in addition to facilitating stable colloid formation. In another example, lanthanide nanoparticles may be coated with PEGDA 200 or PEGDA 250 to help them form a colloidal solution in a hydrophobic liquid used as first fluid (drop forming fluid or dispersed phase). In one more example, lanthanide nanoparticles may be coated with Poly(propylene carbonate), Poly(ethylene succinate), or Poly(vinyl chloride) carboxylated to help them form a colloidal solution in a hydrophobic first fluid.

Some embodiments of the processes for producing lanthanide-encoded polymeric microbeads advantageously allow for inclusion of reactive (or functional) groups on a surface of the polymeric microbeads during their solidification. In other words, the lanthanide-encoded polymeric microbeads can be functionalized as a part of their production process without adding additional steps after microbead solidification. Functionalization of lanthanide-encoded polymeric microbeads according to the embodiments of the present invention is accomplished by including into a second fluid (continuous phase) used for droplet generation a suitable amphipathic compound capable of covalently bonding with the microbead matrix component during the solidification step. A suitable amphipathic compound includes one or more reactive groups that remain free after covalent binding of the amphipathic compound to the surfaces of the polymeric microbeads, and these free reactive groups can be used for subsequent attachment of molecules or moieties of interest to the microbeads. Molecules of the suitable amphipathic compound included in the continuous phase are driven to and remain at the interface of the continuous phase (second fluid) and dispersed phase (first fluid) after droplet formation, with the hydrophobic parts of the amphipathic molecules facing a hydrophobic fluid (which may be the first or the second fluid), and the hydrophilic parts of the amphipathic molecules facing a hydrophilic fluid (which may be the first or the second fluid). A suitable amphipathic compound or compounds (if more than one is used) are included into the second fluid (continuous phase) at a concentration sufficiently low (for example, from about 0.002% to 2% w/w or v/v) to limit cross-linking of the molecules of the amphipathic compound with the molecules of the microbead matrix component to the surface of the microbeads during their solidification.

As discussed above, an amphipathic compound used for microbead functionalization includes one or more reactive groups that remain free upon the covalent attachment of the amphipathic compound to the surface of the polymeric microbeads during the solidification step of the microbead production process. The reactive (or functional) groups may be used for subsequent covalent coupling of a molecule or moiety of interest. The covalent coupling of a molecule or moiety of interest to the surface of the lanthanide-encoded polymeric microbeads can be termed "derivatization" of the microbeads. Microbead derivatization is discussed in more detail elsewhere in the present disclosure. The reactive (or functional) group can be or comprise a carboxyl group, an amino group, an azide group, a hydroxyl group, a hydrazide group or a chloromethyl group. The polymeric microbeads can be functionalized by two or more different reactive groups during their production by using, for example, an amphipathic compound with two or more reactive groups. In another example, multiple amphipathic compounds with different reactive croups can be added to the continuous phase during droplet generation. Some non-limiting examples of the amphipathic compounds that can be used for microbead functionalization are: for functionalization with carboxyl groups, unsaturated fatty acids, such as 10-undecenoic acid, 4-pentenoic acid, 5-hexenoic acid, 6-heptenoic acid, 7-octenoic acid, 8-nonenoic acid, or 9-decenoic acid; for functionalization with amino groups, amphipathic amines, such as pent-4-enylamine, N-(3-Aminopropyl) methacrylamide, 2-Aminoethyl methacrylate, or N-(2-aminoethyl) methacrylamide; for functionalization with azide groups, 3-azidopropyl acrylate or 3-azidopropyl methacrylate; for functionalization with hydroxyl groups, 4-Penten-1-ol; for functionalization with hydrazide groups, hydrazido acrylate; for functionalization with chloromethyl groups, chloromethyl acrylate.

Production of Functionalized Polymeric Microbeads

Described in the present disclosure and included among the embodiments of the present invention are processes (methods) for producing functionalized polymeric microbeads. Functionalized polymeric lanthanide-encoded microbeads generated by the processes described in the present disclosure may be described as having a body composed of a polymeric material (which may also be referred to as a "polymer," "polymeric matrix" or "matrix" and include one or more polymeric compounds), and a surface, which comprises the microbead polymeric material with covalently bound amphipathic moieties comprising free reactive groups, which can also be referred to as "functional" groups. A reactive (or functional) group can be or comprise a carboxyl group, an amino group, an azide group, a hydroxyl group, a hydrazide group or a chloromethyl group. The processes for producing functionalized polymeric microbeads advantageously allow for inclusion of reactive (or functional) groups on a surface of the polymeric microbeads during their solidification, without requiring additional steps after the solidification.

Processes (methods) for producing functionalized polymeric microbeads according to the embodiments of the present invention include a step of forming droplets of a hydrophilic (such as aqueous) fluid comprising a microbead matrix component (which can contain multiple matrix components) in a hydrophobic second fluid (which can be referred to as "continuous phase"), which is immiscible with the first fluid, and a later step of solidifying the microbead matrix component of the formed droplets, thereby forming the polymeric microbeads. Functionalization of polymeric microbeads according to the embodiments of the present invention is accomplished by including into a hydrophobic second fluid (continuous phase) a suitable amphipathic compound capable of covalently bonding with the microbead matrix component during the solidification step. A suitable amphipathic compound includes one or more reactive groups that remain free and surface-exposed after covalent binding of the amphipathic compound to the surface of the polymeric microbeads during their solidification, and these free reactive groups can be used for subsequent attachment of molecules or moieties of interest to the microbead surface. During solidification of functionalized polymeric microbeads according to the embodiments of the present invention, molecules of a suitable amphipathic compound included in the hydrophobic continuous phase are driven to and remain at the interface of the hydrophobic continuous phase (second fluid) and hydrophilic dispersed phase (first fluid) after droplet formation, with the hydrophobic parts of the amphipathic molecules facing the continuous phase, and the hydrophilic parts of the amphipathic molecules facing the dispersed phase. A suitable amphipathic compound or compounds (if more than one is used) are included into the second fluid (continuous phase) at a concentration sufficiently low (for example, from about 0.002% to 2% w/w or v/v) to limit cross-linking of the molecules of the amphipathic compound with the molecules of the microbead matrix component, so that the molecules of the amphipathic compound are confined to the surface of the microbeads during their solidification.

Embodiments of the processes for producing functionalized microbeads may use, as starting materials, a first fluid containing (comprising) a microbead matrix component (which may include multiple components). As discussed elsewhere in the present disclosure, the term "providing" and the related phase and expressions are not intended to refer exclusively to any particular way of "providing." The first fluid (droplet-forming fluid or dispersed phase) used for production of functionalized microbeads is hydrophilic, which may be due to hydrophilic properties of the microbead matrix component and/or to a presence of a hydrophilic solvent, such as water, polar protic solvents, or water-polar protic solvent mixtures. Exemplary polar protic solvents include, but are not limited to, acetic acid, methanol, ethanol, n-propanol, or n-butanol. In some embodiments, the microbead matrix component may, by itself, be a hydrophilic liquid (for example, polyethylene glycol diacrylate 575 (PEGDA 575), acrylic acid, acrylonitrile, methyl acrylate, butyl acrylate, butyl methacrylate, ethyl acrylate, ethylene glycol methyl ether methacrylate, di(ethylene glycol) methyl ether methacrylate, 2-hydroxyethyl methacrylate, ethylene glycol, dimethacrylate, or methacrylic acid).

In some other embodiments, the first fluid can be a hydrophilic solution of a microbead matrix component, such as an aqueous solution (an aqueous fluid comprising a matrix component, for example, a polymerizable component). In some embodiments, a microbead matrix component may contain one or more suitable branched or linear polyethylene glycol (PEG) derivatives. Some non-limiting exemplary suitable PEG derivatives are PEGDA, PEG diacrylamide (PEGDAM), PEG monoacrylamide-monoamine (PEG-AM) and PEG-monoacrylamide-monoBoc. Such monomers can contain any suitable branched or linear PEG derivative. In some embodiments, the PEG derivative is a linear polymer having a weight average molecular weight ranging from about g/mol to about 10,000 g/mol (for example, about 200 g/mol, about 500 g/mol, about 700 g/mol, about 2000 g/mol, or about 5,000 g/mol). In some embodiments, a microbead matrix component may contain one or more suitable acrylamide derivatives, one or more methacrylamide derivatives, or their combinations. Some non-limiting exemplary acrylamide or methacrylamide derivatives are 2-Acrylamido-2-methyl-1-propanesulfonic acid, 2-Acrylamido-2-methyl-1-propanesulfonic acid sodium salt, 3-(Acrylamido)phenylboronic acid, (3-Acrylamidopropyl)trimethylammonium chloride, 3-O-Acryloyl-1,2:5,6-bis-O-isopropylidene-D-glucofuranose, N-Acryloyl-L-valine, alkylacrylamide, 2-Aminoethylmethacrylamide hydrochloride, N-(3-Aminopropyl)methacrylamide hydrochloride, N-tert-Butylacrylamide, diacetone acrylamide, N,N-Diethylacrylamide, N,N-Diethylmethacrylamide, N,N-Dimethylacrylamide, N-[3-(Dimethylamino)propyl]methacrylamide, N-Ethylacrylamide, N,N'-Hexamethylenebis(methacrylamide), N-Hydroxyethyl acrylamide, (4-Hydroxyphenyl)methacrylamide, 2-Hydroxypropyl methacrylamide, N-(lsobutoxymethyl)acrylamide, methacrylamide, N-(3-Methoxypropyl)acrylamide, N-Phenylacrylamide, N-(Triphenylmethyl)methacrylamide, or N-[Tris(hydroxymethyl)methyl]acrylamide. In some embodiments, a microbead matrix component may contain one or more suitable polysaccharides, such as agarose or alginate. The first fluid may also comprise or more other components discussed elsewhere in the present disclosure, such as, but not limited to, lanthanide nanoparticles or magnetic particles.

Processes for producing functionalized polymeric microbeads according to the embodiments of the present invention may involve contacting the first fluid with a hydrophobic "second fluid" or "continuous phase" comprising an amphipathic compound. The first and the second fluids are immiscible. Some non-limiting examples of suitable components of the hydrophobic continuous phase fluids are oils, such as a mineral oil or a fluorinated oil, liquid hydrocarbons, liquid fatty acids, siloxanes or fluorocarbons. In some embodiments, a hydrophobic second fluid can be a mineral oil comprising a surfactant (for example, Abil EM90 and/or Span 80), dioctyl phthalate comprising a surfactant (for example, Tween 20), oleic acid comprising a surfactant (for example, Tween 20), perfluorinated Fluorinert FC-40 comprising a surfactant (for example, Zonyl® FSO), or octamethyltrisiloxane comprising a surfactant (for example, Triton X-100). A surfactant can be present at a concentration of from about 0.01% to about 5%, v/v or w/w.

Some non-limiting examples of the amphipathic compounds that can be used for microbead functionalization and included in the second fluid are: for functionalization with carboxyl groups, unsaturated fatty acids, such as 10-undecenoic acid, 4-pentenoic acid, 5-hexenoic acid, 6-heptenoic acid, 7-octenoic acid, 8-nonenoic acid, or 9-decenoic acid; for functionalization with amino groups, amphiphathic amines, such as pent-4-enylamine, N-(3-Aminopropyl)methacrylamide, 2-Aminoethyl methacrylate, or N-(2-aminoethyl) methacrylamide; for functionalization with azide groups, 3-azidopropyl acrylate or 3-azidopropyl methacrylate; for functionalization with hydroxyl groups, 4-Penten-1-ol; for functionalization with hydrazide groups, hydrazido acrylate; for functionalization with chloromethyl groups, chloromethyl acrylate. The polymeric microbeads can be functionalized by two or more different reactive groups during their production by using, for example, an amphipathic compound with two or more reactive groups. In another example, multiple amphipathic compounds with different reactive croups can be added to the continuous phase during droplet generation.

The first fluid and the second fluid may be contacted in a microfluidics device, and, upon contacting of the first fluid in the second fluid, droplets of the first fluid in the second fluid are formed within the microfluidic device. Droplet formation within the microfluidics device can be accomplished by various droplet generation methods described elsewhere in the present disclosure. The formed droplets are solidified using various suitable solidification methods and conditions, which are described in more detail elsewhere in the present disclosure. For example, the microbead matrix component may be polymerizable (that is, a polymerizable component), and the step of solidifying the polymerizable component of the formed droplets may involve various suitable polymerization methods and conditions, some of which are discussed elsewhere in the present disclosure. Various suitable components, such as a cross-linker, a polymerization initiator, or a catalyst may be included in the first fluid and/or the second fluid to accomplish solidification, such as polymerization, by the selected solidification method.

Microbeads

Described in the present disclosure and included among the embodiments of the present invention are polymeric microbeads, which may be lanthanide-encoded. Embodiments of the polymeric microbeads may be produced by the processes described in the present disclosure, although the microbeads are not intended to be limited by such production processes. Polymeric microbeads have (comprise) a body composed of a polymeric material (which may be referred to as "matrix" or "polymer" and include more than one polymer). "A body" of a microbead is intended to describe the microbead polymeric material occupying an internal volume of the microbead. Polymeric microbeads can contain various polymers, hydrophobic or hydrophilic, including, but not limited to, polyacrylates, polyacrylamides, polymethacrylates, polymethacrylamides, polystyrenes, polythiol-enes, polyurethanes, epoxy resins, polysaccharides (such as agarose), as well as copolymers (for example, random copolymers or block copolymers) or combinations of two or more of the above. Suitable polymers also include polysiloxanes, polyethers (for example, PEG and PEG derivatives) polyvinylpyrrolidones, vinyl ethers, vinyl acetates, polyimides, polysulfones, polyamic acids, polyamides, polycarbonates, polyesters, polycacrylamides, and copolymers or combinations of two or more of the above. Lanthanide nanoparticles may be dispersed in the polymeric material.

Polymeric microbeads also have (comprise) a surface, which comprises the microbead polymeric material with covalently bound amphipathic moieties comprising free reactive groups, which can also be referred to as "functional" groups. Polymeric microbeads may therefore be referred to as "functionalized." A reactive (or functional) group can be or comprise a carboxyl group, an amino group, an azide group, a hydroxyl group, a hydrazide group or a chloromethyl group. The surfaces of the polymeric microbeads can include two or more different types of covalently bound amphipathic moieties or reactive groups. For example, surfaces of the polymeric microbeads can include amphipathic moieties with two or more different reactive groups. In another example, surfaces of the polymeric microbeads can contain different amphipathic moieties, each amphipathic moiety comprising a different type of a reactive group. Some non-limiting examples of amphipathic moieties bearing reactive groups are: moieties bearing carboxyl groups, such as moieties derived from unsaturated fatty acids, for example, 10-undecenoic acid 4-pentenoic acid, 5-hexenoic acid, 6-heptenoic acid, 7-octenoic acid, 8-nonenoic acid, or 9-decenoic acid; moieties bearing amino groups, such as moieties derived from amphipathic amines, for example, pent-4-enylamine, N-(3-Aminopropyl)methacrylamide, 2-Aminoethyl methacrylate, or N-(2-aminoethyl) methacrylamide; moieties bearing azide groups, such as moieties derived from 3-azidopropyl acrylate or 3-azidopropyl methacrylate; moieties bearing hydroxyl groups, such as moieties derived from 4-Penten-1-ol; moieties bearing hydrazide groups, such as moieties derived from hydrazido acrylate; moieties bearing chloromethyl groups, such as moieties derived from chloromethyl acrylate.

Polymeric microbeads according to the embodiments of the present invention may include lanthanide nanoparticles, which are described elsewhere in the present disclosure. Such polymeric microbeads may be referred to as "lanthanide-encoded" (for example, "lanthanide-encoded functionalized microbeads"). Lanthanide-encoded microbeads may include one or more different types of lanthanide nanoparticles, at different ratios, for example, 2 or more, 3 or more, 4 or more, 5 or more, 6 or more, 7 or more, 8 or more, 9 or more, or 10 or more, wherein each lanthanide nanoparticle has a different luminescence emission spectrum upon excitation. Signals from the combined luminescence spectra of the lanthanide nanoparticles included in the microbeads make up their unique spectral signature or spectral code. Populations of polymeric microbeads, each of which comprises a predetermined spectral signature comprising one or more lanthanide luminescence signals are included among the embodiments of the present invention. A population of polymeric microbeads may have a concentration of lanthanide nanoparticles (or concentrations, if two or more lanthanide nanoparticles are included in the microbeads) that is substantially equal among the polymeric microbeads of the population. In other words, the population of polymeric microbeads may be provided, such that each polymeric microbead in the population has approximately the same ratio of two or more lanthanide nanoparticles as the other polymeric microbeads in the population. In embodiments of microbead populations, a luminescence intensity level variation (as measured by coefficient of variation (CV)) at a defined wavelength among all the members of the population of microbeads is no greater than about 25%, for example, no greater than about 20%, no greater than about 15%, no greater than about 10%, no greater than about 5%, no greater than about 4%, no greater than about 3%, no greater than about 2%, or no greater than about 1%. In some embodiments, the luminescence intensity level variation among all the members of the microbead population is from about 25% to about 1%, for example, from about 20% to about 1%, from about 15% to about 1%, from about 10% to about 1%, from about 5% to about 1%, from about 4% to about 1%, from about 3% to about 1%, or from about 2% to about 1%. In some embodiments of microbead populations, the members of the population have the same with amphipathic moieties comprising free reactive groups bound to the surfaces of all the microbeads in the population.

Some embodiments of the polymeric microbeads according to the embodiments of the present invention may include ferric nanoparticles. Polymeric microbeads including ferric nanoparticles are "magnetic," meaning exhibiting movement in magnetic field, and can be magnetically separated. In some embodiments a functionalized microbead population may include a subpopulation of lanthanide-encoded microbeads with a predetermined spectral signature and a subpopulation of "magnetic" microbeads including ferric nanoparticles. Such a microbead population may be derivatized as described elsewhere in the present disclosure, with the subpopulation of magnetic microbeads separated for analysis subsequent to derivatization.

A set of uniquely identifiable lanthanide-encoded polymeric microbead populations may be provided, and such sets are also included among the embodiments of the present invention. In some embodiments, a set of populations of lanthanide-encoded polymeric microbeads includes 2 or more different populations of lanthanide-encoded polymeric microbeads, for example, 5 or more, 10 or more, 20 or more, 30 or more, 40 or more, 50 or more, 60 or more, 70 or more, 80 or more, 90 or more, or 100 or more different populations of lanthanide-encoded polymeric microbeads. The lanthanide-encoded polymeric microbeads for each population included in a set may include a different spectral code when compared with the lanthanide-encoded polymeric microbeads of the other populations in the set. In some embodiments, the lanthanide-encoded polymeric microbeads of each population included in a set may include the same amphipathic moieties comprising free reactive groups bound to the surfaces of all the microbeads in the population (that is, the same amphipathic moieties throughout the set). In other embodiments, the lanthanide-encoded polymeric microbeads for each population included in a set may include different amphipathic moieties comprising free reactive groups bound to the surfaces of all the microbeads in the population (that is, the same amphipathic moieties throughout each population, but different amphipathic moieties among different populations included in the set).

Microbead Derivatization

Described in the present disclosure and included among the embodiments of the present invention are microfluidic devices for producing derivatized microbeads. Such methods can use, as a starting material, functionalized polymeric microbeads, or their populations, according to the embodiments of the present invention and described elsewhere in the present disclosure. Such functionalized microbeads have a surface which comprises the microbead polymeric material (matrix) with covalently bound amphipathic moieties comprising free reactive groups, which can also be referred to as "functional" groups, such as a carboxyl group, an amino group, an azide group, a hydroxyl group, a hydrazide group or a chloromethyl group. The surfaces of the polymeric microbeads can include two or more different types of covalently bound amphipathic moieties or reactive groups. For example, surfaces of the polymeric microbeads can include amphipathic moieties with two or more different reactive groups. In another example, surfaces of the polymeric microbeads can contain different amphipathic moieties, each amphipathic moiety comprising a different type of a reaction group. When microbeads are used a starting material, a method for producing derivatized microbeads involves includes a step of covalently coupling a molecule or a moiety of interest to one or more reactive groups on microbead surface. Methods for producing derivatized microbeads according to the embodiments of the present invention need not use functionalized microbeads as a starting material. Methods for producing derivatized microbead can include microbead production process steps, as described elsewhere in the present disclosure, and can use, for example, a droplet-forming fluid (dispersed phase), described elsewhere in the present disclosure, as a starting material.

Molecules and moieties of interest that can be covalently coupled to functionalized microbeads are not limited to those specifically listed in the present disclosure. Such molecules and moieties include, but are not limited to, biological non-biological, organic, inorganic, polymeric, monomeric, oligomeric molecules and/or molecules. Some non-limiting examples of such molecules and moieties are amino acids, peptides, proteins, nucleotides, oligonucleotides, nucleic acids, lipids, fluorescent dyes, polysaccharides, or various small molecule compounds, such as drugs. In some exemplary methods for producing derivatized microbeads according to the embodiments of the present invention, a reactive group comprises a carboxyl group, and the method includes a step of covalently coupling an amino-functionalized oligonucleotide to the plurality of the polymeric microbeads. In some exemplary methods for producing derivatized microbeads, a reactive group comprises an amino group, and the method comprises covalently coupling an amino acid, a peptide or a protein to the reactive group. In some exemplary methods for producing derivatized microbeads, a reactive group comprises an amino group, and the method further comprises performing solid-phase peptide synthesis on a surface of the polymeric microbeads. In some exemplary methods for producing derivatized microbeads, a reactive group comprises a hydroxyl groups, and the method further comprises performing cyanogen bromide-activated covalent coupling of an amino acid, a peptide or a protein to the reactive group. In some exemplary methods for producing derivatized microbeads, a reactive group comprises a hydroxyl group, and the method further comprises performing cyanogen bromide-activated covalent coupling of an amino acid, a peptide or a protein to the reactive group. In some exemplary methods for producing derivatized microbeads, a reactive group comprises a chloromethyl group, and the method further comprises performing covalent coupling of an amino acid, a peptide, a protein or other amino-group containing molecule to the reactive group. In some exemplary methods for producing derivatized microbeads, a reactive group comprises an azide group, and the method further comprises performing covalent coupling of a molecule or moiety of interest via click chemistry to the reactive group. In some exemplary methods for producing derivatized microbeads, Different types of molecules or molecules of interest (such as both polypeptides and oligonucleotides) are covalently coupled to the same population of functionalized microbeads that contain multiple different reactive groups on their surfaces.

Devices for Microbead Production

Described in the present disclosure and included among the embodiments of the present invention are devices for producing polymeric microbeads, which can be microfluidic devices. The devices for producing polymeric microbeads according to the embodiments of the present invention can be used to produce polymeric microbeads described in the present disclosure, but are not limited to producing such microbeads or by methods of microbead production described in the present disclosure. It is to be understood that the microfluidic devices for producing polymeric microbeads can be used to produce various types of microbeads by various methods, which may not be described in the present disclosure.

In some embodiments, a microfluidic device comprises: (a) a first inlet port for a first fluid (droplet-forming fluid or dispersed phase, some non-limiting examples of which are described elsewhere in the present disclosure); (b) a second inlet port for a second fluid (continuous phase; examples of which are described elsewhere in the present disclosure); (c) one or more first flow channels fluidically connected with the first inlet port; (d) one or more second flow channels fluidically connected with the second inlet port and intersecting with the one or more first flow channels at one or more intersections configured to provide a stream of droplets of the first fluid in the second fluid in one more droplet channels downstream of one or more intersections; (e) one or more droplet outlets downstream of and fluidically connected to the one or more droplet channels; and (f) one or more droplet outlet channels upstream of and fluidically connected to the one or more droplet outlets, and downstream of and fluidically connected with the one or more droplet channels. In some embodiments, a microfluidic device may comprise more than one first inlet port fluidically connected to one or more first flow channels. In other words, multiple first inlet ports may be fluidically connected to one first flow channel or to multiple first flow channels, for example, each first inlet port fluidically connected to a corresponding first flow channel. In some embodiments, a microfluidic device may comprise more than one second inlet port fluidically connected to one or more second flow channels. In other words, multiple second inlet ports may be fluidically connected to one second flow channel or to multiple second flow channels, for example, each second inlet port fluidically connected to a corresponding second flow channel.

Channels of microfluidic devices according to the embodiments of the present invention can vary in size and shape, depending on their function and other factors, such as a method used to manufacture a microfluidic device. In cross-section, a channel of microfluidic device can have one or more of the following dimensions: a width of from approximately 5 μm to approximately 1000 μm (for example, approximately 5 μm, approximately 10 μm, approximately 50 μm, approximately 100 μm, approximately 150 μm, approximately 200 μm, approximately 250 μm, approximately 300 μm, approximately 350 μm, approximately 400 μm, approximately 450 μm, approximately 500 μm, approximately 550 μm, approximately 600 μm, approximately 650 μm, approximately 700 μm, approximately 750 μm, approximately 800 μm, approximately 850 μm, approximately 900 μm, approximately 950 μm, or approximately 1000 μm); a height from approximately 5 μm to approximately 1000 μm (for example, approximately 5 μm, approximately 10 μm, approximately 50 μm, approximately 100 μm, approximately 150 μm, approximately 200 μm, approximately 250 μm, approximately 300 μm, approximately 350 μm, approximately 400 μm, approximately 450 μm, approximately 500 μm, approximately 550 μm, approximately 600 μm, approximately 650 μm, approximately 700 μm, approximately 750 μm, approximately 800 μm, approximately 850 μm, approximately 900 μm, approximately 950 μm, or approximately 1000 μm); and/or a diameter of from approximately 5 μm to approximately 1000 μm (for example, approximately 5 μm, approximately 10 μm, approximately 50 μm, approximately 100 μm, approximately 150 μm, approximately 200 μm, approximately 250 μm, approximately 300 μm, approximately 350 μm, approximately 400 μm, approximately 450 μm, approximately 500 μm, approximately 550 μm, approximately 600 μm, approximately 650 μm, approximately 700 μm, approximately 750 μm, approximately 800 μm, approximately 850 μm, approximately 900 μm, approximately 950 μm, or approximately 1000 μm). For example, a first flow channel can have a width of from approximately 5 μm to approximately 1000 μm, a height from approximately 5 μm to approximately 1000 μm, and/or a diameter of from approximately 5 μm to approximately 1000 μm. In another example, a second flow channel can have a width of from approximately 5 μm to approximately 1000 μm, a height from approximately 5 μm to approximately 1000 μm, and/or a diameter of from approximately 5 μm to approximately 1000 μm.

In some embodiments, the one or more first flow channels, the one or more second flow channels, the one or more droplet channels and the one or more droplet outlet channels are positioned substantially in the same plane. In some embodiments, the one or more droplet outlet channels may be fluidically connected to the one or more droplet channels by one or more fluidic connections out of the above plane. It is to be understood that the phrases "fluidically connected," "fluidic connection" and other related phrases and expression denote a connection between elements of a microfluidic device that does not necessarily mean a direct physical connection of one element of the microfluidic device to another element. The phrases "fluidically connected," "fluidic connection," etc. denote an ability of a fluid to travel (flow) between one element of the microfluidic device to another element, but intervening elements (such as channels, valves, connections, constrictions, etc.) may be included between the two "fluidically connected" elements.

As discussed above, in the microfluidics devices according to the embodiments of the present invention, the one or more of the first flow channels (that is, the channels for droplet forming or dispersed phase fluid) and the one or more of the second flow channels (that is, the channels for the continuous phase fluid) may intersect at one or more intersections that are configured to provide the stream of droplets of the first fluid in the second fluid. In one example, such an intersection may be a T-junctions of a second channels with a perpendicular first channel, configured to provide droplet generation at the T-junction. In this exemplary configuration, a channel downstream of the T-junction is considered a droplet channel. In another example, an intersection may be a cross-junction of two second channels with a perpendicular first channel, configured to provide droplet generation at the cross-junction by flow focusing. In this exemplary configuration, the first channel may include a flow-focusing element, such as a flow-focusing nozzle, located at the intersection. The channel downstream of the cross-junction collecting the flow of the first fluid from the first flow channel and the second fluid from the opposing side of the two crossing second channels is considered a droplet channel. In some embodiments of the microfluidic device, one or more droplet channels may each bifurcate one or more times (such as 2 or more, 3 or more, 4 or more, 5 or more, 6 or more, etc.) and include a droplet splitter at each bifurcation point. A number of bifurcation points with droplet splitters in a microfluidic device may vary, depending, for example, on the dimensions of the device and/or the initial size of the generated droplets (that is, before droplet splitting) which, in turn, may depend on the dimensions of the first and the second flow channels, the composition of the dispersed and the continuous phases, and/or other conditions. In some a non-limiting example, each of the one or more droplet channels (N=droplet channel number) may include up to 31 bifurcation points with droplet splitters, or up to 31×N bifurcation points with droplet splitters per microfluidic device.

Figure 1B:
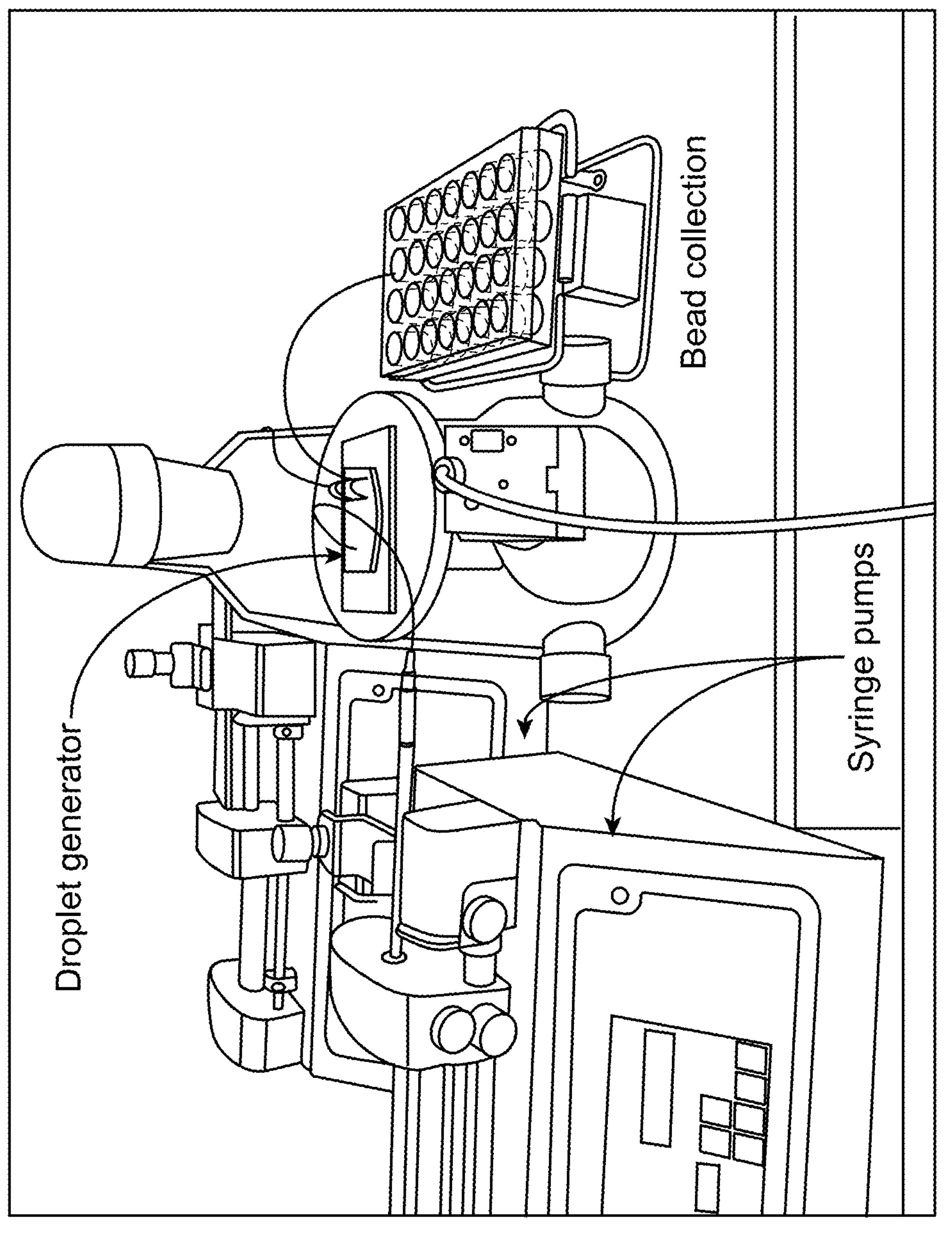
FIG. 1B is a photograph of a laboratory setup for high-throughput microbead production.
Figure 1C:
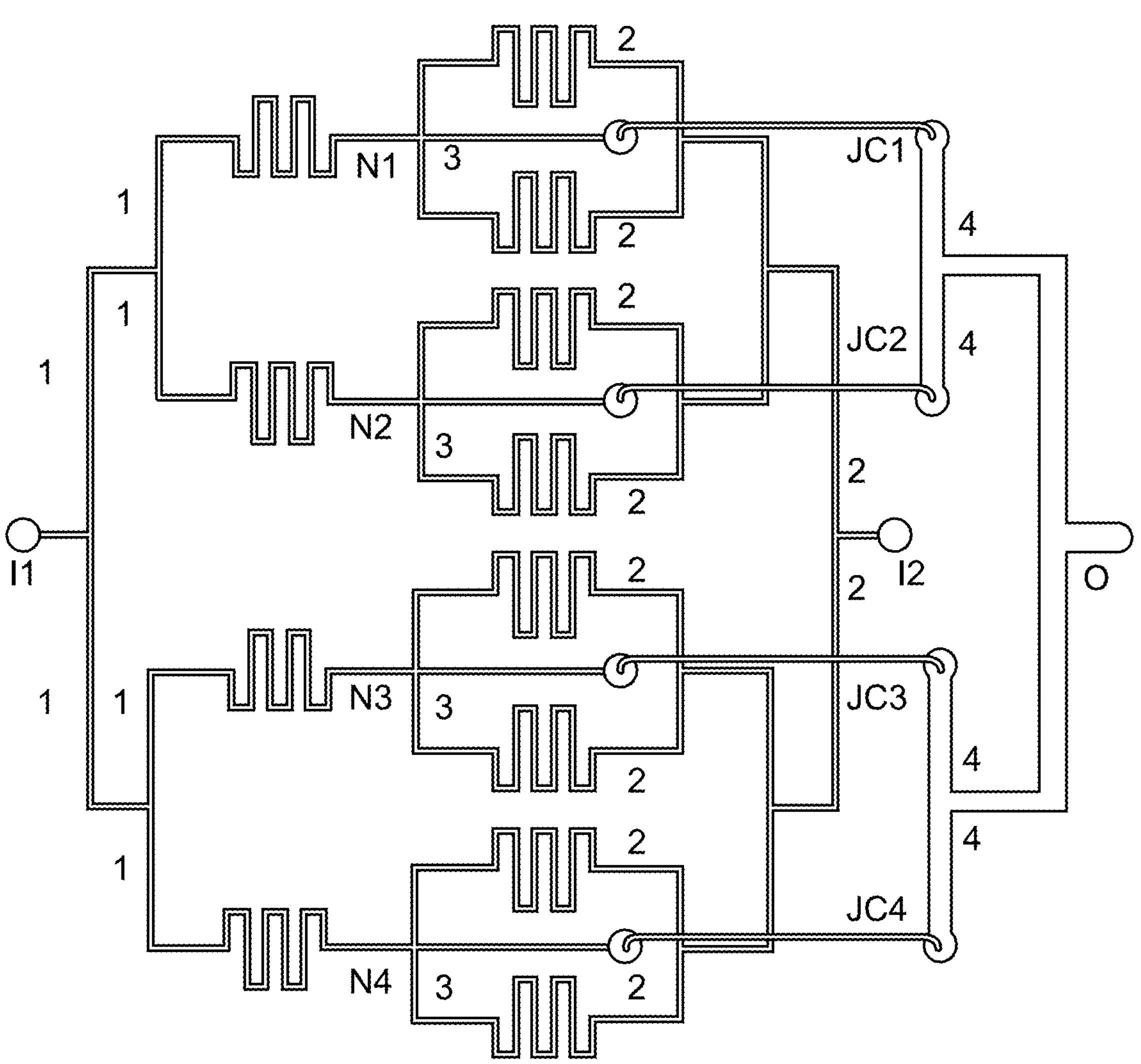
FIG. 1C is a schematic of an exemplary microfluidic device for microbead production. Polymer and oil solutions are introduced, respectively, at inlets 11 and 12 and meet at 4 cross-junctions with flow-focusing nozzles (N1, N2, N3 and N4); produced droplets are routed from 4 droplet channels (3) to droplet outlet channels (4) by out-of-plane fluidic connections (JC1, JC2, JC3 and JC4) prior to collection from the droplet outlet (0).
Figure 5A:
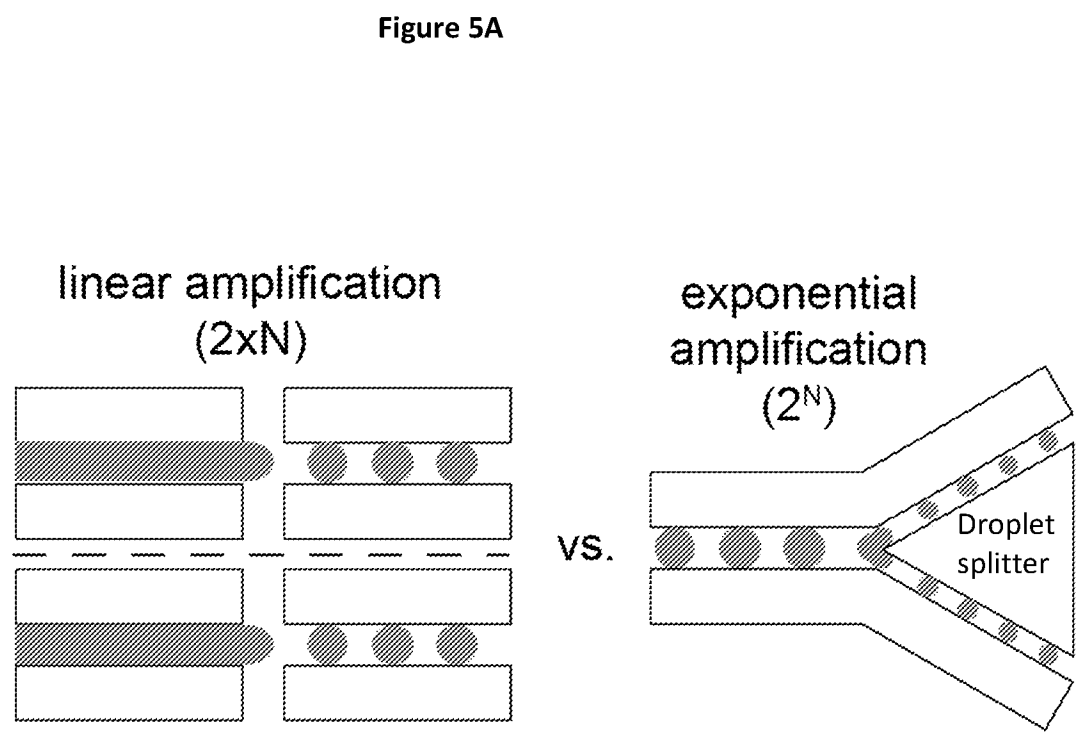
Figure 5B:
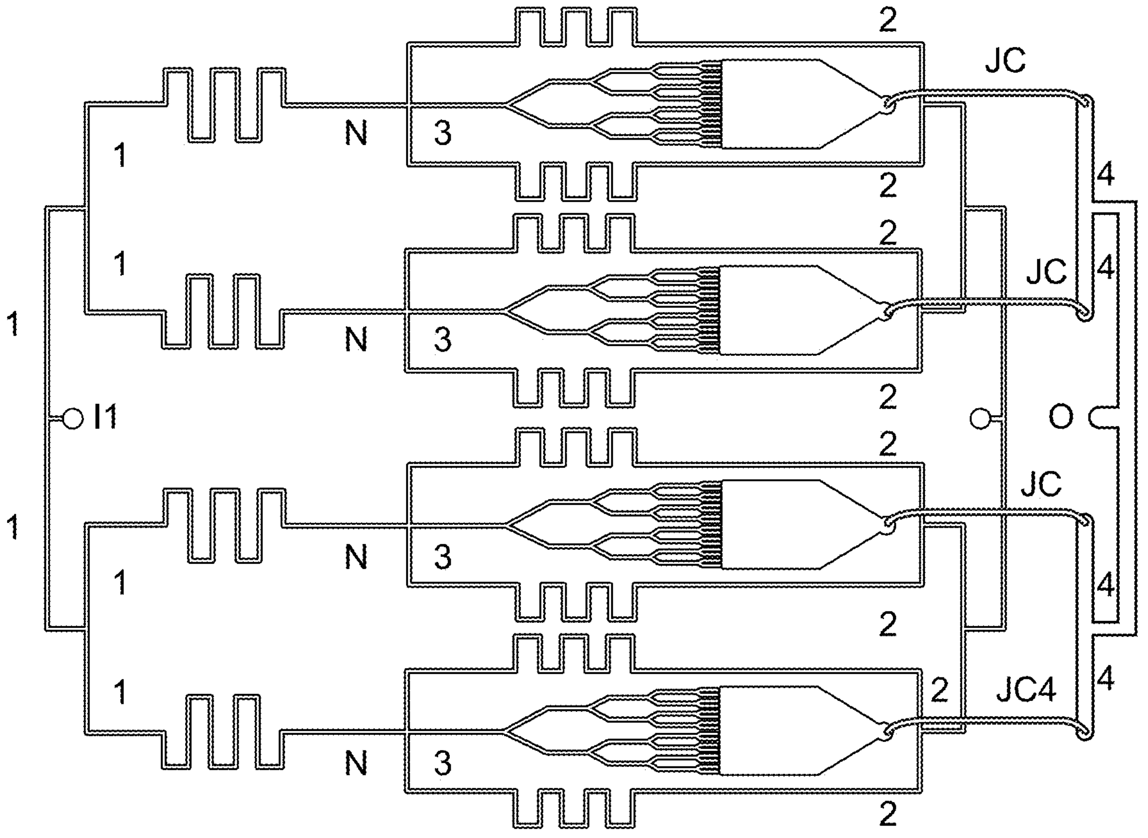
FIG. 5B is a schematic illustration of an exemplary microfluidic device for exponential droplet production and images showing droplet formation at 4 different splitting junctions. Polymer and oil solutions are introduced, respectively, at inlets 11 and 12 and meet at 4 cross-junctions with flow-focusing nozzles (N1, N2, N3, and N44); produced droplets are routed from 4 droplet splitting channels (3) to droplet outlet channels (4) by out-of-plane fluidic connections (JCL JC2, JC3, and JC4) prior to collection from the droplet outlet (0).

FIGS. 1C and 5B schematically illustrate exemplary embodiments of the microfluidic devices described in the present disclosure. In FIGS. 1C and 5B, I1 is a first inlet port for a first fluid (droplet-forming fluid or dispersed phase), I2 is a second inlet port for a second fluid continuous phase). In FIG. 1C, the channels fluidically connected to the first inlet port (first flow channels (1)) split into four first flow channels, and the channels connected to the second inlet port (second flow channels (2)) split into eight second flow channels. The first flow channels and the second flow channels meet at four cross-junctions with flow-focusing nozzles (N1, N3, N3 and N4) at the end of each second flow channel, Each of the four channels downstream of the cross-junctions is a droplet channel (3) collecting the flow of the first fluid from the first flow channel and the second fluid from the opposing side of the two crossing second channels. Four droplet channels (3) are connected to four droplet outlet channels (4) by corresponding four out-of-plane fluidic connections (JCL JC2, JC3 and JC4). Four droplet outlet channels (4) merge into a single droplet outlet channel, which is connected to a droplet outlet (O). FIG. 5B illustrates an embodiment of a microfluidic device in which the droplet channels (3) bifurcate at several points, with droplet splitters (illustrated in FIG. 5A) at each bifurcation point.

In addition to the elements discussed above, microfluidics devices according to the embodiments of the present invention may include various other elements. For example, a microfluidic device may include on-chip resistors that facilitate control of the inputs. These on-chip resistors may be optimized, for example, for stable droplet production at the interface between the first fluid (droplet forming fluid or dispersed phase) and the second fluid (continuous phase). A microfluidic device may include one or more valves, for example, positioned between first and second flow channels of the microfluidic device and their respective inlets. By opening, closing or modulating the one or more valves, fluid communication between the first and the second flow channel and their respective inlets can be controlled. One or more of the valves may be configured for actuation via a variety of mechanisms, such as mechanical, pneumatic, hydraulic, or a combination thereof. In some embodiments, the opening, closing and/or modulation of the valves may be automatically controlled by a suitable electronic control device, such as a computer. Valveless systems may also be utilized for flow control and included in embodiments of microfluidics devices. For example, first and second flow channels may be pressurized to control the flow without the use of valves.

A microfluidic device according to the embodiments of the present invention may be formed using a variety of suitable fabrication methods, such as wet etching, reactive ion etching, machining, photolithography, soft lithography (for example, multi-layer soft lithography), hot embossing, injection molding, laser ablation, in situ construction, or plasma etching. A non-limiting example of a suitable fabrication method utilizing multi-layer soft lithography is provided in Example 1. Selection of a suitable fabrication method depends at least in part on the material to be used in the fabrication. Materials that may be in the fabrication of a microfluidic device include, but are not limited to, silicon, glass, quartz, polydimethylsiloxane (PDMS), polymethylmethacrylate (PMMA), thermoset polyester (TPE), polycarbonate (PC), cyclic olefin copolymer (COC), polystyrene (PS), polyvinylchloride (PVC), and polyethyleneterephthalate glycol (PETG).

Microfluidic devices according to some embodiments of the present invention are manufactured with a portion of the fluidic channels positioned substantially in the same physical plane, meaning the physical plane in which the longest dimensions (lengths) of the above fluidic channels are positioned. The thickness of such physical plane is defined by the approximate height (or diameter) of the above fluidic channels. For example, the thickness of the physical plane, in which a portion of the fluidic channels is located can be from approximately 5 μm to approximately 1000 μm, such as approximately 50 μm). Microfluidic devices according to some embodiments of the present invention also include fluidic connections positioned out of the above-discussed plane. In some embodiments, such out of plane fluidic connections may be constructed from tubing of a suitable material. For example, in some embodiments of the microfluidic devices, droplet channels may be connected to droplet outlet channels or one or more droplet outlets by out of plane fluidic connections constructed from plastic tubing of appropriate diameter and material (for example, polyether ether ketone (PEEK)) and connected outlets of the respective channels fabricated in the microfluidic device. Such out of plane fluidic connection advantageously simplify fabrication of a microfluidic device by circumventing the need for complex fabrication of fluidic channels in several different planes within the microfluidic device.

Systems and Kits for Microbead Production

Described in the present disclosure are systems and kits for producing polymeric microbeads. Systems and kits for producing polymeric microbeads according to the embodiments of the present invention can be used to produce polymeric microbeads described in the present disclosure, but are not limited to producing such microbeads or by methods of microbead production described in the present disclosure. It is to be understood that the systems and kits for producing polymeric microbeads can be used to produce various types of microbeads by various methods, which may not be described in the present disclosure. Various exemplary components of systems and kits for producing polymeric microbeads are described below. It is to be understood that these components may be included in the systems and/or kits separately or in various combinations, such as combinations of two or more, three or more, four or more etc. components.

Embodiments of the systems for producing polymeric microbeads can include a microfluidic device as described elsewhere in the present disclosure and additional elements. For example, a system can include mixing elements, which can be used for "off chip" mixing of the first fluid (droplet-forming fluid or dispersed phase). A variety of mixing elements may be included a system according to the embodiments of the present invention, such as mixers, stirrers etc. In another example, a system can include elements for automating operation of the microfluidic device, such as an automatic controllers, a suitable electronic control device, a computer configured to run a software program for controlling microbead production, etc. In one more example, a system can include a radiation generating element (such as a UV generating element), which can be used for microbead polymerization. In one more example, a system can include a can include a microfluidic device according to the embodiments of the present invention and a droplet connection chamber with a channel used for "on-chip" bead solidification. In one more example, a system can include a microfluidic device according to the embodiments of the present invention and one or more of inlet containers for holding first fluid (droplet-forming or dispersed phase) and/or second fluid (continuous phase). An inlet container, which can be a multi-chamber vessel, may be configured for holding a set of fluids including a different lanthanide nanoparticle or lanthanide nanoparticle combinations. An inlet container included in the system may be configured to fluidically connect with an inlet of the microfluidics device. In one more example, a system can include one or more pumps, such as pneumatic pumps, syringe pumps, rotary pumps etc. A system can include fluidic connections, such as tubing, for example, capillary tubing, to be used in conjunction with the microfluidic device and/or other elements of the system. A system can include various valves and adaptors. A system can include devices for imaging and observation of microbead formation process and/or the formed microbeads, such as microscopes, cameras etc. A system can include a chamber which is purged with a gas, such as nitrogen or argon example, to reduce oxygen contact with droplets and microbeads during their production.

Embodiments of the systems for producing polymeric microbeads can include a microfluidic device as described elsewhere in the present disclosure and various compounds and/or reagents for microbead production. For example, a system can include lanthanide nanoparticles for producing lanthanide-encoded polymeric microbeads, or mixtures of lanthanide nanoparticles. The lanthanide nanoparticles included in the system may comprise at least two types of lanthanide nanoparticles, for example, 2 to 14, 3 to 14, 4 to 14, 5 to 14, or 6 to 14 types of lanthanide nanoparticles, with each lanthanide nanoparticle having a different luminescence spectra. In another example, a system can include ferric nanoparticles for producing magnetic polymeric microbeads. A system can include a fluid to be used for microbead production as a droplet-forming fluid or dispersed phase, which can be hydrophobic or hydrophilic, as described elsewhere in the present disclosure. A system can include a microbead matrix component, such as a polymerizable component, as described elsewhere in the present disclosure. A system can include a fluid to be used for microbead production as a continuous phase, which can be hydrophobic or hydrophilic, as described elsewhere in the present disclosure. A system can include a surfactant, to be used for prevention of droplet merging during microbead production. A system can include one or more amphipathic compounds capable of covalently bonding with the microbead matrix component and including one or more reactive group (such as a carboxyl group, an amino group, an azide group, a hydroxyl group, a hydrazide group or a chloromethyl group) that remains free upon the covalent bonding with the microbead matrix component. Such amphipathic compounds can be used to produce functionalized microbeads, as described elsewhere in the present disclosure.

Embodiments of the kits for producing polymeric microbeads cam include various compounds and/or reagents for microbead production. For example, a kit can include lanthanide nanoparticles for producing lanthanide-encoded polymeric microbeads, or mixtures of lanthanide nanoparticles. The lanthanide nanoparticles included in the kit may comprise at least two types of lanthanide nanoparticles, for example, 2 to 10, 3 to 10, 4 to 10, 5 to 10, 6 to 10, 7 to 10, 8 to 10, or 9 to 10 lanthanide nanoparticles, with each lanthanide nanoparticle having a different luminescence spectra. In another example, a kit can include ferric nanoparticles for producing magnetic polymeric microbeads. A kit can include a fluid to be used for microbead production as a droplet-forming fluid or dispersed phase, which can be hydrophobic or hydrophilic, as described elsewhere in the present disclosure. A kit can include a microbead matrix component, such as a polymerizable component, as described elsewhere in the present disclosure. A kit can include a fluid to be used for microbead production as a continuous phase, which can be hydrophobic or hydrophilic, as described elsewhere in the present disclosure. A kit can include a surfactant, to be used for prevention of droplet merging during microbead production. A kit can include one or more amphipathic compounds capable of covalently bonding with the microbead matrix component and including one or more reactive group (such as a carboxyl group, an amino group, an azide group, a hydroxyl group, a hydrazide group or a chloromethyl group) that remains free upon the covalent bonding with the microbead matrix component. Such amphipathic compounds can be used to produce functionalized microbeads, as described elsewhere in the present disclosure.

EXAMPLES

The following examples are offered to illustrate, but not to limit the claimed invention.

Example 1: Materials and Methods

A. Device Design, Photolithography, and Fabrication

All the microfluidic devices used for microbeads generation were designed and fabricated via standard soft lithography protocols (54). Briefly, microfluidic molding masters were created by: (1) coating 4" test-grade silicon wafers (University Wafer, South Boston, MA) with a single layer of SU-8 2050 negative photoresist, (2) soft baking, (3) exposing this SU-8 layer to UV light passing through a printed transparency mask (designed in AutoCAD (Autodesk)); printed at 50,000 dpi by Fineline Imaging), (4) post-exposure baking, and (5) developing away uncured photoresist using SU-8 developer (Microchem Corp, Newton, MA) according to standard manufacturer's instructions. The molding masters were then used to cast single-layer droplet generators composed of a 1:5 ratio of poly(dimethylsiloxane) crosslinker:base (PDMS, RTV 615, Momentive Performance Materials, Albany, NY). The microfluidic devices were then assembled. For each microfluidic device, four 2.5-cm lengths of PEEK tubing (0.010" ID×0.020" OD) were used. One end of each tube was inserted into the port located in the collection chamber, leaving approximately 2 mm distance between the tube end and the bottom of the chip. The tube was gently bent, and the other end was inserted to the outlet of the corresponding flow focuser. The tube ends were aligned to the equal level by eye to achieve equivalent pressure along each pathway.

IQCrew 40X-200X Science Discovery Series Inverted Microscope with three objectives (4×, 10× and 20×) was used for observation of droplet generation. The 10× eyepiece was replaced by a C-mount 0.5× relay lens (AmScope) to obtain a wider field of view. A USB Thorlab camera (DCC1240M) was installed to simultaneously monitor the droplet generation. Syringe pumps (Pump 11 Elite Infusion Only Single Syringe, Harvard Apparatus) were used as a pressure source for injecting aqueous and oil phases into the microfluidic device. To prevent unwanted polymerization in the aqueous syringe, the flat needle was pulled out and replaced by the PEEK tubing. A small piece of PEEK-Tygon tubing (¼" OD×⅛" ID) combination was inserted into the inlet of the aqueous phase to avoid possible debris clogging during replacement of encoded polymer solution. The microfluidic device was first pressurized with the oil phase at 3200 μL/h. After seeing a small drop of oil coming out of the aqueous inlet, the aqueous phase was inserted, and then the injection was started. The first 1-minute injection of the emulsion was dumped into the waste well in the 24-well plate, and then the collection was started. The target well was prefilled with 80 μL running oil solution to inhibit the interaction between emulsion drop and the plastic bottom. The end of the final outlet was clamped by a 3-way helper and hanged approximately 4 cm above the well. It usually took approximately 10 minutes to use 250 μL of encoded polymer solution. The end of droplet generation, usually being represented by dripping of smaller droplets, was visualized in the orifice region on the screen. The aqueous phase was then unplugged to let the oil back-flow to the aqueous inlet to expel the reminder. The 24-well plate was moved to the waste well to collect the remaining droplets pushed by oil. The aqueous tube with the flat needle was flushed with deionized (DI) water and then dried with air. After that, it was screwed back on to the syringe with the next formula.

TABLE 1

Volumetric rations of Lns master mixtures.

| code | Eu | Dy | Sm | Tm |
|---|---|---|---|---|
| 1 | 1 | 0 | 0 | 0 |
| 2 | 0.91551 | 0 | 0 | 0.08449 |
| 3 | 0.7104 | 0 | 0 | 0.2896 |
| 4 | 0.21248 | 0 | 0 | 0.78752 |
| 5 | 0.89178 | 0 | 0.10822 | 0 |
| 6 | 0.80729 | 0 | 0.10822 | 0.08449 |
| 7 | 0.60218 | 0 | 0.10822 | 0.2896 |
| 8 | 0.10426 | 0 | 0.10822 | 0.78752 |
| 9 | 0.7495 | 0 | 0.2505 | 0 |
| 10 | 0.66501 | 0 | 0.2505 | 0.08449 |
| 11 | 0.4599 | 0 | 0.2505 | 0.2896 |
| 12 | 0.56242 | 0 | 0.43758 | 0 |
| 13 | 0.47793 | 0 | 0.43758 | 0.08449 |
| 14 | 0.27282 | 0 | 0.43758 | 0.2896 |
| 15 | 0.31644 | 0 | 0.68356 | 0 |
| 16 | 0.23195 | 0 | 0.68356 | 0.08449 |
| 17 | 0.02684 | 0 | 0.68356 | 0.2896 |
| 18 | 0.91845 | 0.08155 | 0 | 0 |
| 19 | 0.72704 | 0.08155 | 0 | 0.19141 |
| 20 | 0.26239 | 0.08155 | 0 | 0.65606 |
| 21 | 0.81023 | 0.08155 | 0.10822 | 0 |
| 22 | 0.61882 | 0.08155 | 0.10822 | 0.19141 |
| 23 | 0.15417 | 0.08155 | 0.10822 | 0.65606 |
| 24 | 0.66795 | 0.08155 | 0.2505 | 0 |
| 25 | 0.47654 | 0.08155 | 0.2505 | 0.19141 |
| 26 | 0.01189 | 0.08155 | 0.2505 | 0.65606 |
| 27 | 0.48087 | 0.08155 | 0.43758 | 0 |
| 28 | 0.28946 | 0.08155 | 0.43758 | 0.19141 |
| 29 | 0.23489 | 0.08155 | 0.68356 | 0 |
| 30 | 0.04348 | 0.08155 | 0.68356 | 0.19141 |
| 31 | 0.79939 | 0.20061 | 0 | 0 |
| 32 | 0.45188 | 0.20061 | 0 | 0.34751 |
| 33 | 0.69117 | 0.20061 | 0.10822 | 0 |
| 34 | 0.34366 | 0.20061 | 0.10822 | 0.34751 |
| 35 | 0.54889 | 0.20061 | 0.2505 | 0 |
| 36 | 0.20138 | 0.20061 | 0.2505 | 0.34751 |
| 37 | 0.36181 | 0.20061 | 0.43758 | 0 |
| 38 | 0.0143 | 0.20061 | 0.43758 | 0.34751 |
| 39 | 0.11583 | 0.20061 | 0.68356 | 0 |
| 40 | 0.62555 | 0.37445 | 0 | 0 |
| 41 | 0.05013 | 0.37445 | 0 | 0.57542 |
| 42 | 0.51733 | 0.37445 | 0.10822 | 0 |
| 43 | 0.37505 | 0.37445 | 0.2505 | 0 |

TABLE 1-continued

Volumetric rations of Lns master mixtures.

| code | Eu | Dy | Sm | Tm |
|---|---|---|---|---|
| 44 | 0.18797 | 0.37445 | 0.43758 | 0 |
| 45 | 0.37174 | 0.62826 | 0 | 0 |
| 46 | 0.26352 | 0.62826 | 0.10822 | 0 |
| 47 | 0.12124 | 0.62826 | 0.2505 | 0 |
| 48 | 0.00118 | 0.99882 | 0 | 0 |

B. Microbead Synthesis

Mixtures of PEGDA, Lns, and photoinitiator were prepared largely as described previously (27). In general, premixed formulas were generated by varying ratios of three monomer master mixtures each containing different Lns. All master aqueous mixture contained purified water with 21.4% v/v PEGDA (Sigma-Aldrich, average MW 700) and 5% v/v $YVO_4$:Eu (50 mg/ml). The "Dy", "Sm" and "Tm" master mixtures also contained 21.3% v/v $YVO_4$:Dy (50 mg/ml), 21.3% v/v $YVO_4$:Sm (50 mg/ml) and 21.3% v/v $YVO_4$:Tm (50 mg/ml), respectively. Each encoded polymer solution was prepared using a predetermined volume of one or more master mixtures, as shown in Table 1. 3% v/v solution of photoinitiator lithium phenyl-2,4,6-trimethylbenzoylphosphinate (Sigma-Aldrich, "LAP", 39.2 mg/ml in DI water) was added to each solution right before its injection into the microfluidic device. The droplets were collected through Tygon tubing into a 24-well plate (Thermo Fisher Scientific). To prevent premature evaporation of HFE7500 and resultant droplet breakage during initial droplet production, each well contained approximately 80 ρL of oil solution. 2-minute flood UV (IntelliRay, UV0338) at 100% amplitude was applied to the plate to induce the polymerization in every two formulas. Microbeads were washed with dimethylformamide (Thermo Fisher Scientific), dichloromethane (Thermo Fisher Scientific) and methanol (Thermo Fisher Scientific), and then resuspended in 1 ml 1× phosphate buffered saline (PBS) (Thermo Fisher Scientific) with 0.01% (v/v) Tween-20 (Sigma-Aldrich) (PBST) or dimethyl sulfoxide (DMSO, Thermo Fisher Scientific) for further use. For producing magnetic microbeads, 10% v/v $Fe_3O_4$ nanoparticle solution (150 mg/ml) was added to each recipe.

C. Lanthanide Nanoparticle Synthesis

The synthesis of lanthanide nanoparticles (Lns) was performed substantially as described in (18). All chemical reagents and poly(acrylic acid) sodium (NaPAA), and 45 wt % water solution for lanthanide nanoparticle synthesis were purchased from Sigma-Aldrich (St. Louis, MO) and were used without further purification. Microwave synthesis was performed using a Biotage Initiator (Biotage AB, Uppsala, Sweden). Purification of the synthesized lanthanide nanoparticles was performed by ultrafiltration using Amicon Ultra-15 centrifugal filter units with a 30,000 MWCO (Millipore, Billerica, MA), resulting in a colloid solution with a lanthanide nanoparticle concentration of approximately 50 mg/ml in water. Dynamic light scattering measurements established that produced Lns occupied a narrow size distribution (approximately 100-nm in diameter), with observed excitation spectra consistent with prior measurements.

D. Magnetic Nanoparticle Synthesis

Magnetic nanoparticles were synthesized based on the co-precipitation and thermal decomposition methods. 6 ml of $FeCl_2 \cdot 4H_2O$ (Sigma-Aldrich, 1 M in DI water, filtered) was added to the mixture of 9 ml NaPAA (45 wt % water solution), 1.011 g $KNO_3$ (Sigma-Aldrich) and 28.931 ml DI water. The reaction tube was incubated in a water bath preheated to 100° C. and stirred with medium speed. After the addition of Fe' solution, 2.069 ml $NH_3H_2O$ (Sigma-Aldrich, 30-33% $NH_3$ in $H_2O$) was immediately added and then a black precipitation was observed simultaneously. The whole reaction was carried on at 100° C. for 2 hours. Then the slurry was transferred to a 50-ml falcon tube and centrifuged at 4000 rpm for 10 min. The supernatant was kept for the further filtration, which was performed by ultrafiltration using Amicon Ultra-15 centrifugal filter units with a 30,000 MWCO to wash away any remaining NaPAA by DI water. The final product was suspended in approximately 3 ml DI water with a concentration of approximately 150 mg/ml.

E. Dynamic Light Scattering (DLS)

The DLS (Brookhaven Instrument Nanobrook Omni) was performed for all the Lns solutions and magnetic nanoparticles. The Lns solution was diluted 40× and filled ⅓ of the cube while the dilution factor for magnetic nanoparticles was 100×. The cube was inserted into the measurement chamber for characterization.

F. Oligonucleotide Conjugation

To prepare for oligonucleotide conjugation, microbeads were washed and resuspended in dimethyl sulfoxide (DMSO). The conjugation reaction was assembled by addition of 20 μl 1-ethyl-3-(3-dimethylaminopropyl)carbodiimide (EDC) from a 300 mM stock solution prepared by dissolving 58 mg EDC in 1 ml of DMSO, 20 μl 1-hydroxy-7-azabenzotriazole (HOAT) from a 60 mM solution prepared by dissolving 9.2 mg of HOAT in 1 ml of DMSO, and 20 μl diisopropylethylamine (DIPEA) from a 300 mM solution prepared by adding 32 μl DIPEA to 968 μl DMSO. Microbeads were incubated in this EDC, HOAT, and DIPEA solution for 15 minutes on a shaker (or rotator) for mixing. After 15 minutes, 10 μl (from 100 μM stock solution) of oligonucleotides modified at 5' end with amines and a carbon spacer (the "5AmMC12" modification from Integrated DNA Technologies) were added, as well as an additional 20 μl each of EDC, HOAT, and DIPEA (55). An oligonucleotide modified at the 3' end with an Alexa 647 dye was used to facilitate imaging-based measurement of oligonucleotide conjugation to microbeads. The reaction was incubated at room temperature for 16 hours on a shaker. After this incubation, the conjugation reaction was neutralized by adding 50 μl of 500 mM ethanolamine solution to each reaction and incubating the reaction for 1 hour. The ethanolamine solution was prepared by adding 30.2 μl ethanolamine to 968 μl DMSO. Following conjugation, the microbeads were washed with PBS containing 0.1% (v/v) Tween 20. The microbeads were finally resuspended in PBS with 0.1% (v/v) Tween 20 and stored at 4° C.

G. Aqueous 1-Ethyl-3-(3-dimethylaminopropyl)carbodiimide (EDC) chemistry

For streptavidin-coated microbeads, 150 μL of carboxy-microbeads were washed and resuspended in 200 μL of MES buffer supplemented with 0.01% (v/v) Tween 20. Next, 200 μL of freshly made 1-Ethyl-3-(3-dimethylaminopropyl)carbodiimide (EDC, Sigma-Aldrich) solution 2% w/v (corresponds to 10 mg EDC in 500 μL MES buffer) was added into the microbead suspension, and the suspension was then incubated for 3.5 hours at room temperature on a rotator. The O-acylisourea intermediate formed on the microbeads is unstable in aqueous solutions, thus, after the incubation, the microbead suspension was immediately resuspended in 400 μL of borate buffer supplemented with 0.01% (v/v) Tween 20. To conjugate streptavidin, 16 μL of 1 mg/ml streptavidin (Sigma-Aldrich) in borate buffer was added into the suspension, and the whole slurry was incubated overnight on the rotator at 4° C. After the overnight incubation, the reaction was quenched by adding 10 μL of 0.25 M ethanolamine in borate buffer, followed by incubation on a rotator for 30 minutes at 4° C. The final product was washed and resuspended in PBST buffer for further use. The microbeads were stored at 4° C. for up to approximately 6 months without loss of streptavidin binding efficiency.

H. Biotinylation of $NH_2$-Microbeads

Microbeads coated with amine groups using 0.09% (v/v) pent-4-enylamine were stored in PBST and extensively washed with dichloromethane (DCM), methanol and dimethylformamide (DMF) prior to biotin conjugation. Approximately 10,000 microbeads were conjugated twice overnight, by incubation on a rotator at room temperature with 39 mg biotin, 24 μl N,N'-ciisopropylcarbodiimide (DIC) and 56 μl DIPEA. The microbeads were then washed with DMF, methanol, DCM, DMF, water and PBST. Approximately 2,000 microbeads were passivated with 5% BSA PBST for one hour at room temperature. The 5% BSA PBST solution was exchanged to 2% BSA in PBST. and 1 μl of 1 mg/ml streptavidin was added. The suspension was then incubated for 30 min at 4° C. The biotinylated streptavidin-bound microbeads were washed 3 times with PBS-T and imaged.

I. Microbead Imaging and Data Analysis

Microbead imaging was performed on a Nikon Ti microscope with a custom UV transilluminator largely as described in (28). Briefly, lanthanide emission was detected through 9 emission filters (435/40, 474/10, 536/40, 546/6, 572/15, 620/14, 630/92, 650/13, and 780/20 nm) and recorded on an sCMOS camera (Andor) (Andor Technology plc., Belfast, Northern Ireland). Linear unmixing was performed to extract all the lanthanide ratios using custom software. The binding of DNA oligonucleotides, streptavidin and biotin was visualized through filter Cy5, EGFP and Cy5.

Example 2: High-Throughput Microbead Production

High-throughput microbead production was implemented using two syringe pumps, a low-cost microscope, a flood UV illumination source, and an easily fabricated single-layer microfluidic device. To allow for parallel microfluidic droplet generation, the device used PEEK tubing as out-of-plane fluidic connections to provide three-dimensional routing of flow without a need for complex multilayer PDMS device fabrication or laser ablation to create connections between layers, as described, for example, in (31). Three stages of microbead production are illustrated in FIG. 1A: (1) off-chip generation of polymer/Lns mixtures ('polymer mixing'), (2) on-chip production of polymer/Lns droplets using parallel microfluidic flow focusers ('droplet production'), and (3) off-chip polymerization of polymer/lanthanide droplets into solid microbeads via exposure to UV light ('microbead polymerization').

Figure 1D:
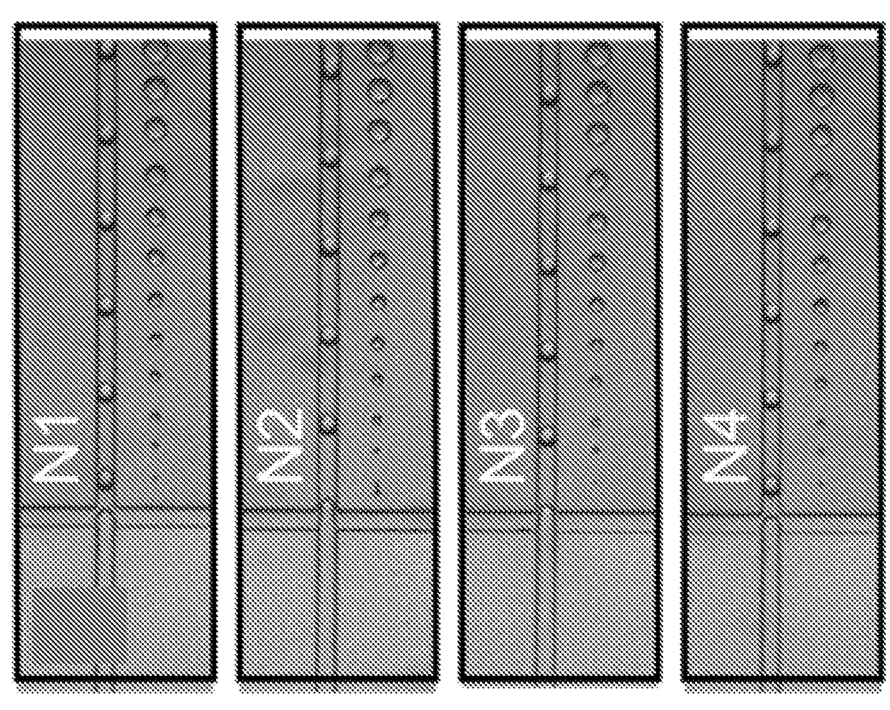
FIG. 1D are representative microphotographic images of droplet generation at 4 flow-focusing nozzles (N1-4).
Figure 1E:
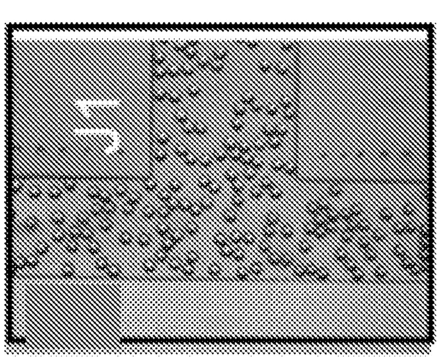
FIG. 1E are representative microphotographic images of droplets at junctions J1 and J2 after passing through out-of-plane fluidic connections into outlet channels.
Figure 1E:
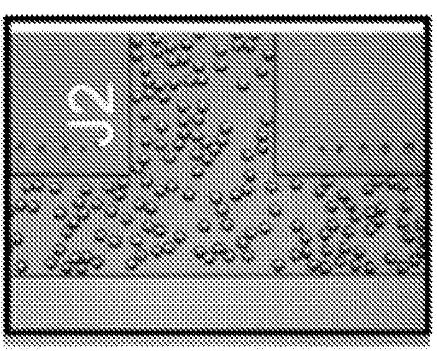

During stage 1, ('polymer mixing'), ratiometric mixtures of Lns (typically 24, 48, or 96 distinct mixtures each corresponding to a unique spectral code) were combined with a polymer solution off-chip via manual or robotic pipetting and deposited into a standard multi-well plate, thus generating a set of "encoded polymer solutions." Encoded polymer solutions were stored at 4° C. in the dark for up to several weeks prior to droplet production. Immediately before stage 2 ('droplet production'), a UV-activated photoinitiator lithium phenyl-2,4,6-trimethylbenzoylphosphinate (LAP) was added to each encoded polymer solution to facilitate subsequent off-chip microbead polymerization. In the second stage ('droplet production'), an encoded polymer solution and a fluorinated oil solution (HFE7500+2% w/w Ionic Krytox surfactant) were simultaneously introduced into a microfluidic droplet generator using syringe pumps at specific volumetric flow rates (FIG. 1B). Within the device, the aqueous polymer and fluorinated oil streams (FIG. 1C, $I_A$ and $I_O$ for aqueous and oil inlets, respectively) met at 4 parallel droplet generation nozzles (FIG. 1C, N1-N4), where changes in interfacial tension caused the aqueous polymer to break off and form monodisperse droplets within the oil stream (FIG. 1D). Out-of-plane fluidic connection (FIG. 1C, JC1-4) routed droplets produced at each nozzle to 2 junctions (FIG. 1C, J1 and J2; FIG. 1E) and subsequently to a single output (FIG. 1C, O), enhancing production rates 4-fold while allowing collection of all droplets containing a given code within a single well of the 24-well plate. It was possible to change droplet size by changing the flow rates of aqueous and oil stream. For example, flow rates of 600 μl/hour (aqueous stream) and 3200 μl/hour (oil stream), respectively, stably generated droplets with a measured median diameter of approximately 52 μm and an overall coefficient of variation (CV) of 2% (FIG. 1F). Between different encoded polymer solution, the entire device was flushed with oil, and aqueous stream tubing was subsequently flushed with water to prevent cross-contamination. In the stage 3 ('microbead polymerization'), the droplets generated from a given encoded polymer solution were transferred to a single well of a multiwell plate, and the entire multiwell plate was exposed to flood-UV illumination, allowing for simultaneous polymerization of all the collected droplets into solid microbeads.

Figure 2A:
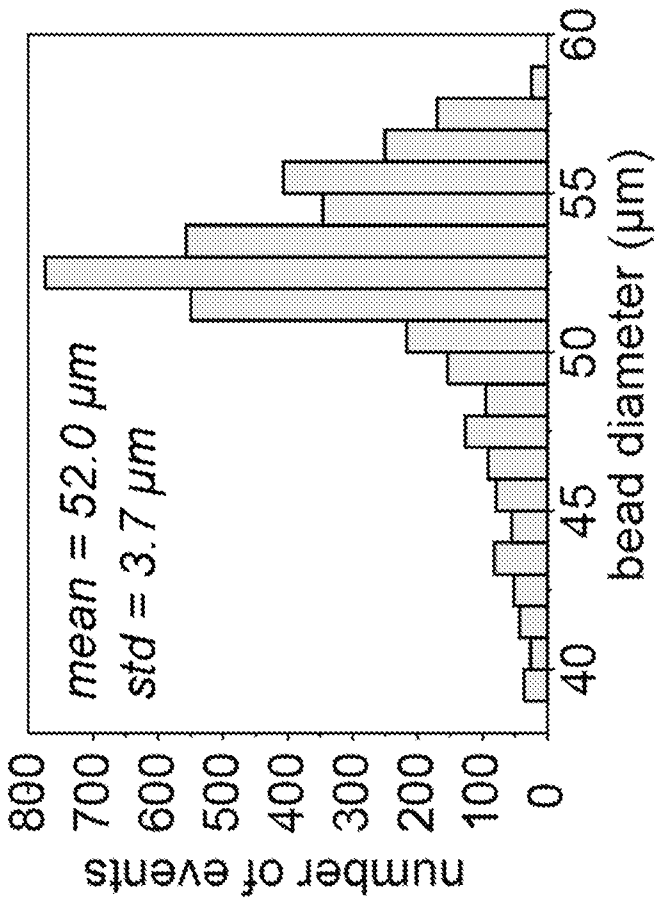
FIG. 2A is a histogram showing measured diameters for produced microbeads (diameter =52.0+/−3.7 μm, CV=7%, 4138 microbeads).

The above process typically produced approximately 3,000,000 microbeads per 20 min, enhancing throughput by over 1000-fold, as compared to previously described production methods (see, for example, (27)). Polymerized microbeads remained highly monodisperse, with a measured median diameter of 52 μm and an overall CV of 7%, when produced at flow rates of 600 μl/hour (aqueous stream) and 3200 μl/hour (oil stream) (FIG. 2A). The microbeads were fully polymerized, with size distributions similar to those of the initial droplets. The calculated CV was slightly higher than that observed with previously described lower-throughput production methods (7% vs 5%, respectively) (27, 28), likely due to a combination of oxygen inhibition and overheating inducing droplet merging and breakage during off-chip polymerization. The CV can be further minimized by subsequent data filtering, as described in (32). However, the benefits associated with enhanced throughput likely outweigh a small increase in CV for all but the most sensitive applications.

Example 3: Easily Distinguishable Microbead Spectral Codes

Using microbeads in multiplexed assays requires the ability to distinguish microbead-embedded codes from one another with high confidence. To test the robustness of spectral encoding and determine the maximum likely coding capacity achievable with high-throughput production described in Example 2, a target matrix of 48 distinct spectral codes was designed. The spectral codes were comprised of different ratios of Dysprosium (Dy), Samarium (Sm), Thulium (Tm), and Europium (Eu) Lns (Dy/Eu, Sm/Eu, and Tm/Eu). Different ratios of Lns were mixed off-chip by manual pipetting, the microbeads were produced from each mixture substantially as described in Example 1, and the resulting microbeads were washed extensively with solvents to remove unpolymerized material. The resulting microbeads were imaged to quantify observed Lns signal intensity ratios and compare these measured ratios to the desired target ratios.

Figure 2B:
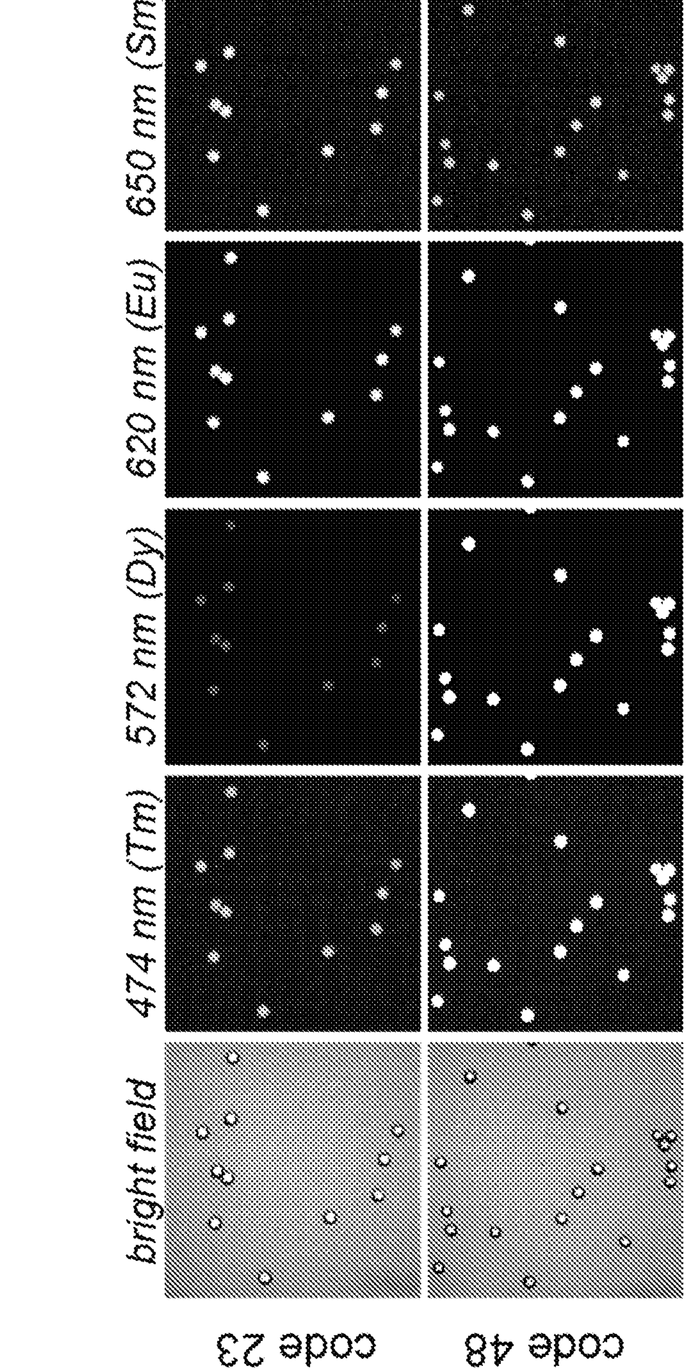
FIG. 2B are representative bright field and lanthanide emission images of microbeads for 2 different spectral codes (23 and 48).

The images of microbeads excited in the deep UV (292 nm) with emission collected across 9 Lns emission channels (435, 474, 536, 546, 572, 620, 630, 650, and 780 nm) established that microbeads were homogeneously polymerized after UV flood exposure without detectable Lns aggregation (FIG. 2B). In contrast, dramatic aggregation of Lns was observed when the previously reported in (27) 'on-chip' formula was used, which had twice the poly(ethylene glycol) diacrylate (PEGDA) concentration in the polymer solution. While not wishing to be bound by the following hypothesis, the following explanation of the observed differences in aggregation is suggested. The Lns are wrapped by poly-acrylic acid, the hydrolysis of which generates negatively charged, repellent forces in water to prevent aggregation of Lns. As PEGDA also absorbs water molecules to dissolve, the solubility conflict between Lns and higher amount of PEGDA may abolish the homogeneous suspension of negative charged Lns, yielding aggregation of Lns after microbead polymerization.

Figure 2C:
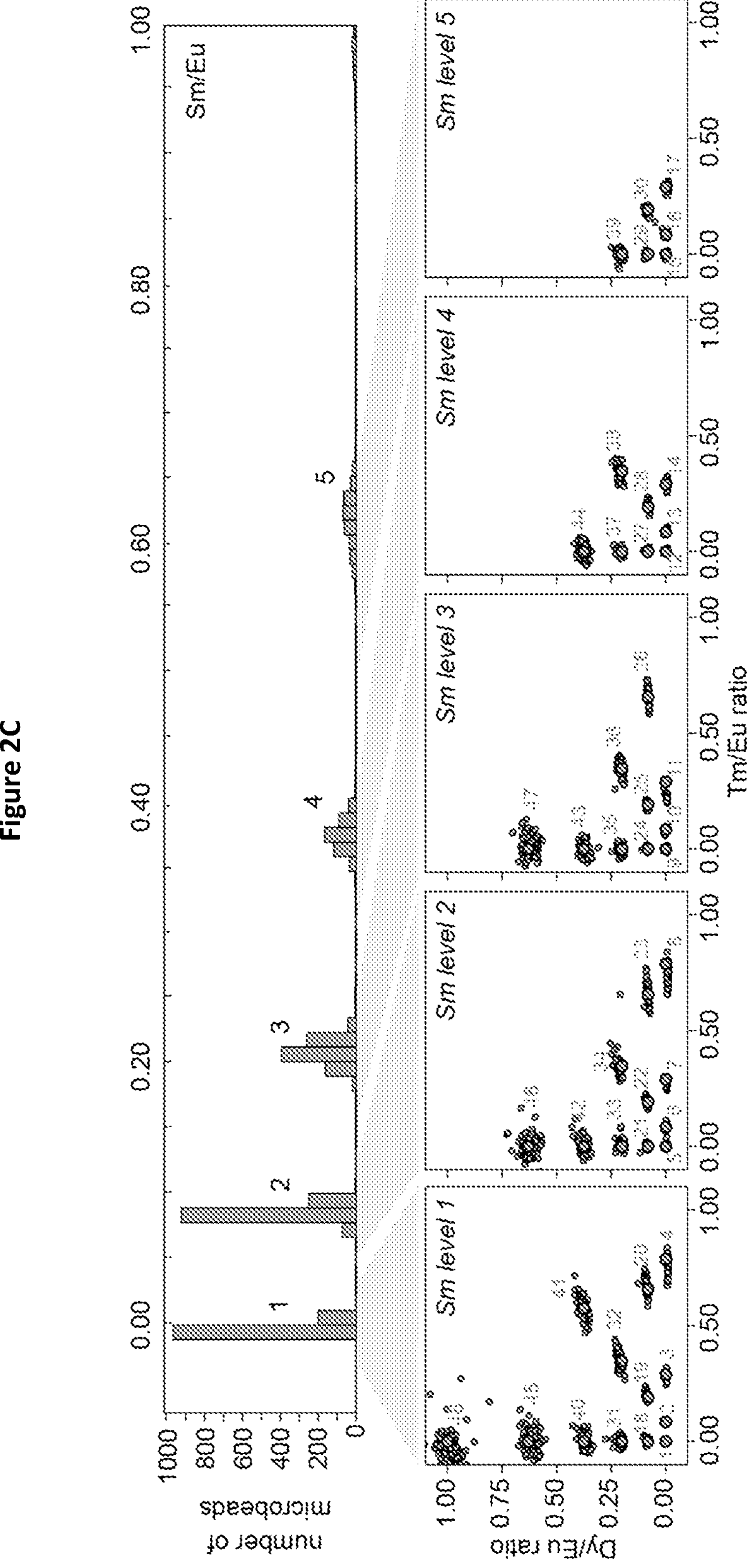
FIG. 2C is a histogram of Sm microbead intensities (top) and scatter plots showing measured Dy/Eu and Tm/Eu ratios for each Sm intensity level (bottom) for 48 code clusters.
Figure 2D:
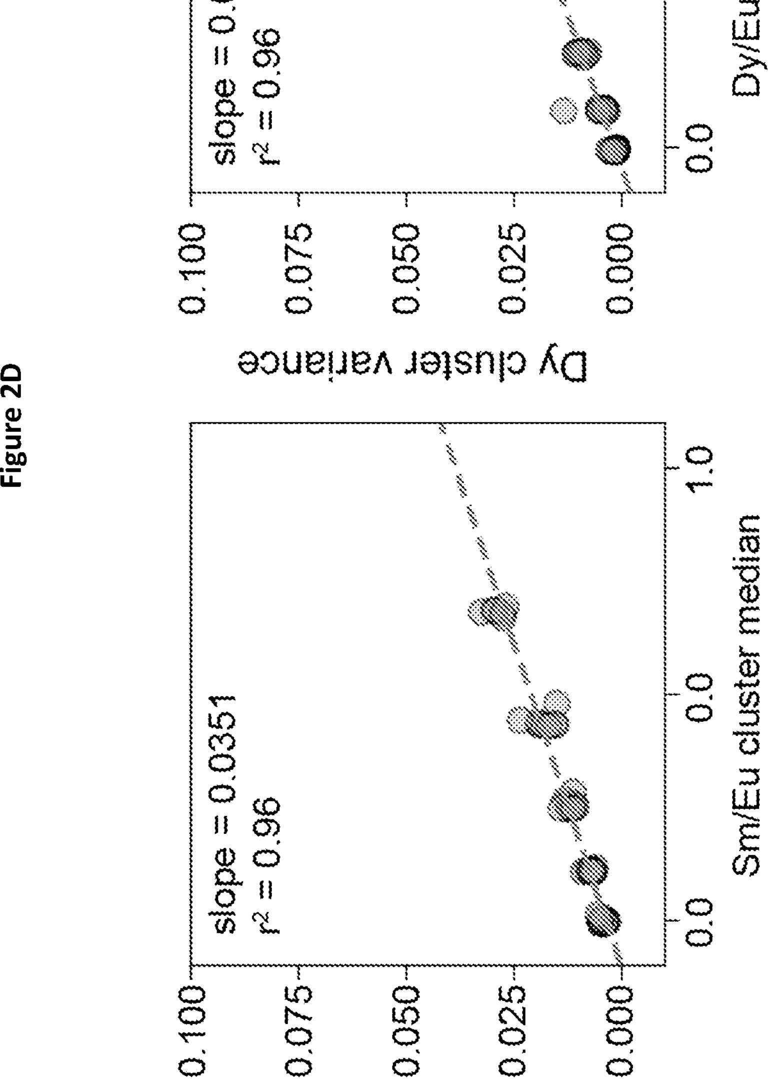
FIG. 2D are plots illustrating Sm/Eu (left) and Dy/Eu (right) cluster variance as a function of cluster median.
Figure 2E:
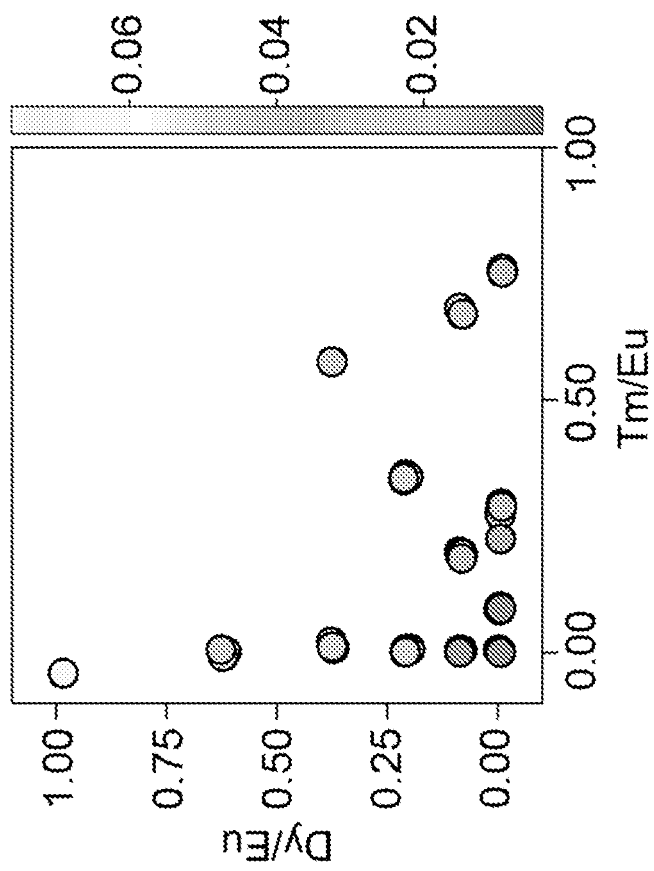
FIG. 2E is a plot illustrating Tm cluster variance as a function of Dy/Eu and Tm/Eu cluster median.

Previously, it was observed (see, for example, (27) and (28)) that emission spectra for Sm are largely orthogonal to those of other Lns, such that observed Sm/Eu intensities depend only on the amount of Sm incorporated within each microbead. Consistent with the prior observations, five clearly separable Sm/Eu ratios were observed for the microbeads used in the present experiments. The observed ratios corresponded directly to the intended Sm/Eu target levels (FIG. 2C, top). By considering only the microbeads at a given Sm/Eu ratio and plotting the observed Dy/Eu ratio against the observed Tm/Eu ratio for each microbead, it was possible to directly visualize individual code clusters and compare each cluster to its intended target value (FIG. 2C, bottom). All 48 code clusters were present and easily distinguished from one another with the median observed cluster intensity ratio well-centered on the desired target. For Sm/Eu and Dy/Eu ratios, the observed cluster variance depended linearly on the median Sm/Eu or Dy/Eu ratio, respectively (FIG. 2D), with a slope of approximately 0.04 for both Lns. By contrast, the variance for clusters in the Tm/Eu channel depended on both the median Tm/Eu and Dy/Eu ratios (FIG. 2E), reflecting the fact that Dy and Tm both emit light in the 474 nm emission channel, contributing to crosstalk. With the measured cluster variance, it is possible to distinguish an anticipated 208 code set comprised of Sm, Dy, Tm and Eu.

Example 4: Microbead Functionalization During Polymerization

Figure 3A:
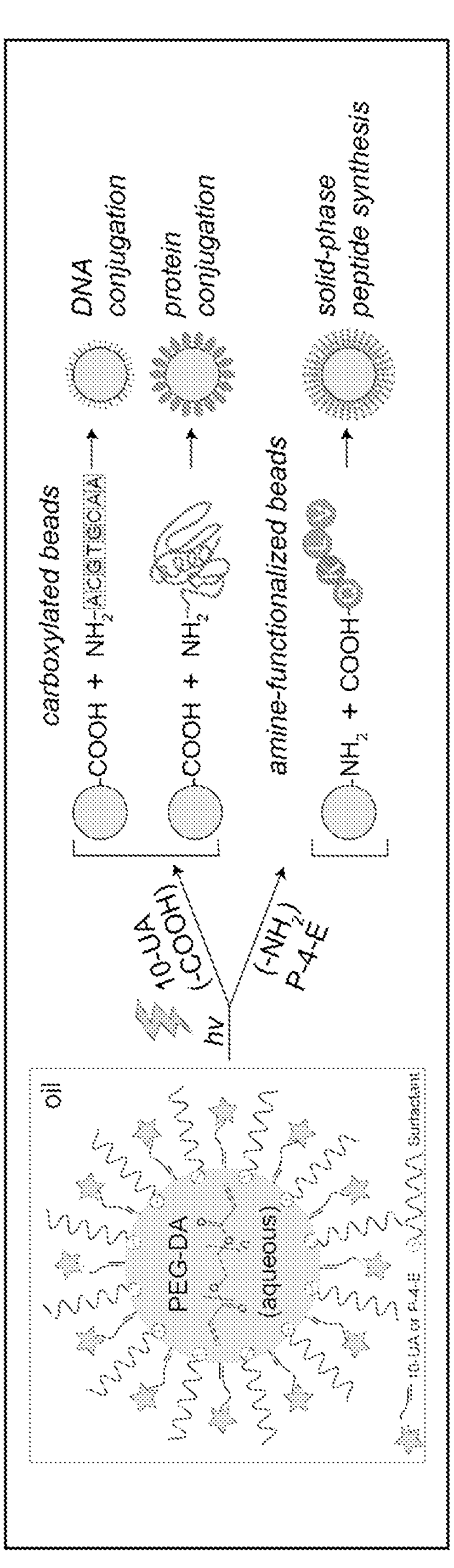
FIG. 3A is a schematic illustration of functionalization of poly(ethylene glycol) diacrylate (PEGDA) hydrogel microbeads for downstream DNA, protein, or peptide coupling.

Multiplexed bioassays designed to screen for binding interactions require the ability to couple 'bait' analytes of interest (for example, DNA oligonucleotides, whole proteins, or chemically synthesized peptides) to the microbead surface at high density and without the possibility of crosstalk or analyte dissociation over long storage timescales. Covalent coupling is particularly robust and typically relies on two main functional groups: —COOH (carboxyl groups) or —$NH_2$ (amine groups) (FIG. 3A). Carboxyl groups on the microbeads facilitate subsequent covalent coupling of any molecules bearing a free amine group to microbeads in aqueous/organic solvents (for example, whole proteins bearing an exposed primary amine or amine-functionalized DNA oligonucleotides). Amino groups displayed on microbeads provide convenient handles for covalent coupling of carboxylated molecules, such as during solid-phase synthesis of peptides directly on microbeads via standard Fmoc coupling chemistry.

In previously described microbeads, —COOH or —$NH_2$ moieties were covalently coupled to the PEGDA polymer chains in via Michael addition after the microbead synthesis, as described, for example, in (30). Present experiments used new functionalization approach, which leveraged solubility differences between —COOH— or —$NH_2$-terminated comonomers and photoinitiator (LAP) to drive polymerization of comonomers at the surface of the hydrogel matrix only (FIG. 3A). The exemplary comonomers used were 10-undecenoic acid (10-UA) for —COOH and pent-4-enylamine (P-4-E) for —$NH_2$. These comonomers were soluble in the HFE 7500 oil, while the LAP was only soluble in water. Exposure of LAP-containing aqueous droplets to UV drove a polymerization chain reaction that began in the aqueous PEGDA microsphere core and ultimately reached the oil/water interface to drive cross-linking of oil-soluble interfacial comonomers to the hydrogel microbead matrix (FIG. 3A). As the concentration of comonomer within the bulk oil phase was very low (0.2% v/v for 10-UA and 0.09% v/v for P-4-E), the chain reaction was then abolished to limit cross-linking to the oil/water interface.

Figure 3B:
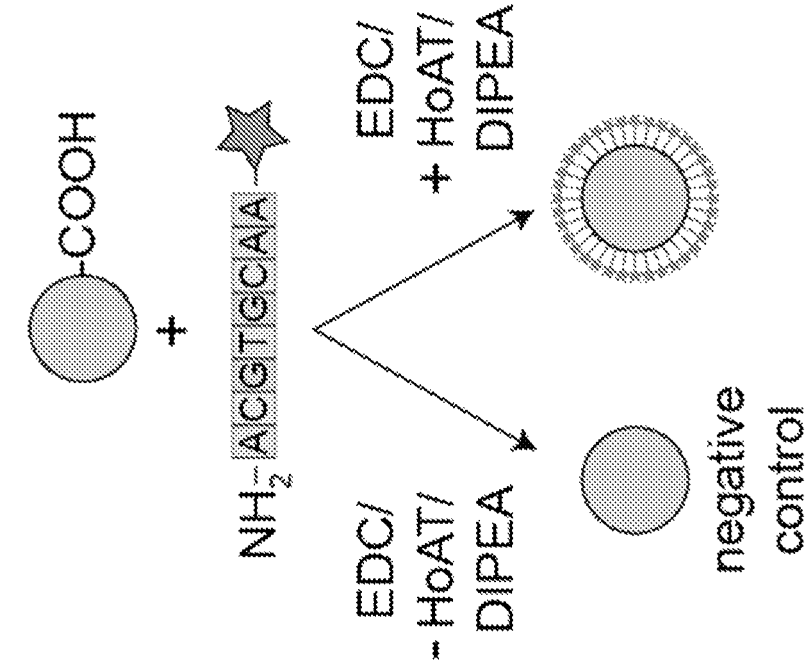
FIG. 3B is a schematic illustration of an assay used to quantify coupling of amine-functionalized oligonucleotides to carboxylated microbeads.
Figure 3C:
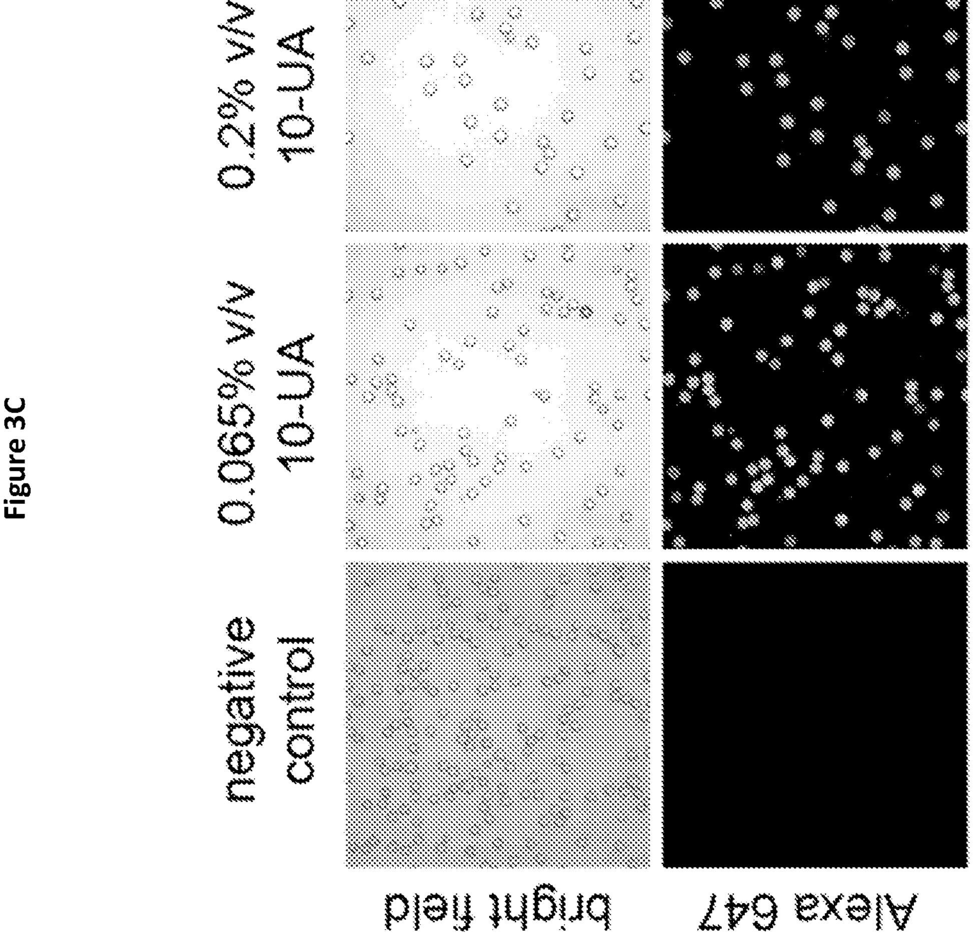
FIG. 3C shows bright field (top) and fluorescence (bottom) microphotographic images of microbeads polymerized in the presence of 0.065% or 0.2% v/v 10-undecenoic acid (10-UA) comonomers after conjugation with and without (negative control) required coupling reagents.
Figure 3D:
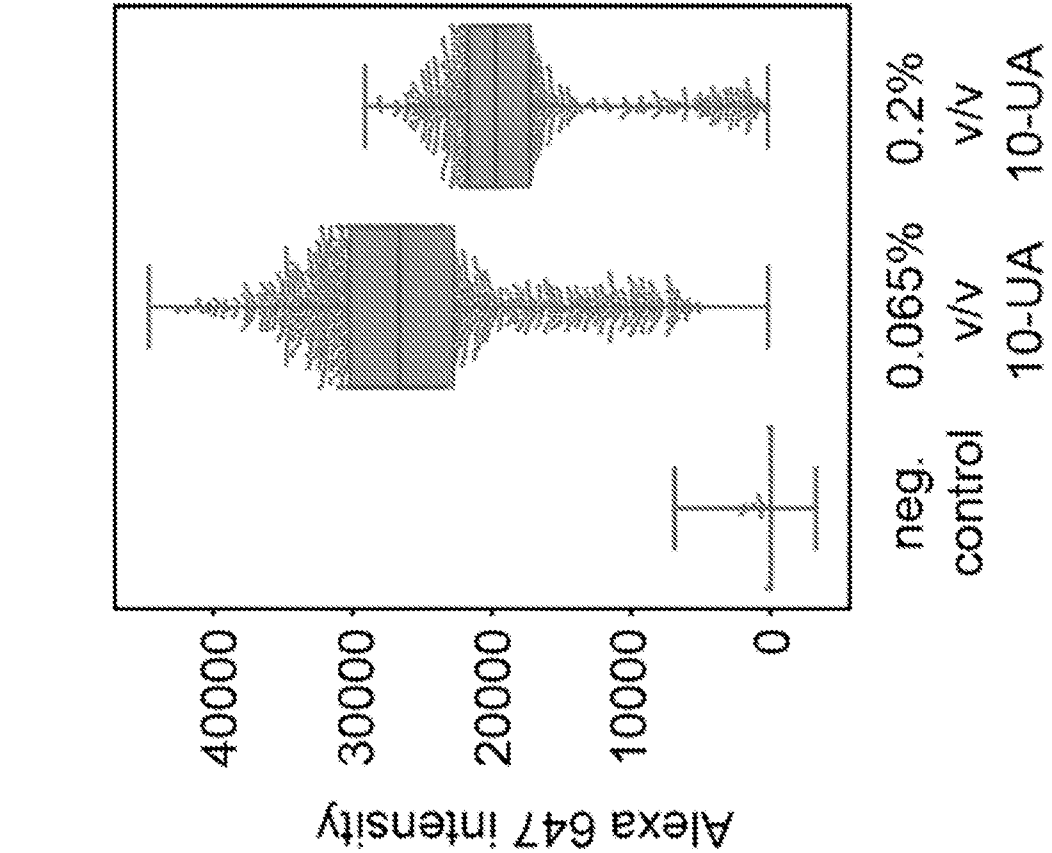
FIG. 3D is a plot showing median Alexa 647 intensities for all microbeads polymerized in the presence of 0.065% or 0.2% v/v 10-undecenoic acid (10-UA) comonomers after conjugation with and without required coupling reagents.

Example 5: Direct Coupling of Oligonucleotides and Proteins and Biotin Conjugation Microbeads bearing —COOH functional groups at the surfaces were synthesized as described in Example 4. Fluorescently labeled, $NH_2$-functionalized oligonucleotides were coupled to thus functionalized Microbeads via EDC chemistry (FIG. 3B). Images of microbeads after coupling and washing established that fluorescence intensities were relatively even across microbeads (CV approximately 27%) and high only when the coupling was performed in the presence of HoAT/DIPEA coupling reagents, establishing that coupling is specific (FIGS. 3B-D). Bright field and fluorescence images further established that the microbeads were undamaged after exposure to coupling reagents, and that unbound oligonucleotides were effectively removed by washing (FIGS. 3B-D). The comparison of fluorescence signals for microbeads polymerized in the presence of 2 different concentrations of 10-UA revealed that signal intensities were higher but slightly more heterogeneous for 0.065% (v/v) 10-UA, likely reflecting the incomplete coverage of the whole droplet surface, as discussed in (33). Estimation of loading densities by DNA conjugation for the 0.2% (v/v) 10-UA condition suggested that approximately $10^7$ to $10^8$ oligonucleotide bound to the surface of each microbead, which was consistent with prior estimates of microbead loading capacities provided, for example, in (30).

Figure 3E:
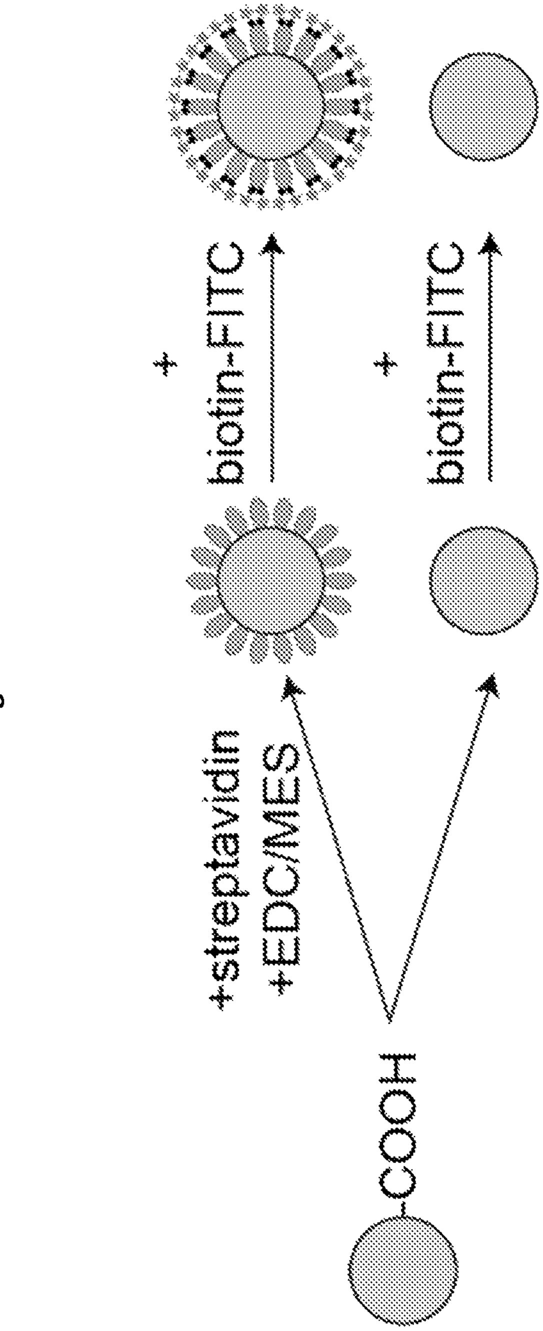
FIG. 3E is a schematic illustration of an assay used to quantify coupling of streptavidin proteins to carboxylated microbeads.
Figure 3F:
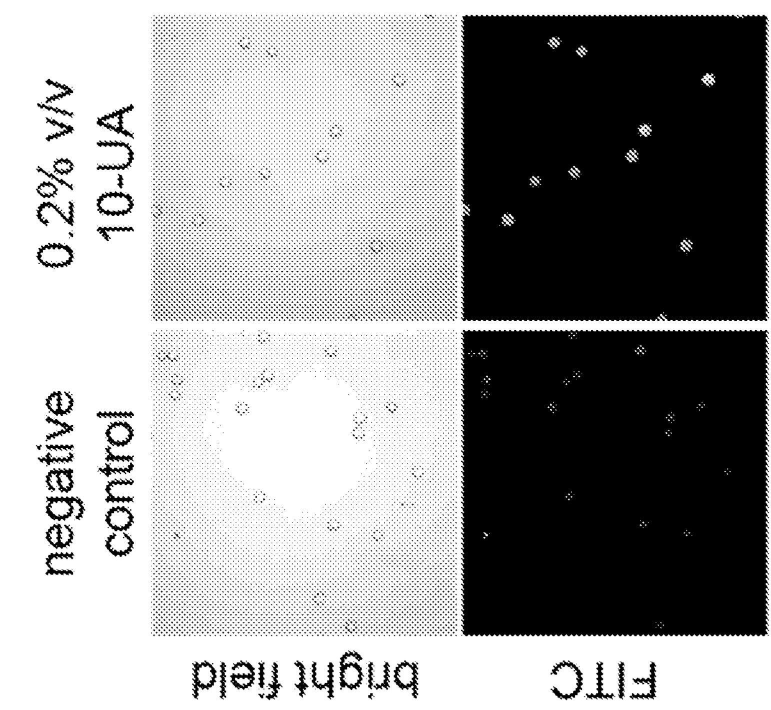
FIG. 3F shows representative microphotographic images of microbeads incubated with biotin-fluorescein isothiocyanate (FITC).
Figure 3G:
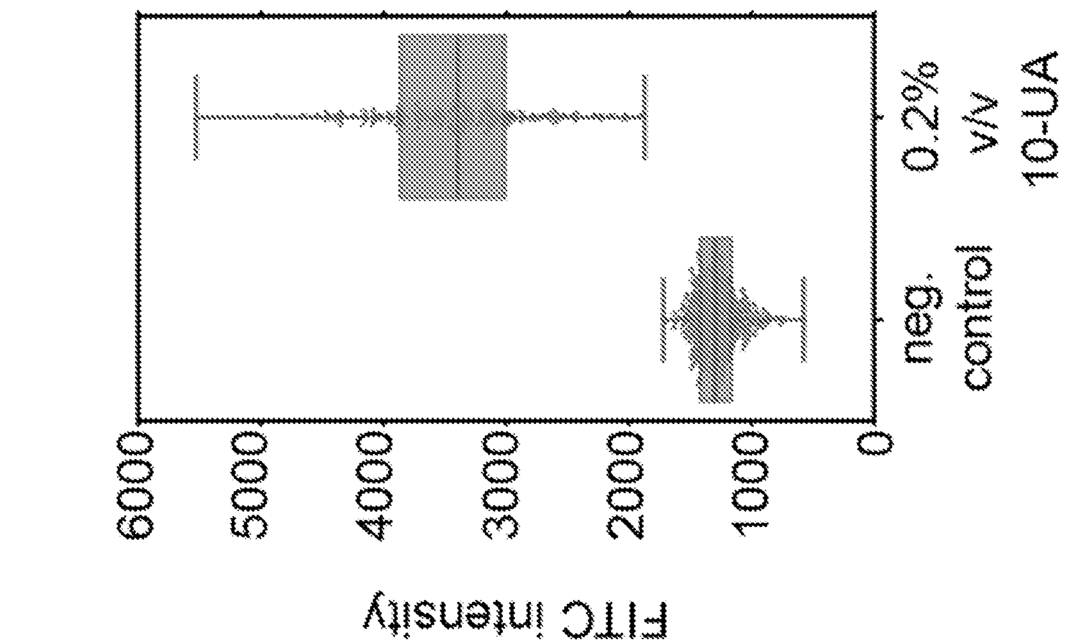
FIG. 3G shows median FITC intensities for all microbeads incubated with biotin-FITC.

To demonstrate the suitability of carboxylated microbeads for covalent coupling of entire proteins under aqueous environment, the experiments were conducted to test the ability of the surfaces of carboxylated microbeads to attach streptavidin molecules via their primary amines. To visualize any attached streptavidin, the microbeads were incubated with biotin-FITC conjugates, washed 3 times and imaged (FIG. 3E). As with the DNA conjugation reactions, significant FITC intensities were observed only after covalently coupling streptavidin to surfaces and not in the absence of coupling reagents (FIGS. 3F and G).

Figure 3H:
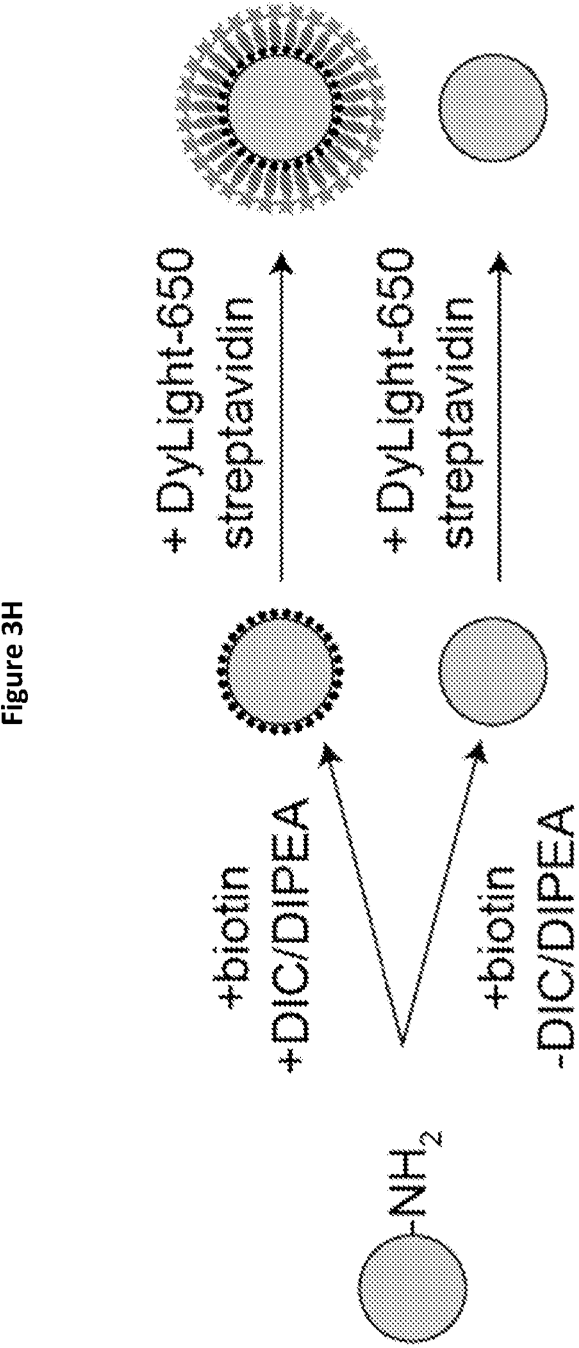
FIG. 3H is a schematic illustration of an assay used to quantify on-bead peptide synthesis.
Figure 3I:
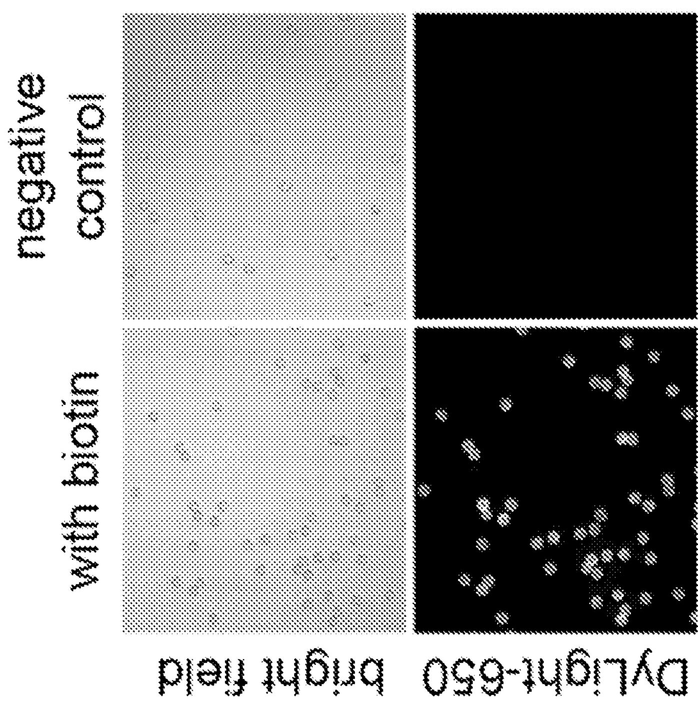
FIG. 3I shows representative images of microbeads after incubation with DyLight-650-labeled streptavidin.
Figure 3J:
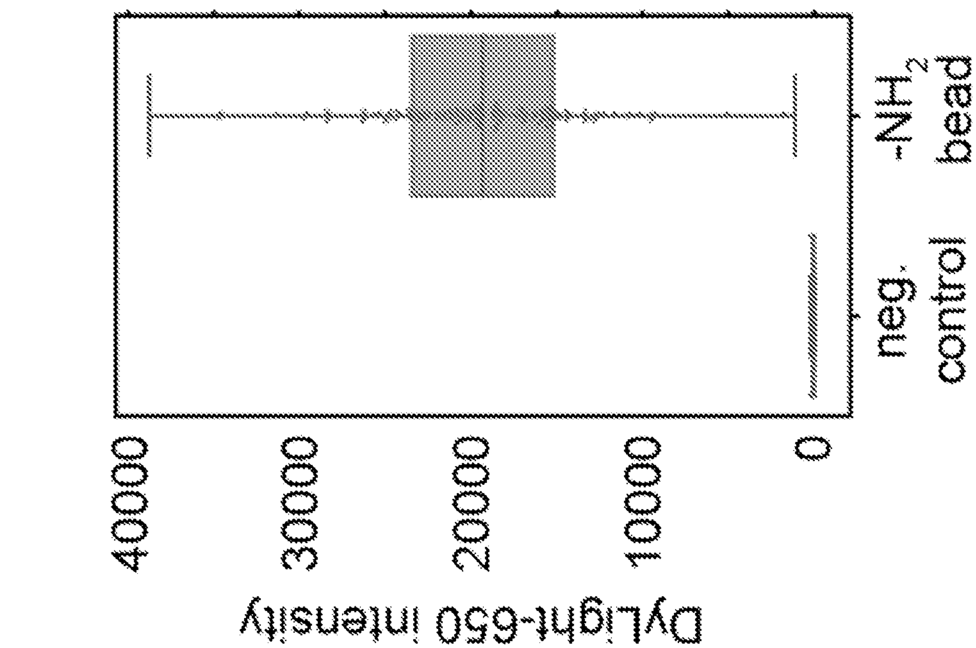
FIG. 3J is a plot of median DyLight-650 intensities after incubation with DyLight-650-labeled streptavidin.

Feasibility of using $NH_2$-functionalized Microbeads for solid-phase peptide synthesis was demonstrated by: (1) polymerizing Microbeads with P-4-E (0.09%, v/v) added to the oil phase, (2) incubating these functionalized Microbeads with biotin (which bears a free —COOH group analogous to standard Fmoc-amino acids) in either the presence or absence of required coupling reagents, (3) incubating with DyLight 650-labeled streptavidin, (4) washing, and then (5) imaging to quantify amount of microbead-bound fluorescence (FIG. 3H). As with the other coupling reactions, strong fluorescence was observed only in the presence of coupling reagents, establishing that presented $NH_2$ groups were suitable for subsequent specific conjugation (FIGS. 3I and J).

Example 6: Separation Efficiencies and Coding Capacity of Magnetic Microbeads

The ability to selectively magnetize particles provides an additional coding axis, thereby increasing the number pf codes that can be distinguished from one another. For example, generating the same set of spectral codes in the presence and absence of magnetic particles increases coding capacity 2-fold. In addition, magnetic microbeads are advantageous for microbead-based separation, improving microbead retention during rinsing and removal of excess supernatant via the application of a magnetic field and facilitating more stringent washing. Magnetic microbeads can also aid in loading microbeads into microwells for high-throughput experiments, such as single-cell phenotyping.

Figure 4A:
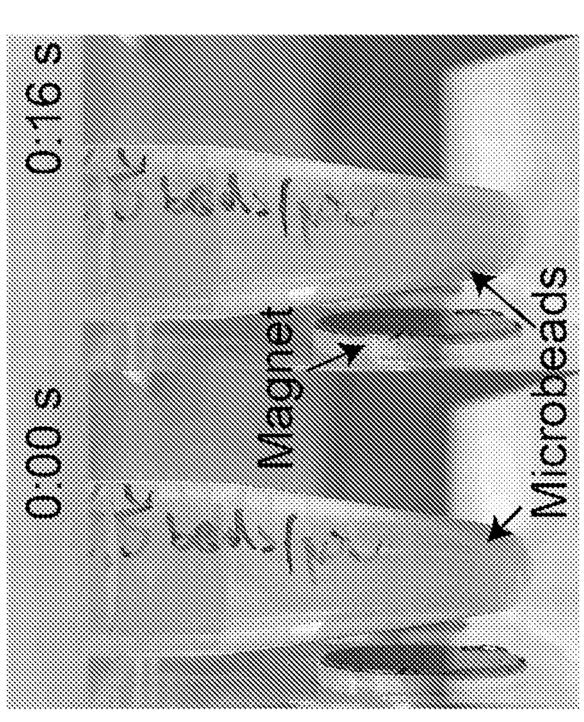
FIG. 4A shows photographic images illustrating magnet-induced movement of microbead-containing magnetic nanoparticles.

To test the ability to create magnetic microbeads, $Fe_3O_4$ nanoparticles were synthesized by modifying a previously described in (34) co-precipitation method to include extra poly (acrylic acid) (PAA) in the precursor solution, thereby enhancing control of nucleation and nanoparticle wrapping, as well as preventing nanoparticle aggregation. The resultant $Fe_3O_4$ nanoparticles were approximately 46 nm in diameter and appeared optically transparent. When these $Fe_3O_4$ nanoparticles were incorporated within microbeads, all the microbeads in a plastic tube were attracted to one side of the tube by simply holding a magnet at the side of the tube (FIG. 4A).

Figure 4B:
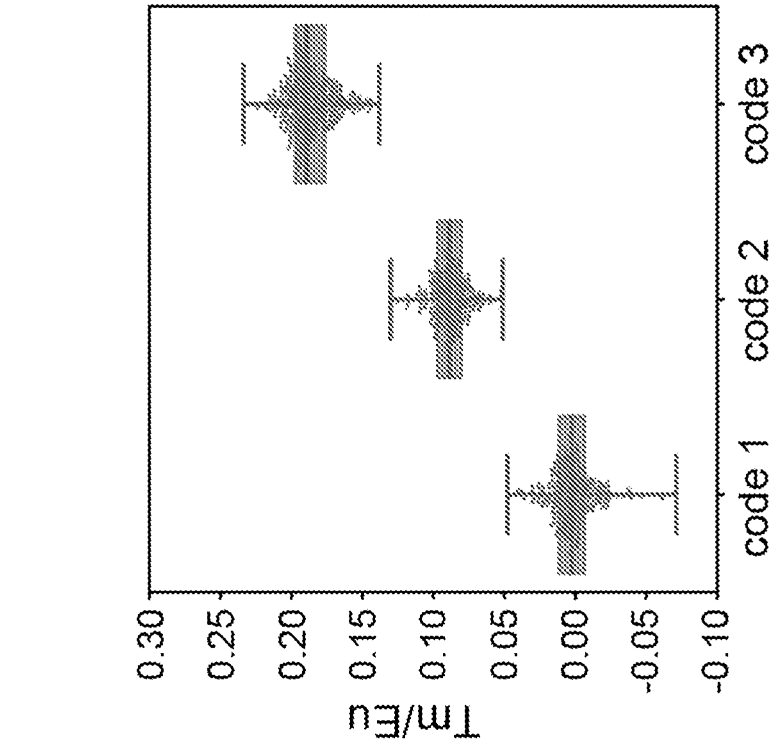
FIG. 4B is a plot of measured Tm/Eu intensities for microbeads containing magnetic nanoparticles and 3 different Tm/Eu ratios.
Figure 4C:
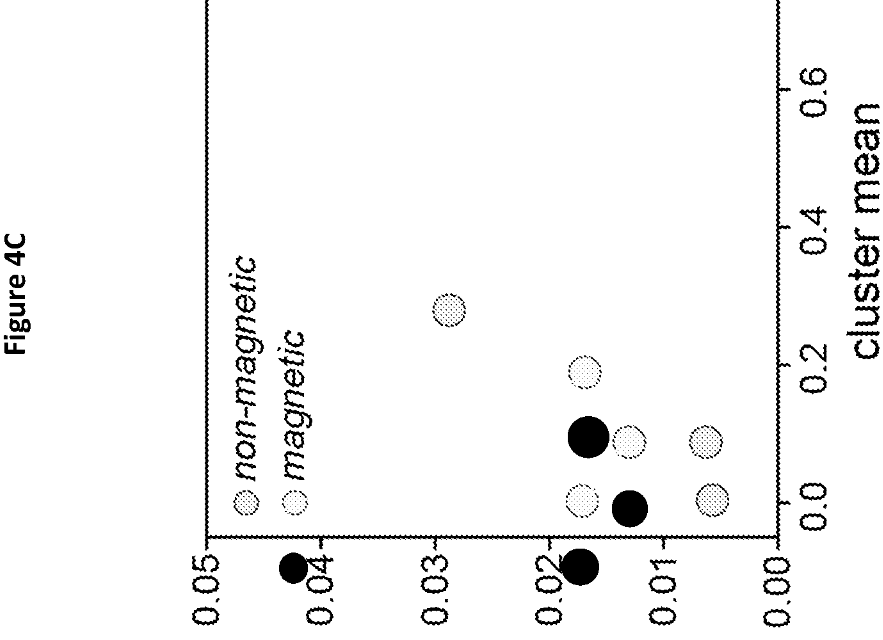
FIG. 4C is a plot of measured cluster variance for Tm/Eu code clusters in the presence and absence of magnetic nanoparticles.
Figure 4D:
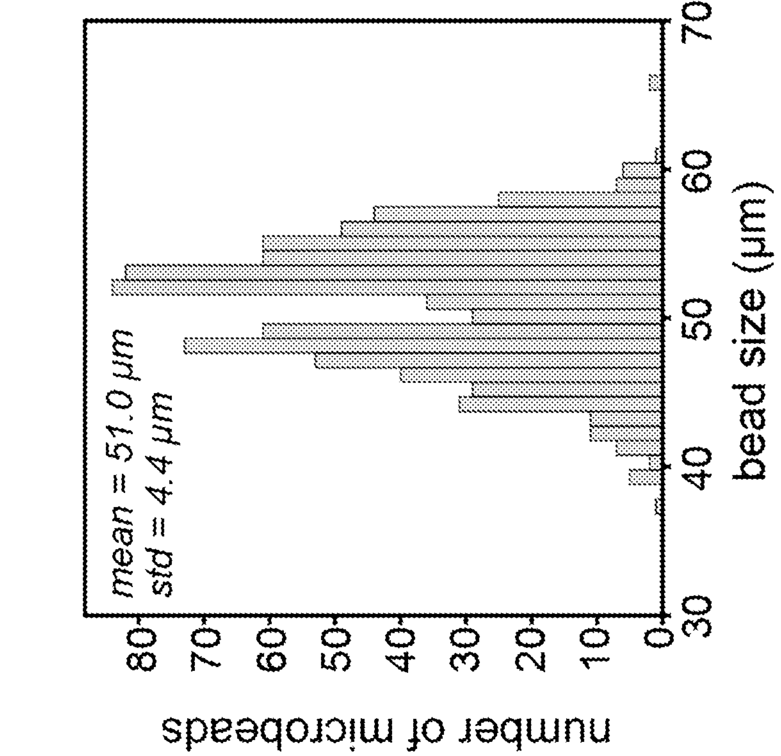
FIG. 4D is a plot of measured size distribution for spectrally encoded magnetic microbeads.

To test the resolution of the spectral codes in the presence of 10% $Fe_3O_4$ nanoparticles, a small library of microbeads including a single lanthanide species was synthesized. In prior encoding efforts, Tm has consistently been the least efficient emitter (32) due to relatively low energy transfer efficiency between doped $Tm^{3+}$ and $VO_4^{3-}$, resulting in weak blue emission (35). To provide a particularly stringent test of potential coding capacity, magnetic microbeads containing the 3 lowest Tm/Eu levels used previously (see FIG. 2) were synthesized and mixed together. The 3 populations were resolved (FIG. 4B) with all 3 levels clearly distinguishable from one another, with a <0.01% probability of miscalling a code. Comparison of Tm/Eu cluster variance as a function of mean Tm/Eu level further established that variances were only approximately 2-fold higher in the presence of magnetic nanoparticles (FIG. 4C), suggesting that up to 1,000-plex spectral code spaces remained possible. As with prior tests, magnetic Microbeads were fairly monodispersed, with diameters of 51±4 μm (FIG. 4D, mean±standard deviation; CV=7.8%).

Example 7: Exponential Droplet Splitting During Microbead Production

Figure 5C:
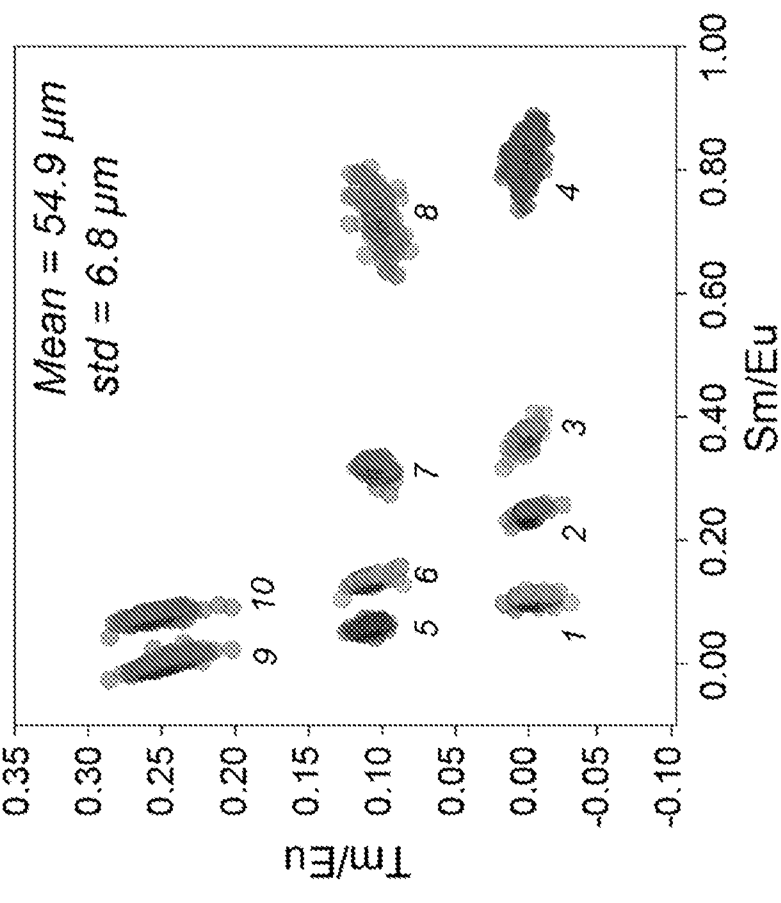
FIG. 5C is a plot of measured Tm/Eu and Sm/Eu ratios and microbead sizes (inset) for microbeads from a 10-code set produced via exponential droplet splitting.

Leveraging microbeads for broad use requires the ability to rapidly and economically produce large numbers of microbeads. While increasing fluid flow rates can boost droplet production within a narrow range, large increases in flow rate drive a transition in droplet formation between dripping to turbulent jetting regimes, yielding very polydisperse microbeads. To avoid the disadvantages of the above approach, throughput of the production process was increased by adding additional parallel flow focusers (FFs) to the synthesis device described above (FIG. 5A). In an alternative approach, a device was designed and fabricated that combined exponential droplet splitting with out-of-plane fluidic connections to boost droplet production rates without increasing device area. In the above device, a large droplet (approximately 160 μm in lateral diameter and 50 μm in height) was initially split to form two smaller ones when encountering two bifurcated channels (FIG. 5A). These smaller droplets were subsequently split by more Y-junction structures, thus generating an exponential amplification of microbead production (with rates increased by 2', where N represents the number of splitting cycles) (FIGS. 5B and C). As discussed in Example 1, produced droplets were routed to a single outlet via out-of-plane fluidic connections, collected, and polymerized as a batch via flood UV. For a device with 8×4 splitters (8 splitters in each pathway, 4 pathways total), measured droplet production rates averaged $10^6$/min at aqueous stream flow rate of 1500 μl/h and oil stream flow rate of 5400 μl/h, an approximately 3-fold increase over a linear production device with 4 FFs (FIG. 1B). Resultant droplets were slightly more polydisperse (CV=12%) than those generated by a linear amplification method (illustrated in FIG. 1C), but the spectral codes remain easily distinguishable from one another (FIG. 5C).

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

PUBLICATIONS CITED IN THIS DISCLOSURE

1 Kingsmore, S. F. Multiplexed protein measurement: technologies and applications of protein and antibody arrays. Nature reviews Drug discovery 5, 310-321 (2006).

2 Heller, M. J. DNA microarray technology: devices, systems, and applications. *Annual review of biomedical engineering* 4, 129-153 (2002).

3 Braeckmans, K., De Smedt, S. C., Leblans, M., Pauwels, R. & Demeester, J. Encoding microcarriers: present and future technologies. *Nature reviews Drug discovery* 1, 447-456 (2002).

4 Finkel, N. H., Lou, X., Wang, C. & He, L. Peer Reviewed: Barcoding the Microworld. *Analytical Chemistry* 76, 352 A-359 A, doi:10.1021/ac0416463 (2004).

5 Wilson, R., Cossins, A. R. & Spiller, D. G. Encoded microcarriers for high-throughput multiplexed detection. *Angewandte Chemie International Edition* 45, 6104-6117 (2006).

6 Birtwell, S. & Morgan, H. Microparticle encoding technologies for high-throughput multiplexed suspension assays. Integrative Biology 1, 345-362 (2009).

7 Broder, G. R. et al. Diffractive micro bar codes for encoding of biomolecules in multiplexed assays. *Analytical chemistry* 80, 1902-1909 (2008).

8 Cederquist, K. B., Dean, S. L. & Keating, C. D. Encoded anisotropic particles for multiplexed bioanalysis. *Wiley Interdisciplinary Reviews: Nanomedicine and Nanobiotechnology* 2, 578-600 (2010).

9 Lawrie, G. A., Battersby, B. J. & Trau, M. Synthesis of optically complex core—shell colloidal suspensions: pathways to multiplexed biological screening. Advanced Functional Materials 13, 887-896 (2003).

10 Lee, H., Kim, J., Kim, H., Kim, J. & Kwon, S. Colour-barcoded magnetic microparticles for multiplexed bioassays. Nature materials 9, 745 (2010).

11 Kim, L. N. et al. Shape-encoded silica microparticles for multiplexed bioassays. *Chemical Communications* 51, 12130-12133 (2015).

12 Chapin, S. C., Appleyard, D. C., Pregibon, D. C. & Doyle, P. S. Rapid microRNA profiling on encoded gel microparticles. *Angewandte Chemie International Edition* 50, 2289-2293 (2011).

13 Appleyard, D. C., Chapin, S. C. & Doyle, P. S. Multiplexed protein quantification with barcoded hydrogel microparticles. *Analytical chemistry* 83, 193-199 (2010).

14 Zhang, F. et al. Fluorescence Upconversion Microbarcodes for Multiplexed Biological Detection: Nucleic Acid Encoding. *Advanced Materials* 23, 3775-3779, doi:10.1002/adma.201101868 (2011).

15 Zhang, F. et al. Rare-Earth Upconverting Nanobarcodes for Multiplexed Biological Detection. *Small* 7, 1972-1976, doi:10.1002/sml1.201100629 (2011).

16 Purohit, S. et al. Multiplex glycan bead array for high throughput and high content analyses of glycan binding proteins. Nature Communications 9, 258, doi:10.1038/541467-017-02747-y (2018).

17 Fulton, R. J., McDade, R. L., Smith, P. L., Kienker, L. J. & Kettman, J. R. Advanced multiplexed analysis with the FlowMetrix™ system. Clinical chemistry 43, 1749-1756 (1997).

18 Houser, B. Bio-Rad's Bio-Plex® suspension array system, xMAP technology overview. Archives of Physiology and Biochemistry 118, 192-196, doi:10.3109/13813455.2012.705301 (2012).

19 Waterboer, T., Sehr, P. & Pawlita, M. Suppression of non-specific binding in serological Luminex assays. *Journal of Immunological Methods* 309, 200-204, doi:https://doi.org/10.1016/j.jim.2005.11.008 (2006).

20 Le Goff, G. C., Srinivas, R. L., Hill, W. A. & Doyle, P. S. Hydrogel microparticles for biosensing. European polymer journal 72, 386-412, doi:10.1016/j.eurpolymj.2015.02.022 (2015).

21 Ullah, F., Othman, M. B. H., Javed, F., Ahmad, Z. & Akil, H. M. Classification, processing and application of hydrogels: A review. Materials Science and Engineering: C57, 414-433, doi:https://doi.org/10.1016/j.msec.2015.07.053 (2015).

22 Moorthy, J., Burgess, R., Yethiraj, A. & Beebe, D. Microfluidic Based Platform for Characterization of Protein Interactions in Hydrogel Nanoenvironments. *Analytical chemistry* 79, 5322-5327, doi:10.1021/ac0702261 (2007).

23 Nallur, G. et al. Protein and Nucleic Acid Detection by Rolling Circle Amplification on Gel-based Microarrays. *Biomedical Microdevices* 5, 115-123, doi:10.1023/a:1024535110995 (2003).

24 Roh, Y. H., Lee, H. J. & Bong, K. W. Microfluidic Fabrication of Encoded Hydrogel Microparticles for Application in Multiplex Immunoassay. BioChip Journal 13, 64-81 (2019).

25 Dagher, M., Kleinman, M., Ng, A. & Juncker, D. Ensemble multicolour FRET model enables barcoding at extreme FRET levels. Nature Nanotechnology 13, 925-932, doi:10.1038/s41565-018-0205-0 (2018).

26 Liu, J., Sun, L., Zhan, H. & Fan, L.-J. Preparation of Fluorescence-Encoded Microspheres Based on Hydrophobic Conjugated Polymer—Dye Combination and the Immunoassay. *ACS Applied Bio Materials* 2, 3009-3018, doi:10.1021/acsabm.9b00337 (2019).

27 Nguyen, H. Q. et al. Programmable Microfluidic Synthesis of Over One Thousand Uniquely Identifiable Spectral Codes. *Advanced Optical Materials* 5, 1600548, doi:10.1002/adom.201600548 (2017).

28 Gerver, R. E. et al. Programmable microfluidic synthesis of spectrally encoded microspheres. *Lab on a Chip* 12, 4716-4723, doi:10.1039/c21c40699c (2012).

29 Nguyen, H. et al. *Peptide library synthesis on spectrally encoded beads for multiplexed protein/peptide bioassays*. Vol. 10061 PWB (*SPIE,* 2017).

30 Nguyen, H. Q. et al. Quantitative mapping of protein-peptide affinity landscapes using spectrally encoded beads. eLife 8, e40499, doi:10.7554/eLife.40499 (2019).

31 Huft, J., Da Costa, D. J., Walker, D. & Hansen, C. L. Three-dimensional large-scale microfluidic integration by laser ablation of interlayer connections. Lab on a Chip 10, 2358-2365, doi:10.1039/c004051g (2010).

32 Harink, B., Nguyen, H., Thorn, K. & Fordyce, P. An open-source software analysis package for Microspheres with Ratiometric Barcode Lanthanide Encoding (Microbeads). *PLOS ONE* 14, e0203725, doi:10.1371/journal-.pone.0203725 (2019).

33 Riechers, B. et al. Surfactant adsorption kinetics in microfluidics. Proceedings of the National Academy of Sciences, 201604307, doi:10.1073/pnas.1604307113 (2016).

34 Upadhyay, S., Parekh, K. & Pandey, B. Influence of crystallite size on the magnetic properties of $Fe_3O_4$ nanoparticles. *Journal of Alloys and Compounds* 678, 478-485, doi:https://doi.org/10.1016/j.jallcom.2016.03.279 (2016).

35 An, Z., Xiao, X., Yu, J., Mao, D. & Lu, G. Controlled synthesis and luminescent properties of assembled spherical YPxV1—x04:Ln3+(Ln=Eu, Sm, Dy or Tm) phosphors with high quantum efficiency. RSC Advances 5, 52533-52542, doi:10.1039/c5ra08993j (2015).

36 Nisisako, T., Ando, T. & Hatsuzawa, T. High-volume production of single and compound emulsions in a microfluidic parallelization arrangement coupled with coaxial annular world-to-chip interfaces. Lab on a Chip 12, 3426-3435, doi:10.1039/c21c40245a (2012).

37 Femmer, T. et al. High-Throughput Generation of Emulsions and Microgels in Parallelized Microfluidic Drop-Makers Prepared by Rapid Prototyping. *ACS Applied Materials & Interfaces* 7, 12635-12638, doi:10.1021/acsami.5b03969 (2015).

38 Sugiura, S., Nakajima, M., Tong, J., Nabetani, H. & Seki, M. Preparation of Monodispersed Solid Lipid Microspheres Using a Microchannel Emulsification Technique. *Journal of Colloid and Interface Science* 227, 95-103, doi:https://doi.org/10.1006/jcis.2000.6843 (2000).

39 Yadavali, S., Jeong, H.-H., Lee, D. & Issadore, D. Silicon and glass very large scale microfluidic droplet integration for terascale generation of polymer microparticles. Nature Communications 9, 1222, doi:10.1038/541467-018-03515-2 (2018).

40 Conchouso, D., Castro, D., Khan, S. A. & Foulds, I. G. Three-dimensional parallelization of microfluidic droplet generators for a litre per hour volume production of single emulsions. Lab on a Chip 14, 3011-3020, doi:10.1039/c41c00379a (2014).

41 Dangla, R., Kayi, S. C. & Baroud, C. N. Droplet microfluidics driven by gradients of confinement. Proceedings of the National Academy of Sciences 110, 853, doi:10.1073/pnas.1209186110 (2013).

42 Romanowsky, M. B., Abate, A. R., Rotem, A., Holtze, C. & Weitz, D. A. High throughput production of single core double emulsions in a parallelized microfluidic device. Lab on a Chip 12, 802-807, doi:10.1039/c21c21033a (2012).

43 Mulligan, M. K. & Rothstein, J. P. Scale-up and control of droplet production in coupled microfluidic flow-focusing geometries. Microfluidics and Nanofluidics 13, 65-73, doi:10.1007/s10404-012-0941-7 (2012).

44 Li, W., Greener, J., Voicu, D. & Kumacheva, E. Multiple modular microfluidic (M3) reactors for the synthesis of polymer particles. Lab on a Chip 9, 2715-2721, doi:10.1039/b906626h (2009).

45 Lee, S.-A. et al. Spheroid-based three-dimensional liver-on-a-chip to investigate hepatocyte—hepatic stellate cell interactions and flow effects. *Lab on a Chip* 13, 3529-3537, doi:10.1039/c31c50197c (2013).

46 Utharala, R., Tseng, Q., Furlong, E. E. M. & Merten, C. A. A Versatile, Low-Cost, Multiway Microfluidic Sorter for Droplets, Cells, and Embryos. *Analytical chemistry* 90, 5982-5988, doi:10.1021/acs.analchem.7b04689 (2018).

47 Hermanson, G. T. in Bioconjugate Techniques (Third Edition) (ed Greg T. Hermanson) 229-258 (Academic Press, 2013).

48 Stoeckius, M. et al. Simultaneous epitope and transcriptome measurement in single cells. *Nature Methods* 14, 865-868, doi:10.1038/nmeth.4380 (2017).

49 Mimitou, E. P. et al. Multiplexed detection of proteins, transcriptomes, clonotypes and CRISPR perturbations in single cells. *Nature Methods* 16, 409-412, doi:10.1038/s41592-019-0392-0 (2019).

50 Ahmed, N., Sukovich, D. & Abate, A. R. Operation of Droplet-Microfluidic Devices with a Lab Centrifuge. Micromachines 7, 161, doi:10.3390/mi7090161 (2016).

51 Chen, Z. et al. Centrifugal micro-channel array droplet generation for highly parallel digital PCR. *Lab on a Chip* 17, 235-240, doi:10.1039/c61c01305h (2017).

52 Shin, D.-C., Morimoto, Y., Sawayama, J., Miura, S. & Takeuchi, S. Centrifuge-based step emulsification device for simple and fast generation of monodisperse picoliter droplets. Sensors and Actuators B: Chemical 301, 127164, doi:https://doi.org/10.1016/j.snb.2019.127164 (2019).

53 Visser, C. W., Kamperman, T., Karbaat, L. P., Lohse, D. & Karperien, M. In-air microfluidics enables rapid fabrication of emulsions, suspensions, and 3D modular (bio) materials. Science Advances 4, eaao1175, doi:10.1126/sciadv.aao1175 (2018).

54 Xia, Y. & Whitesides, G. M. Soft Lithography. *Angewandte Chemie International Edition* 37, 550-575, doi:10.1002/(sici)1521-3773(19980316)37:5<550::aid-anie550>3.0.co; 2-g (1998).

55 Li, Y. et al. Optimized Reaction Conditions for Amide Bond Formation in DNA-Encoded Combinatorial Libraries. *ACS Combinatorial Science* 18, 438-443, doi:10.1021/acscombsci.6b00058 (2016).

56 Xu, et al. Rapid synthesis of size-controllable $YVO_4$ nanoparticles by microwave irradiation, Solid State Communications, 130, 465-468 (2004).

57 Choi, et al. Luminescent properties of PEG-added nanocrystalline $YVO_4:Eu^{3+}$ phosphor prepared by a hydrothermal method. *Journal of Luminescence* 130, 549-553 (2010).

58 Wang, et al. Multicolor Tuning of (Ln, P)-Doped $YVO_4$ Nanoparticles by Single-Wavelength Excitation. *Angewandte Chemie International Edition* 47, 906-909 (2008)

59 Christopher, G. F., and S. L. Anna. Microfluidic methods for generating continuous droplet streams. *Journal of Physics D: Applied Physics* 40.19, R319 (2007).

60 T. Thorsen, R. W. Roberts, F. H. Arnold & S. R. Quake Dynamic pattern formation in a vesicle-generating microfluidic device. *Physical Review Letters,* 86(18), 4163-4166 (2001).

61 Dreyfus, R., Tabeling, P., & Willaime, H. Ordered and disordered patterns in two-phase flow in microfluidics. Physical review letters, 90, 144505-144507 (2003).

62 Tice, J. D., Lyon, A. D., & Ismagilov, R. F. Effects of viscosity on droplet formation and mixing in microfluidic channels. Analytica chimica acta, 507, 73— 77 (2004).

63 Garstecki, P., Fuerstman, M. J., Stone, H. A., & Whitesides, G. M. Formation of droplets and bubbles in a microfluidic T-junction scaling and mechanism of breakup. Lab on a Chip, 6(3), 437-446 (2006).

64 T. Cubaud and T. G. Mason, Capillary threads and viscous droplets in square microchannels Physics of Fluids, 20, 053302 (2008).

65 A. M. Ganan-Calvo and J. M. Gordillo Perfectly monodisperse microbubbling by capillary flow focusing, *Physical Review Letters,* 87, 274501 (2001)

66 Anna, S. L., Bontoux, N., and Stone, H. A. Formation of dispersions using "flow focusing" in microchannels. *Applied Physics Letters,* 82(3), 364-366 (2003).

67 J. Tan, J. H. Xu, S. W. Li et G. S. Luo Drop dispenser in a cross-junction microfluidic device: Scaling and mechanism of break-up. Chemical Engineering Journal, 136(2-3), 306-311 (2008).

68 L. Yobas, S. Martens, W.-L. Ong, and N. Ranganathan High—performance flow—focusing geometry for spontaneous generation of monodispersed droplets, Lab on Chip, vol. 6, pp. 1073-1079 (2006).

69 Abate, A. R., Poitzsch, A., Hwang, Y., Lee, J., Czerwinska, J., and Weitz, D. A. "Impact of inlet channel geometry on microfluidic drop formation". *Phys. Rev. E,* 80(2), 026310 (2009).

70 Utada, A. S., Fernandez-Nieves, A., Stone, H. A., and Weitz, D. A. "Dripping to jetting transitions in coflowing liquid streams". *Phys. Rev. Lett.,* 99(9), 094502 (2007).

71 S. L. Anna et H. C. Mayer "Microscale tipstreaming in a microfluidic flow focusing device". Physics of Fluids, 18(12), 121512 (2006).

72 L. Peng, M. Yang, S.-S. Guo, W. Liu et X.-Z. Zhao "The effect of interfacial tension on droplet formation in flow-focusing microfluidic device." *Biomedical Microdevices,* 13 (3), 559-564 (2011).

73 P. B. Umbanhowar, V. Prasad, and D. A. Weitz "Monodisperse emulsion generation via drop break off in a coflowing stream," *Langmuir,* 16, 347-351 (2000)

74 C. Cramer, P. Fischer, and E. J. Windhab "Drop formation in a co—flowing ambient fluid," Chemical Engineering *Science,* 59, 3045-3058 (2004).

75 Y. Hong and F. Wang "Flow rate effect on droplet control in a co-flowing microfluidic device," Microfluidics and Nanofluidics, 3, 341-346 (2007).

76 R. Xiong, M. Bai, and J. Chung "Formation of bubbles in a simple co—flowing microchannel," *Journal of Micromechanics and Microengineering,* 17, 1002-1011 (2007).

77 G. I. Taylor, "The formation of emulsions in definable fields of flow" Proceedings of the Royal Society of London. Series A, Containing Papers of a Mathematical and Physical Character, 146 (858), 501-523 (1934).

78 Ward et al. "Microfluidic flow focusing: Drop size and scaling in pressure versus flow-rate-driven pumping" *Electrophoresis,* 26, 3716-3724 (2005).

What is claimed is:

1. A method for producing polymeric microbeads comprising lanthanide nanoparticles, comprising:

i) providing a first fluid comprising a microbead matrix component and lanthanide nanoparticles, and a second fluid, wherein the first fluid and the second fluid are immiscible;

ii) contacting the first fluid with the second fluid in a microfluidic device, thereby forming droplets of the first fluid;

iii) removing the formed droplets from the microfluidic device; and iv) solidifying the microbead matrix component of the formed droplets after the formed droplets are removed from the microfluidic device, thereby forming the polymeric microbeads comprising lanthanide nanoparticles outside of the microfluidic device.

2. The method of claim 1, wherein step (i) comprises mixing components of the first fluid outside of the microfluidic device before introducing the first fluid into the microfluidic device.

3. The method of claim 1, wherein step (ii) comprises contacting the first fluid with the second fluid at one or more intersections of channels of the microfluidic device.

4. The method of claim 1, wherein step (iv) comprises exposing the formed droplets to a temperature or to a compound inducing solidification of the microbead matrix component.

5. The method of claim 1, wherein the microbead matrix component is a polymerizable component, and step (iv) comprises polymerizing the polymerizable component.

6. The method of claim 5, wherein the first fluid comprises a photoinitiator, and step (iv) comprises irradiating the formed droplets removed from the microfluidic device with UV radiation to polymerize the polymerizable component.

7. The method of claim 6, wherein in step (iv) the formed droplets are simultaneously irradiated as a batch.

8. The method of claim 1, wherein the first fluid is hydrophobic, and the second fluid is hydrophilic, or the first fluid is hydrophilic, and the second fluid is hydrophobic.

9. The method of claim 8, wherein the first fluid is aqueous, and the second fluid is hydrophobic.

10. The method of claim 8, wherein the first fluid is hydrophilic, and the second fluid is hydrophobic, and the microbead matrix component comprises one or more polymerizable hydrophilic monomers and/or polymers.

11. The method of claim 10, wherein the one or more hydrophilic monomers and/or polymers comprise one or more polyethylene glycol derivatives, one or more acrylamide derivatives, one or more methacrylamide derivatives, or combinations of two or more thereof.

12. The method of claim 8, wherein the first fluid is hydrophilic, and the second fluid is hydrophobic, and the hydrophobic fluid comprises an oil, a hydrocarbon, a fatty acid, a siloxane, a fluorocarbon, or a combination of two or more thereof.

13. The method of claim 1, wherein the lanthanide nanoparticles comprise a predetermined ratio of at least two types of lanthanide nanoparticles.

14. The method of claim 1, wherein step (ii) comprises flow focusing of the first fluid.

15. The method of claim 1, wherein the second fluid comprises an amphipathic compound capable of covalently bonding with the microbead matrix component during step (iv), thereby attaching the amphipathic compound to a surface of the polymeric microbeads.

16. The method of claim 15, wherein the amphipathic compound comprises a reactive group that remains free upon covalent bonding of the amphipathic compound to the surface of the polymeric microbeads, and the reactive group comprises a carboxyl group, an amino group, an azide group, a hydroxyl group, a hydrazide group or a chloromethyl group.

17. The method of claim 16, wherein the reactive group comprises a carboxyl group, and the method further comprises covalently coupling an amino-functionalized oligonucleotide to the surface of the polymeric microbeads.

18. The method of claim 16, wherein the reactive group comprises an amino group, and the method further comprises covalently coupling an amino acid, a peptide or a protein to the surface of the polymeric microbeads.

19. The method of claim 16, wherein the reactive group comprises an amino group, and the method further comprises performing solid-phase peptide synthesis on a surface of the polymeric microbeads.

20. The method of claim 1, wherein the first fluid further comprises ferric nanoparticles.

* * * * *